United States Patent [19]
Sudol et al.

[11] Patent Number: 6,022,740
[45] Date of Patent: Feb. 8, 2000

[54] SH3 KINASE DOMAIN ASSOCIATED PROTEIN, A SIGNALLING DOMAIN THEREIN, NUCLEIC ACIDS ENCODING THE PROTEIN AND THE DOMAIN, AND DIAGNOSTIC AND THERAPEUTIC USES THEREOF

[75] Inventors: Marius Sudol, New York, N.Y.; Peer Bork, Heidelberg, Germany; Henry Chen, New York, N.Y.

[73] Assignee: The Rockfeller University, New Yoek, N.Y.

[21] Appl. No.: 08/348,518

[22] Filed: Dec. 1, 1994

[51] Int. Cl.$^7$ .................................................. C12N 15/00
[52] U.S. Cl. ....................... 435/325; 536/23.1; 536/24.1; 435/69.1; 435/320.1; 435/325
[58] Field of Search .................................. 536/23.1, 24.1; 435/6, 69.1, 69.7, 69.2, 22, 23, 55, 66, 76, 77, 78

[56] References Cited

FOREIGN PATENT DOCUMENTS

WO 89/06286  7/1989  WIPO.

OTHER PUBLICATIONS

Coghlan, New Scientist, vol. 148,:14–15, 1995.
Gamburg et al., Molecular Medicine Today, vol. 1, No. 9 pp. 410–417, 1995.
Kumai et al., Biochem. Biophysical Res. Comms., vol. 185, 2: 1151–1161, 1992.
Wallace et al., Methods In Ezymology, 152:432, 1987.
Sambrook et al., Molecular Clonning, CSH: 11,47, 1989.
Crystal, Science, vol. 270: 404–410, 1995.
Sudol, Prog. Biophys. Molecular Biology, vol. 65, No. 1/2, pp. 113–132, 1996.
Mikkelsen, (TIG, vol. 9, 1993).
Dickinson, TIG, vol. 11, 4:119–120, col. 2 on p. 120, Apr. 1995.
Sudol et al. reference (FEBS Letters, 369:67–71, 1995).
Feller et al., 1994, EMBO J. 13:2341–51.
Ren et al., 1994, Genes and Develop. 8:783–95.
Sudol, 1994, Oncogene 9:2145–52.
Tinsley et al, 1994, Proc. Natl. Acad. Sci. USA 91:8307–13.
Yu et al., 1994, Cell 76:933–45.
Ahn and Kunkel, 1993, Nature Genetics 3:283–91.
Birge and Hanafusa, 1993, Science 262:1522–24.
Booker et al., 1993, Cell 73:813–22.
Kohda et al., 1993, Cell 72:953–60.
Koyama et al., 1993, Cell 72:945–52.
Li et al., 1993, Nature 363:85–88.
Mayer and Baltimore, 1993, Trends Cell Biol. 3:8–13.
Noble et al., 1993, EMBO J. 12:2617–24.
Pawson and Schlessinger, 1993, Curr. Biol. 3:434–42.
Ren et al., 1993, Science 259:1157–61.
Rozakis–Adcock et al., 1993, Nature 363:83–85.
Clark et al., 1992, Nature 356:340–44.
Kumar et al., 1992, Bioch. Biophys. Res. Comm. 185:1155–61.
Margolis, 1992, Cell Growth Diff. 3:73–80.
Musacchio et al., 1992, FEBS Lett. 307:55–61.
Musacchio et al., 1992, Nature 359:851–55.
Pawson and Gish, 1992, Cell 71:359–62.
Yu et al., 1992, Science 258:1665–68.
Cantley et al., 1991, Cell 64:281–302.
Sudol, 1989, J. Neurosci. Res.24:1–8.
Sudol et al., 1988, Nucl. Acids Res. 16:9876.
Sudol and Hanafusa, 1986, Mol. Cell. Biol. 6:2839–46.
Dulilio et al., 1991, Nucl. Acids Res. 19:5269–74.

*Primary Examiner*—Bruce R. Campell
*Assistant Examiner*—Dave Trong Nguyen
*Attorney, Agent, or Firm*—Klauber & Jackson

[57] ABSTRACT

The present invention relates to regulation and control of cellular processes by SH3-domain binding proteins, by putative signalling domains of such proteins, ligands of the signalling domain, and diagnosis and therapy based on the activity of such proteins, signalling domains, and ligands.

33 Claims, 21 Drawing Sheets

FIG. 2A

```
     GAATT                                                                     5
     CCCCGAGCACACAGAGCCATGAGCCCCGC GAGGAAGCCCAGGGGTCCCGCCAGCC                  65
 1   ATGGATCCCGGGCAGCCTCAGCCAGCAG     CCGCCGCAGGCGGCCAGCCCCGGCCCG             125
     MetAspProGlyGlnProGlnProGlnGln   ProProGlnAlaAlaGlnProProAlaPro
21   CAGCAGGCCCCGCAGCCCCCCGGGGCG      GGTCGGGAGCTCCGGAGGCGCGCAG               185
     GlnGlnAlaProGlnProProGlyAla      GlySerGlyAlaProGlyGlyAlaAlaGln
41   CCGCCGGGCGCGGGCCCCTCCGGCGGGG     CACCAGATCGTCCATGTGCGGGGCGACTCC          245
     ProProGlyAlaGlyProProProAlaGly   HisGlnIleValHisValArgGlyAspSer
61   GAGACCGACCTGGAGGCTCTCTTCAACGCC   GTGATGAACCCCAAGGGCGCCAACGTGCCG          305
     GluThrAspLeuGluAlaLeuPheAsnAla   ValMetAsnProLysGlyAlaAsnValPro
81   CACACGCTGCCCATGGCCCGACTCCGCAAGCTG CCGGACTCCTTCTTCAAGCCGCCCGAGCCC         365
     HisThrLeuProMetAlaArgLeuArgLysLeu ProAspSerPhePheLysProProGluPro
101  AAAGCTCACTCCCGCCAGGCCAGCACTGAC   GCAGGGACAGCAGGAGCCCTGACCCCTCAG          425
     LysAlaHisSerArgGlnAlaSerThrAsp   AlaGlyThrAlaGlyAlaLeuThrProGln
121  CATGTTGTGCTCATTCCTCTCCAGCATCA    CTGCAGCTGGGGCCGTCTCCCCTGGACG            485
     HisValValLeuIleProLeuGlnHisHis   LeuGlnLeuGlyLeuAlaValSerProGlyThr
141  CTCACACCCTCCGGAGTAGTGACCGGACCC   GGAGCTCCGTCTTCTCAGCATCCGCCAG            545
     LeuThrProSerGlyValValThrGlyPro   GlyAlaProSerSerGlnHisLeuArgGln
```

FIG.2B

```
161  TCTTCATTTGAGATCCCCTGATGATGTACCT CTGCCACCGGGCTGGGAGATGGCCAAAACA  605
     SerSerPheGluIleProAspAspValPro  LeuProProGlyTrpGluMetAlaLysThr

181  CCATCTGGACAGAGATACTTCCTTAATCAT  ATTGATCAAACAACAACATGGCAAGATCCC  665
     ProSerGlyGlnArgTyrPheLeuAsnHis  IleAspGlnThrThrThrTrpGlnAspPro

201  AGGAAGGCCATGCTTTCCCAGATGAACGTT  ACAGCTCCCACCAGTCCTCCCGTGCAACAG  725
     ArgLysAlaMetLeuSerGlnMetAsnVal  ThrAlaProThrSerProProValGlnGln

221  AACTTAATGAACTCAGCATCAGCCATGAAT  CAGCGCATCAGCCAAAGTGCTCCAGTGAAA  785
     AsnLeuMetAsnSerAlaSerAlaMetAsn  GlnArgIleSerGlnSerAlaProValLys

241  CAGCCACCCCCTGCTCCTCAGAGTCCC    CAAGGTGGTGTCATGGGTGGGAGTAGCTCC  845
     GlnProProProLeuAlaProGlnSerPro  GlnGlyGlyValMetGlyGlySerSerSer

261  AATCAGCAACAACAGAGATGAGACTTCAGCAG CTACAGATGGAGAAGGCTGAGACTG     905
     AsnGlnGlnGlnArgAspGluThrSerGln  LeuGlnMetGluLysGluArgLeuArgLeu

281  AAGCATCAAGAACTGCTTCGGCAGAATTG  GCTCTCCCTAGCCAGCTTCCAACGATGAA   965
     LysHisGlnGluLeuLeuArgGlnAsnLeu  AlaLeuArgSerGlnLeuProThrMetGlu

301  CAAGATGGTGGATCTCAAAATCCCGTATCA  TCTCCTGGAATGTCTCAGGAACTGAGGACT 1025
     GlnAspGlyGlySerGlnAsnProValSer  SerProGlyMetSerGlnGluLeuArgThr
```

```
1    GTCGACGGCCATTATGGATGGATGGCCGAGTGCCTCGCAGCCCCTCCCGAGGCGCAGCCG
61   CCAGACCAGTGGAGCCGGGGCGCAGGGCGGGGGCGGAGGCGCCGGGGCGGGGGATGCGGG
121  GCCGCGGCGCAGCCCCCCGGCCCTGAGAGCGAGGACAGCGCCGCCCGGCCCGCAGCCGTC
181  GCCGCTTCTCCACCTCGGCCCGTGGAGCCGGGGCGTCCGGGCGTAGCCCTCGCTCGCCTG
241  GGTCAGGGGTGCGCGTCGGGGGAGGCAGAAGCCATGGATCCCGGGCAGCAGCCGCCGCC
                                        M   D   P   G   Q   Q   P   P   P
301  TCAACCGGCCCCCCAGGGCCAAGGGCAGCCGCCTTCGCAGCCCCGCAGGGGCAGGGCCC
     Q   P   A   P   Q   G   Q   G   Q   P   P   S   Q   P   P   Q   G   Q   G   P
361  GCCGTCCGGACCCGGGCAACCGGCACCCGCGGCGACCCAGGCGGCGCCGCAGGCACCCCC
     P   S   G   P   G   Q   P   A   P   A   A   T   Q   A   A   P   Q   A   P   P
421  CGCCGGGCATCAGATCGTGCACGTCCGCGGGGACTCGGAGACCGACCTGGAGGCGCTCTT
     A   G   H   Q   I   V   H   V   R   G   D   S   E   T   D   L   E   A   L   F
481  CAACGCCGTCATGAACCCCAAGACGGCCAACGTGCCCCAGACCGTGCCCATGAGGCTCCG
     N   A   V   M   N   P   K   T   A   N   V   P   Q   T   V   P   M   R   L   R
541  GAAGCTGCCCGACTCCTTCTTCAAGCCGCCGGAGCCCAAATCCCACTCCCGACAGGCCAG
     K   L   P   D   S   F   F   K   P   P   E   P   K   S   H   S   R   Q   A   S
601  TACTGATGCAGGCACTGCAGGAGCCCTGACTCCACAGCATGTTCGAGCTCATTCCTCTCC
     T   D   A   G   T   A   G   A   L   T   P   Q   H   V   R   A   H   S   S   P
661  AGCTTCTCTGCAGTTGGGAGCTGTTTCTCCTGGGACACTGACCCCCACTGGAGTAGTCTC
     A   S   L   Q   L   G   A   V   S   P   G   T   L   T   P   T   G   V   V   S
721  TGGCCCAGCAGCTACACCCACAGCTCAGCATCTTCGACAGTCTTCTTTTGAGATACCTGA
     G   P   A   A   T   P   T   A   Q   H   L   R   Q   S   S   F   E   I   P   D
781  TGATGTACCTCTGCCAGCAGGTTGGGAGATGGCAAAGACATCTTCTGGTCAGAGATACTT
     D   V   P   L   P   A   G   W   E   M   A   K   T   S   S   G   Q   R   Y   F
841  CTTAAATCACATCGATCAGACAACAACATGGCAGGACCCCAGGAAGGCCATGCTGTCCCA
     L   N   H   I   D   Q   T   T   T   W   Q   D   P   R   K   A   M   L   S   Q
901  GATGAACGTCACAGCCCCCACCAGTCCACCAGTGCAGCAGAATATGATGAACTCGGCTTC
     M   N   V   T   A   P   T   S   P   P   V   Q   Q   N   M   M   N   S   A   S
961  AGCCATGAACCAGAGAATCAGTCAGAGTGCTCCAGTGAAACAGCCACCACCCCTGGCTCC
     A   M   N   Q   R   I   S   Q   S   A   P   V   K   Q   P   P   P   L   A   P
```

FIG. 7B

```
1021 CCAGAGCCCACAGGGAGGCGTCATGGGTGGCAGCAACTCCAACCAGCAGCAACAGATGCG
      Q  S  P  Q  G  G  V  M  G  G  S  N  S  N  Q  Q  Q  M  R
         •  •  •
1081 ACTGCAGCAACTGCAGATGGAGAAGGAGAGGCTGCGGCTGAAACAGCAAGAACTGCTTCG
      L  Q  Q  L  Q  M  E  K  E  R  L  R  L  K  Q  Q  E  L  L  R
1141 GCAGGTGAGGCCACAGGAGTTAGCCCTGCGTAGCCAGTTACCAACACTGGAGCAGGATGG
      Q  V  R  P  Q  E  L  A  L  R  S  Q  L  P  T  L  E  Q  D  G
1201 TGGGACTCAAAATCCAGTGTCTTCTCCCGGGATGTCTCAGGAATTGAGAACAATGACGAC
      G  T  Q  N  P  V  S  S  P  G  M  S  Q  E  L  R  T  M  T  T
1261 CAATAGCTCAGATCCTTTCCTTAACAGTGGCACCTATCACTCTCGAGATGAGAGTACAGA
      N  S  S  D  P  F  L  N  S  G  T  Y  H  S  R  D  E  S  T  D
1321 CAGTGGACTAAGCATGAGCAGCTACAGTGTCCCTCGAACCCCAGATGACTTCCTGAACAG
      S  G  L  S  M  S  S  Y  S  V  P  R  T  P  D  D  F  L  N  S
1381 TGTGGATGAGATGGATACAGGTGATACTATCAACCAAAGCACCCTGCCCTCACAGCAGAA
      V  D  E  M  D  T  G  D  T  I  N  Q  S  T  L  P  S  Q  Q  N
1441 CCGTTTCCCAGACTACCTTGAAGCCATTCCTGGGACAAATGTGGACCTTGGAACACTGGA
      R  F  P  D  Y  L  E  A  I  P  G  T  N  V  D  L  G  T  L  E
1501 AGGAGATGGAATGAACATAGAAGGAGAGGAGCTGATGCCAAGTCTGCAGGAAGCTTTGAG
      G  D  G  M  N  I  E  G  E  E  L  M  P  S  L  Q  E  A  L  S
1561 TTCTGACATCCTTAATGACATGGAGTCTGTTTTGGCTGCCACCAAGCTAGATAAAGAAAG
      S  D  I  L  N  D  M  E  S  V  L  A  A  T  K  L  D  K  E  S
1621 CTTTCTTACATGGTTATAGAGCCCTCAGGCAGACTGAATTCTAAATCTGTGAAGGATCTA
      F  L  T  W  L  *
1681 AGGAGACACATGCACCGGAAATTTCCATAAGCCAGTTGCAGTTTTCAGGCTAATACAGAA
1741 AAAGATGAACAAACGTCCAGCAAGATACTTTAATCCTCTATTTTGCTCTTCCTTGTCCAT
1801 TGCTGCTGTTAATGTATTGCTGACCTCTTTCACAGTTGGCTCTAAAGAATCAAAAGAAAA
1861 AAACTTTTTATTTCTTTTGCTATTAAAACTACTGTTCATTTTGGGGGCTGGGGGAAGTGA
1921 GCCTGTTTGGATGATGGATGCCATTCCTTTTGCCCAGTTAAATGTTCACCAATCATTTTA
1981 ACTAAATACTCAGACTTAGAAGTCAGATGCTTCATGTCACAGCATTTAGTTTGTTCAACA
2041 GTTGTTTCTTCAGCTTCCTTTGTCCAGTGGAAAAACATGATTTACTGGTCTGACAAGCCA
```

FIG.7C

```
2101 AAAATGTTATATCTGATATTAAATACTTAATGCTGATTTGAAGAGATAGCTGAAACCAAG
2161 GCTGAAGACTGTTTTACTTTCAGTATTTTCTTTTCCTCCTAGTGCTATCATTAGTCACAT
2221 AATGACCTTGATTTTATTTTAGGAGCTTATAAGGCATGAGACAATTTCCATATAAATATA
2281 TTAATTATTGCCACATACTCTAATATAGATTTTGGTGGATAATTTTGTGGGTGTGCATTT
2341 TGTTCTGTTTTGTTGGGTTTTTTGTTTTTTTGTTTTTGGCAGGGTCGGTGGGGGGGTTG
2401 GTTGGTTGGTTGGTTTTGTCGGAACCTAGGCAAATGACCATATTAGTGAATCTGTTAATA
2461 GTTGTAGCTTGGGATGGTTATTGTAGTTGTTTTGGTAAAATCTTCATTTCCTGGTTTTTT
2521 TTACCACCTTATTTAAATCTCGATTATCTGCTCTCTCTTTTATATACATACACACACCCA
2581 AACATAACATTTATAATAGTGTGGTAGTGGAATGTATCCTTTTTTAGGTTTCCCTGCTTT
2641 CCAGTTAATTTTTAAAATGGTAGCGCTTTGTATGCATTTAGAATACATGACTAGTAGTTT
2701 ATATTTCACTGGTAGTTTAAATCTGGTTGGGGCAGTCTGCAGATGTTTGAAGTAGTTTAG
2761 TGTTCTAGAAAGAGCTATTACTGTGGATAGTGCCTAGGGGAGTGCTCCACGCCCTCTGGG
2821 CATACGGTAGATATTATCTGATGAATTGGAAAGGAGCAAACCAGAAATGGCTTTATTTTC
2881 TCCCTTGGACTAATTTTTAAGTCTCGATTGGAAATCAGTGAGTAGGTTCATAATGTGCAT
2941 GACAGAAATAAGCTTTATAGTGGTTTACCTTCATTTAGCTTTGGAAGTTTTCTTTGCCTT
3001 AGTTTTGGAAGTAAATTCTAGTTTGTAGTTCTCATTTGTAATGAACACATTAACGACTAG
3061 ATTAAAATATTGCCTTCAAGATTGTTCTTACTTACAAGACTTGCTCCTACTTCTATGCTG
3121 AAAATTGACCCTGGATAGAATACTATAAGGTTTTGAGTTAGCTGGAAAAGTGATCAGATT
3181 AATAAATGTATATTGGTAGTTGAATTTAGCAAAGAAATAGAGATAATCATGATTATACCT
3241 TTATTTTTACAGGAAGAGATGATGTAACTAGAGTATGTGTCTACAGGAGTAATAATGGTT
3301 TCCAAAGAGTATTTTTTAAAGGAACAAAACGAGCATGAATTAACTCTTCAATATAAGCTA
3361 TGAAGTAATAGTTGGTTGTGAATTAAAGTGGCACCAGCTAGCACCTCTGTGTTTTAAGGG
3421 TCTTTCAATGTTTCTAGAATAAGCCCTTATTTTCAAGGGTTCATAACAGGCATAAAATCT
3481 CTTCTCCTGGCAAAAGCTGCTATGAAAAGCCTCAGCTTGGGAAGATAGATTTTTTTCCCC
3541 CCAATTACAAAATCTAAGTATTTTGGCCCTTCAATTTGGAGGAGGGCAAAAGTTGGAAGT
```

FIG. 7D

```
3601 AAGAAGTTTTATTTTAAGTACTTTCAGTGCTCAAAAAAATGCAATCACTGTGTTGTATAT
3661 AATAGTTCATAGGTTGATCACTCATAATAATTGACTCTAAGGCTTTTATTAAGAAAACAG
3721 CAGAAAGATTAAATCTTGAATTAAGTCTGGGGGGAAATGGCCACTGCAGATGGAGTTTTA
3781 GAGTAGTAATGAAATTCTACCTAGAATGCAAAATTGGGTATATGAATTACATAGCATGTT
3841 GTTGGGATTTTTTTTAATGTGCAGAAGATCAAAGCTACTTGGAAGGAGTGCCTATAATTT
3901 GCCAGTAGCCACAGATTAAGATTATATCTTATATATCAGCAGATTAGCTTTAGCTTAGGG
3961 GGAGGGTGGGAAAGTTTGGGGGGGGGGTTGTGAAGATTTAGGGGGACCTTGATAGAGAAC
4021 TTTATAAACTTCTTTCTCTTTAATAAAGACTTGTCTTACACCGTGCTGCCATTAAAGGCA
4081 GCTGTTCTAGAGTTTCAGTCACCTAAGTACACCCACAAAACAATATGAATATGGAGATCT
4141 TCCTTTACCCCTCAACTTTAATTTGCCCAGTTATACCTCAGTGTTGTAGCAGTACTGTGA
4201 TACCTGGCACAGTGCTTTGATCTTACGATGCCCTCTGTACTGACCTGAAGGAGACCTAAG
4261 AGTCCTTTCCCTTTTTGAGTTTGAATCATAGCCTTGATGTGGTCTCTTGTTTTATGTCCT
4321 TGTTCCTAATGTAAAAGTGCTTAACTGCTTCTTGGTTGTATTGGGTAGCATTGGGATAAG
4381 ATTTTAACTGGGTATTCTTGAATTGCTTTTACAATAAACCAATTTTATAATCTTTAAATT
4441 TATCAACTTTTTACATTTGTGTTATTTTCAGTCAGGGCTTCTTAGATCTACTTATGGTTG
4501 ATGGAGCACATTGATTTGGAGTTTCAGATCTTCCAAAGCACTATTTGTTGTAATAACTTT
4561 TCTAAATATAGTGCCTTTAAAGGAAAAATGAACACAGGGAAGTGACTTTGCTACAAATAA
4621 TGTTGCTGTGTTAAGTATTCATATTAAATACATGCCTTCTATATGGAACATGGCAGAAAG
4681 ACTGAAAAATAACAGTAATTAATTGTGTAATTCAGAATTCATACCAATCAGTGTTGAAAC
4741 TCAAACATTGCAAAGTGGGTGGCAATATTCAGTGCTTAACACTTTTCTAGCGTTGGTAC
4801 ATCTGAGAAATGAGTGCTCAGGTGGATTTTATCCTCGCAAGCATGTTGTTATAAGAATTG
4861 TGGGTGTGCCTATCATAACAATTGTTTTCTGTATCTTGAAAAGTATTCTCCACATTTTA
4921 AATGTTTTATATTAGAGAATTCTTTAATGCACACTTGTCAAATATATATATATAGTACCA
4981 ATGTTACCTTTTTATTTTTGTTTTAGATGTAAGAGCATGCTCATATGTTAGGTACTTAC
5041 ATAAATTGTTACATTATTTTTTCTTATGTAATACCTTTTTGTTTGTTTATGTGGTTCAAA
5101 TATATTCTTTCCTTAAAAAAAAAAAAAAAAAAAAAAAAAAAAAAAAAAAAA
```

FIG. 8

```
         1                                                               50
HYAP     MDPGQQPPPQ PAPQGQGQPP SQPPQGQGPP SGPGQPAPAA TQAAPQAPPA
MYAP     MEPAQQPPPQ PAPQGPA.PP SVSPAGTP.. .......... ..AAPPAPPA
YAP      MDPGQPQPQQ P.PQAAQPPA PQQAAPQPPG AGSGAPGGAA QPPGAGPPPA 51                                                              100
HYAP     GHQIVHVRGD SETDLEALFN AVMNPKTANV PQTVPMRLRK LPDSFFKPPE
MYAP     GHQVVHVRGD SETDLEALFN AVMNPKTANV PQTVPMRLRK LPDSFFKPPE
YAP      GHQIVHVRGD SETDLEALFN AVMNPKGANV PHTLPMRLRK LPDSFFKPPE 101                                                             150
HYAP     PKSHSRQAST DAGTAGALTP QHVRAHSSPA SLQLGAVSPG TLTPTGVVSG
MYAP     PKSHSRQAST DAGTAGALTP QHVRAHSSPA SLQLGAVSPG TLTASGVVSG
YAP      PKAHSRQAST DAGTAGALTP QHVRAHSSPA SLQLGAVSPG TLTPSGVVTG 151                                                             200
HYAP     PAATPTAQHL RQSSFEIPDD VPLPAGWEMA KTSSGQRYFL NHIDQTTTWQ
MYAP     PAAAPAAQHL RQSSFEIPDD VPLPAGWEMA KTSSGQRYFL NHNDQTTTWQ
YAP      P.GAPSSQHL RQSSFEIPDD VPLPPGWEMA KTPSGQRYFL NHIDQTTTWQ 201                                                             250
HYAP     DPRKAMLSQM NVTAPTSPPV QQNMMNSAS. .......... ..........
MYAP     DPRKAMLSQL NVPAPASPAV PQTLMNSASG PLPDGWEQAM TQDGEVYYIN
YAP      DPRKAMLSQM NVTAPTSPPV QQNLMNSAS. .......... ..........

251                                                             300
HYAP     .......... .......AMN QRISQSAPVK QPPPLAPQSP QGGVMGGSNS
MYAP     HKNKTTSWLD PRLDPRFAMN QRITQSAPVK QPPPLAPQSP QGGVLGGGSS
YAP      .......... .......AMN QRISQSAPVK QPPPLAPQSP QGGVMGGSSS
                                ##############

301                                                             350
HYAP     NQQQQMRLQQ LQMEKERLRL KQQELLRQVR PQELALRSQL PTLEQDGGTQ
MYAP     NQQQQIQLQQ LQMEKERLRL KQQELFR... .QELALRSQL PTLEQDGGTP
YAP      NQQQQMRLQQ LQMEKERLRL KHQELLR... .QELALRSQL PTMEQDGGSQ 351                                                             400
HYAP     NPVSSPGMSQ ELRTMTTNSS DPFLNSGTYH SRDESTDSGL SMSSYSVPRT
MYAP     NAVSSPGMSQ ELRTMTTNSS DPFLNSGTYH SRDESTDSGL SMSSYSIPRT
YAP      NPVSSPGMSQ ELRTMTTNSS DPFLNSGTYH SRDESTDSGL SMSSYSVPRT 401                                                             450
HYAP     PDDFLNSVDE MDTGDTINQS TLPSQQNRFP DYLEAIPGTN VDLGTLEGDG
MYAP     PDDFLNSVDE MDTGDTISQS TLPSQQSRFP DYLEALPGTN VDLGTLEGDA
YAP      PDDFLNSVDE MDTGDSISQS NIPSHQNRFP DYLEAIPGTN VDLGTLEGDG 451                                             493
HYAP     MNIEGEELMP SLQEALSSDI LNDMESVLAA TKLDKESFLTWL*
MYAP     MNIEGEELMP SLQEALSSEI L.DVESVLAA TKLDKESFLTWL*
YAP      MNIEGEELMP SLQEALSSDI LNDMESVLAA TKPDKESFLTWL*
```

FIG. 12

| Protein/Species | Position | Sequences of the WW Domains | Accession # |
|---|---|---|---|
| Dmd/Human | 3052 | TSVQGPWERAISPN.KVPYYINHETQTTCWDHPKMTELY | P11532 |
| Dmd/Ray | 253 | TSVQGPWERAISPN.KVPYYINHQTQTTCWDHPKMTELY | M37645 |
| Utro/Human | 2813 | TSVQLPWQRSISHN.KVPYYINHQTQTTCWDHPKMTELF | X69086 |
| Yap/Human | 171 | VPLPAGWEMAKTSS.GQRYFLNHIDQTTTWQDPRKAMLS | X80507 |
| Yap/Chick | 169 | VPLPPGWEMAKTPS.GQRYFLNHIDQTTTWQDPRKAMLS | X76483 |
| Yap/Mouse-1 | 151 | VPLPAGWEMAKTSS.GQRYFLNHNDQTTTWQDPRKAMLS | X80508 |
| Yap/Mouse-2 | 218 | GPLPDGWEQAMTQD.GEVYYINHKNKTTSWLDPRLDPRF | X80508 |
| Nedd4/Mouse-1 | ? | SPLPPGWEERQDVL.GRTYYVNHESRRTQWKRPSPDDDL | D10714 |
| Nedd4/Mouse-2 | ? | SGLPPGWEEKQDDR.GRSYYVDHNSKTTTWSKPTMQDDP | D10714 |
| Nedd4/Mouse-3 | ? | GPLPPGWEERTHTD.GRVFFINHNIKKTQWEDPRLQNVA | D10714 |
| Rsp5/Yeast-1 | 228 | GRLPPGWERRTDNF.GRTYYVDHNTRTTTWKRPTLDQTE | L11119 |
| Rsp5/Yeast-2 | 331 | GELPSGWEQRFTPE.GRAYFVDHNTRTTTWVDPRRQQYI | L11119 |
| Rsp5/Yeast-3 | 387 | GPLPSGWEMRLTNT.ARVYFVDHNTKTTTWDDPRLPSSL | L11119 |
| Ykb2/Yeast-1 | 1 | M..SIWKEAKDAS.GRIYYYNTLTKKSTWEKPKELISQ | P33203 |
| Ykb2/Yeast-2 | 39 | LLRENGWKAAKTAD.GKVYYYNPTTRETSWTIAFEKKVE | P33203 |
| Yo61/Caeel-1 | 49 | PSVESDWSVHTNEK.GTPYYHNRVTKQTSWIKPDVLKTP | P34600 |
| Yo61/Caeel-2 | 94 | QPQQGQWKEFMSDD.GKPYYYNTLTKKTQWVKPDGEEIT | P34600 |
| Amoe/Amoeba | ? | KMSVDGWSQYFTAE.GNAYYYNEVSGETSWDPPSSLQSH | D90360 |
| FE65/Rat | 12 | SDLPAGWMRVQDTS.GTYYWHIP.TGTTQWEPPGRASPS | X60468 |
| Ess1/Yeast | 29 | TGLPTPWTARYSKSKKREYFFNPETKHSQWEEPEGTNKD | P22696 |

Consensus Line:    LPtGWE    ttt  Gt  YYhNH  TtTTtW  tPt    t

Secondary Structure:  111111    eee    1111  eeeee  1111    111111111

SH3 KINASE DOMAIN ASSOCIATED PROTEIN, A SIGNALLING DOMAIN THEREIN, NUCLEIC ACIDS ENCODING THE PROTEIN AND THE DOMAIN, AND DIAGNOSTIC AND THERAPEUTIC USES THEREOF

The research leading to the present invention was supported in part with Grant No. CA51083 from the National Institutes of Health, and Grant Nos. CA45757 and CA01605 from the National Cancer Institute. Accordingly, the Government may have certain rights in the invention.

FIELD OF THE INVENTION

The present invention relates to regulation and control of cellular processes by SH3-domain binding proteins, by putative signalling domains of such proteins, ligands of the signalling domain, and diagnosis and therapy based on the activity of such proteins, signalling domains, and ligands.

BACKGROUND OF THE INVENTION

Protein—protein interaction is one of the mechanisms of signal transduction processes. One such process involves non-receptor type protein-tyrosine kinases (PTKs) of the Src family, which signal in normal and transformed cells. In recent years, much of the attention has been concentrated on certain specific regions of PTKs, in particular three structural domains, termed SH2 (SH stands for Src homology), SH3, and PH (pleckstrin homology). In addition to the Src family of proteins, these domains are present in a wide variety of proteins implicated in signal transduction processes.

The yes proto-oncogene encodes a member of the Src family of non-receptor type protein tyrosine kinases (PTKs) (Cooper, 1990; Sudol, 1993). The Src family kinases have been implicated in signal transduction processes because they physically associate with certain membrane receptors and functionally respond to the binding of cognate ligands or receptor crosslinking (Bolen, 1991). The functional response of receptor-associated PTKs is usually manifested by an increase in tyrosine phosphorylation of cellular proteins (Bolen, 1991). The Yes protein kinase was shown to be functionally associated with platelet-derived growth factor receptor in fibroblasts Kypta et al., 1990), with glycoprotein IV (CD36) in platelets (Huang et al., 1991), and with the high-affinity IgE receptor in mast cells (Eiseman & Bolen, 1992), but further signaling steps through these complexes are not known.

Another clue pointing to the involvement of the Src family of PTKs in signaling processes comes from the identification of structural domains, termed SH2 and SH3 (SH for Src homology), which are present in the amino-terminal half of Src family members and are also found in a wide variety of proteins implicated in signal transduction processes (Margolis, 1992; Pawson & Gish, 1992). The SH2 domains are known to interact specifically with phosphotyrosine-containing proteins (Pawson & Gish, 1992; Birge & Hanafusa, 1993; Pawson & Schlessinger, 1993) and the resulting complexes are involved in signal transduction events initiated by PTKs (Cantley et al., 1991). The SH2 domain of Src PTKs is involved in substrate recognition and in the regulation of kinase activity by maintaining a repressed conformation of PTKs (Kanner et al., 1991; Roussel et al., 1991). The precise role of SH3 domains in signal transduction has yet to be completely elucidated (Musacchio et al., 1992a; Mayer & Baltimore, 1993; Pawson & Schlessinger, 1993) but the accumulating genetic, biochemical, and structural data implicate these domains in mediating noncovalent protein-protein interactions essential for cellular and intercellular signaling (Clark et al., 1992; Musacchio et al., 1992b; Yu et al., 1992; Booker et al., 1993; Kohda et al., 1993; Koyama et al., 1993; Li et al., 1993; Noble et al., 1993; Rozakis-Adcock et al., 1993; Ren et al., 1994; Feller et al., 1994). Studies with the SH3 domains of the Ab1 kinase and the Grb2 adaptor protein identified a 10 amino acid long proline-rich motifs that are present in the proteins that bind to the SH3 domains and mediate the protein—protein interaction (Cicchetti et al., 1992; Li et al., 1993; Ren et al., 1993; Rozakis-Adcock et al., 1993; Williamson, 1994; Yu et al., 1994). For Src and other members of the family, it is presumed that binding of specific proteins to their SH3 domains may result in the modulation of their enzymatic activity and thus could be a part of the signaling mechanism by cellular and oncogenic forms of the Src Emily PTKs (Kato et al., 1986; Potts et al., 1988; Nemeth et al., 1989; Hirai & Varmus, 1990; Seidel-Dugan et al., 1992; Wages et al., 1992; Cooper & Howell, 1993; Liu et al., 1993). It has also been reported that SH3 domains of Src PTKs interact with substrates (Kanner et al., 1991; Seidel-Dugan et al., 1992; Liu et al., 1993) and with other signaling molecules including unknown serine and/or threonine kinases (Weng et al., 1993).

Our functional studies of the Yes proto-oncogene started with the generation of polyclonal antibodies directed to the bacterially expressed fusion protein corresponding to the unique and SH3 domains of Yes (Sudol & Hanafusa, 1986). Interestingly, the resulting antibody showed strong immunoreactivity with the SH3 domain and weaker reaction with the unique domain. Based on this observation we used the original anti-Yes IgG to generate polyclonal anti-idiotypic antibodies (Jerne, 1974) expecting a reagent that would mimic a conformation of the SH3 domain of Yes and would allow us to isolate Yes binding proteins.

We report here the identification, characterization, and cDNA cloning, of a novel protein that binds to the SH3 domain of the Yes proto-oncogene product. Anti-idiotypic antibodies were used to identify the protein and to clone its cDNA from an expression library. The presence of serine phosphorylation along with a proline-rich motif involved in SH3 binding implicates YAP65 in signaling processes. It is possible that interaction between Yes and YAP65 represents a novel link between pathways transduced by protein-tyrosine and serine kinases.

A novel Yes-associated protein (YAP) of 65 kDa was identified in chicken by one of the inventors herein (Sudol, 1994, "Yes-associated protein (YAP65) is a proline-rich phosphoprotein that binds to the SH3 domain of the Yes proto-oncogene product," Oncogene 9:2145–52, which is incorporated herein by reference in its entirety, and which corresponds to the first Example disclosed infra).

References cited herein only by author and year are listed at the end of the specification, after the last example. The citation of any reference herein is not an admission that such reference is available as prior art to the instant invention.

SUMMARY OF THE INVENTION

In broadest aspect, the present invention relates to proteins and polypeptides that are involved with intracellular signal transduction. In particular, the invention provides a novel polypeptide domain that appears to be involved in signalling. Accordingly, the invention further provides nucleic acids, particularly DNA molecules, encoding such proteins and polypeptides. The invention further relates to modulation of intracellular signal transduction by inducing or inhibiting the activity of the proteins and polypeptides of the invention.

In a first aspect, the invention provides an isolated nucleic acid molecule, which is hybridizable to a DNA molecule (or its complement) that has a nucleotide sequence shown in FIG. 2 (SEQ ID NO:1), or the sequence complementary thereto; or that has a nucleotide sequence shown in FIG. 7 (SEQ ID NO:3), or the sequence complementary thereto; or that encodes a Yes proto-oncogene associated protein or polypeptide (YAP). The YAP protein or polypeptide of the invention is characterized by binding to the Src homology domain 3 (SH3), containing a proline-rich motif that is involved in binding between YAP and Yes kinase, containing a WW domain polypeptide, and being phosphorylated in vivo on serine.

The WW domain, which is a unique domain advantageously characterized herein, has from 30 to 50 amino acid residues; has a consensus sequence:

LPtGWEXXXttt-Gt-YYhNH-TtTTtWNtPtNNt, wherein capitals indicate conserved amino acids, and boldface indicates the highly conserved tryptophan residues characteristic of the domain, h indicates a hydrophobic amino acid residue; t indicates a turn-like or polar amino acid residue; N indicates any amino acid; and a hyphen (-) indicates either no amino acid residue or any amino acid residue; and has a predicted secondary structure using a computer-assisted structural assignment program having the parameters characteristic of the PHD secondary structure prediction program as follows: loop-unassigned-beta strand-unassigned-loop-unassigned-beta strand-unassigned-loop-unassigned-loop, wherein the highly conserved tryptophan residues are located in the first and fifth unassigned segments.

In a further embodiment, the nucleic acid of the invention hybridizes to a DNA molecule that encodes a YAP protein or polypeptide having an amino acid sequence selected from the group consisting of the amino acid sequence of chicken YAP in FIG. 2 (SEQ ID NO:2), human YAP in FIG. 7 (SEQ ID NO:4), or murine YAP in FIG. 8 (SEQ ID NO:5), or the sequence complementary thereto. In specific embodiments, the nucleic acid molecule encodes a protein or polypeptide having an amino acid sequence selected from the group consisting of the amino acid sequence of chicken YAP in FIG. 2 (SEQ ID NO:2), human YAP in FIG. 7 (SEQ ID NO:4), or murine YAP in FIG. 8 (SEQ ID NO:5).

In another embodiment, the nucleic acid molecule encodes a protein or polypeptide fragment, which protein or polypeptide fragment is functionally active. In particular, the functional activity of the protein or polypeptide is selected from the group consisting of binding to an SH3 domain, binding to an approximately 40 kDa intracellular ligand, binding to a dystrophin-associated protein, regulation of binding of β-dystroglycan to dystrophin, and modulation of intracellular signalling.

The invention is especially directed to the nucleic acid molecule encoding a YAP fragment, wherein the protein or polypeptide fragment is the WW domain; however, with the exception of the novel YAP proteins of the invention, the nucleic acid molecule of the invention does not encode a full length, naturally occurring protein that includes a WW domain. Moreover, the invention broadly provides a nucleic acid molecule which encodes a WW domain polypeptide, which WW domain polypeptide is characterized as described above. In specific embodiments, the WW domain polypeptide has an amino acid sequence selected from the group consisting of SEQ ID NOS:6–25. In a specific embodiment, infra, the nucleic acid molecule encoding the WW domain polypeptide encodes a chimeric polypeptide.

Naturally, in addition to the nucleic acids of the invention, the invention further provides a cloning vector comprising the nucleic acid molecule encoding a YAP, or a functionally active fragment thereof, and a cloning vector encoding a WW domain polypeptide, as well as a host cell, in particular a bacterial host cell, harboring such a cloning vector. Similarly, the invention provides an expression vector comprising the nucleic acid molecule encoding a YAP protein or polypeptide or fragment thereof, or a WW domain polypeptide, operatively associated with an expression control sequence, as well as host cells, such as bacteria, yeast, insect cells, or mammalian cells, harboring such expression vectors.

The invention further extends to a method for producing a YAP protein or polypeptide, comprising culturing the host cell harboring the expression vector encoding a YAP protein or polypeptide, or fragment thereof, under conditions that allow for expression of the YAP protein or polypeptide; and recovering the expressed YAP protein or polypeptide. Similarly, the invention relates to a method for producing a WW domain polypeptide comprising culturing the host cell harboring the expression vector encoding the WW domain polypeptide under conditions that allow for expression of the WW domain polypeptide; and recovering the expressed WW domain polypeptide. In specific examples, infra, the WW domain polypeptide is expressed as a GST-fusion protein.

In a further aspect, the invention provides an isolated Yes proto-oncogene associated protein or polypeptide (YAP), or functionally active fragment thereof, which protein or polypeptide binds to the Src homology domain 3 (SH3), contains a proline-rich motif that is involved in binding between YAP and Yes kinase, contains a WW domain, and is phosphorylated in vivo on serine. The functional activity of the fragment is selected from the group consisting of binding to an SH3 domain, binding to an approximately 40 kDa intracellular ligand, binding to a dystrophin-associated protein, regulation of binding of β-dystroglycan to dystrophin, and modulation of intracellular signalling.

In specific embodiments, infra, the protein has an amino acid sequence selected from the group consisting of the amino acid sequence of chicken YAP in FIG. 2 (SEQ ID NO:2), human YAP in FIG. 7 (SEQ ID NO:4), or murine YAP in FIG. 8 (SEQ ID NO:5).

The invention further relates to a WW domain polypeptide, as characterized above. After identification of the WW domain, based on the observation that this domain is repeated in murine YAP, it was discovered that this domain can be found in other known, naturally occurring proteins. Accordingly, the present invention relates to the WW domain isolated from such naturally occurring proteins, whether by chemical synthesis, proteolysis of full length natural protein, or recombinant technology. Thus, according to the invention, that the WW domain polypeptide is not a naturally occurring full length protein (with the exception of the novel YAP proteins of the invention). In specific embodiments, the WW domain polypeptide has an amino acid sequence selected from the group consisting of SEQ ID NOS:6–25. In a specific embodiment, the WW domain polypeptide is labeled. In another specific embodiment, the WW domain polypeptide is a chimeric polypeptide. In particular, the protein can be a GST-chimeric protein.

In addition to proteins, the invention extends to an antibody that binds to the protein or polypeptide of the invention. Such antibodies may be polyclonal or monoclonal, and are intended to include single chain, Fv fragments, F(ab) fragments, chimeric antibodies, humanized antibodies, bacterially expressed antibodies, etc. In a specific embodiment, the antibody can inhibit the functional activity of the protein or polypeptide.

It has been discovered that the WW domain interacts with a proteinaceous ligand in the cytoplasm. This ligand has been identified by "Western" analysis (using labeled WW domain) as having an approximate molecular weight of 35–36 kDa. cDNAs encoding the ligand have also been identified, and the partial sequence information indicates that the ligand does not have any significant similarity with protein sequences available on Genbank.

Accordingly, the invention is further directed to a method for identifying a ligand of a WW domain polypeptide, comprising contacting candidate ligands with the WW domain polypeptide, detecting binding of the WW domain polypeptide with a ligand; and determining the structure of the ligand. The invention naturally relates to the ligand identified by this method, and as characterized above.

The invention also relates to a method for identifying a nucleic acid encoding a ligand of the WW domain polypeptide comprising contacting cells transformed with candidate DNA believed to encode a ligand of the WW domain polypeptide with the WW domain polypeptide; detecting binding of the WW domain polypeptide with a ligand expressed by the transformed cells; selecting transformed cells in which binding of the WW domain polypeptide is detected; and determining the structure of a nucleic acid in the selected cells which corresponds to the transforming DNA which encodes the ligand. Accordingly, the invention further relates to the nucleic acid encoding a ligand of the WW domain polypeptide identified according to the method of claim 42.

The proteins and polypeptides of the invention, and nucleic acids encoding the same, are useful for diagnosis and therapy of a disease or disorder associated with a defect in intracellular signal transduction. For example, the invention relates to a method for treating a disease or disorder associated with a defect in intracellular signal transduction comprising administering an amount of the YAP protein or polypeptide, or a WW domain polypeptide, into cells of a subject believed to be suffering from a disease or disorder associated with a defect in intracellular signal transduction. Alternatively, the invention relates to introducing an expression vector that expresses the YAP protein or polypeptide, or functionally active fragment thereof, or a WW domain polypeptide, into cells of a subject believed to be suffering from a disease or disorder associated with a defect in intracellular signal transduction, wherein the expression control sequence of the expression vector provides for expression in the cell. In a specific embodiment, the disease or disorder is muscular dystrophy.

Conversely, the present invention contemplates inhibiting the YAP protein or WW domain polypeptide, e.g., to decrease cellular activation associated with intracellular signalling. Such therapy may be important in the treatment of certain cancers and tumors. Inhibition can be achieved with neutralizing antibodies, by gene knockout, with antisense nucleic acids, and the use of small molecule antagonists (e.g., a competitive inhibitor such as PVKQPPPLAP (SEQ ID NO:26).

Thus, it is a primary object of the present invention to provide factors for modulation of intracellular signal transduction.

It is a further object of the invention to provide modulators of SH3-mediated signal transduction.

A corollary object of the invention is to inhibit or reverse oncogenic transformation of a cell by inhibiting the signal transduction pathway within the cell.

It is another object of the invention to provide modulators of signal transduction mediated by dystrophyn and dystrophin-binding proteins.

A related object is to treat a disease or disorder associated with an impairment of signal transduction mediated by dystrophin or dystrophin-binding proteins.

These and other objects of the present invention can be better appreciated and understood by reference to the following drawings and detailed description of the invention.

Figure 6A:
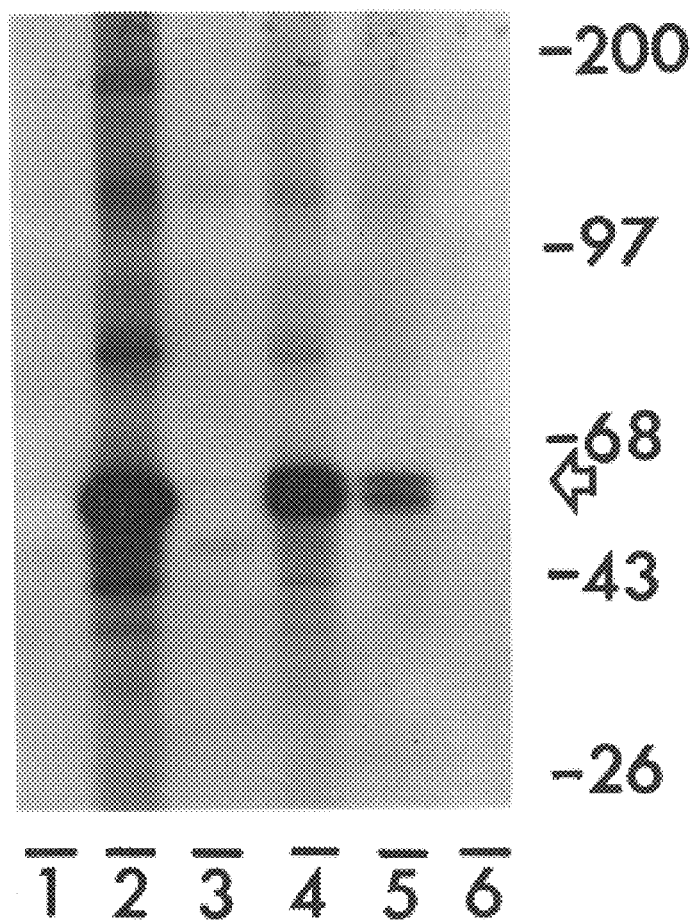
Figure 6B:
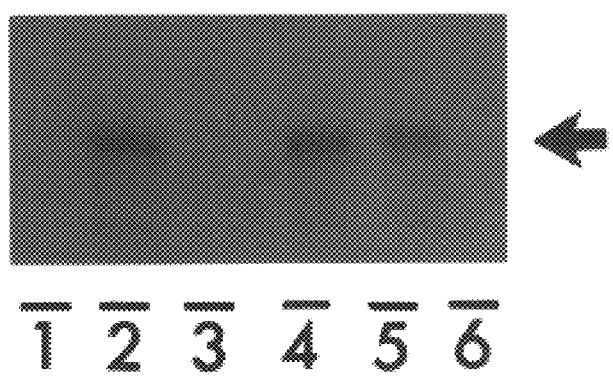

FIG. 6. Coprecipitation of Yes kinase with YAP65 coupled to Sepharose. (A) Lysates of CEFs were immunoprecipitated with anti-Yes IgG (2) or with YAP65-Sepharose (4,5,6) and subjected to an immune complex kinase assay. Preimmune IgG—lane 1; Sepharose-4B—lane 3. Lane 5 is immunoprecipitation with YAP65-Sepharose in the presence of 2 μM of GST-Yes-SH3 fusion protein; lane 6, in the presence of 10 μM of the GST-Yes-SH3 protein. The precipitated kinase activity shown in A may also be due to other kinases, in addition to Yes; we have shown here that in vitro YAP65 interacts with the SH3 domain of Src. The doublet of bands observed in the results of kinase assays, lanes 4 and 5, is characteristic for Yes kinase (for discussion see Sudol & Hanafusa, 1986). (B) Western blot analysis of samples shown in (A). Proteins transferred to nitrocellulose were probed with anti-Yes IgG and $^{128}$I-labeled protein A. Open arrow indicates products of the in vitro kinase assay. Solid arrow indicates the Yes protein.

FIG. 7. Nucleotide and deduced amino acid sequences of human YAP. The 5154-base pair human YAP cDNA encodes 493 amino acids and is terminated at nucleotide 1638 marked by an asterisk. A putative protein domain, termed the WW domain, is underlined. A proline-rich sequence implicated in binding between YAP and various SH3 domains is indicated with black dots.

FIG. 8. Alignment of the human (HYAP), mouse (MYAP) and chicken (YAP) YAP amino acid sequences. Positions that differ in at least one amino acid are indicated in bold. Spaces in the alignment were introduced arbitrarily and are indicated with dots. The sequences corresponding to the putative WW domain are underlined. Note that in MYAP a second WW domain is present. Proline-rich sequences implicated in binding between YAP and various SH3 domains are conserved and indicated with #.

Figure 9:
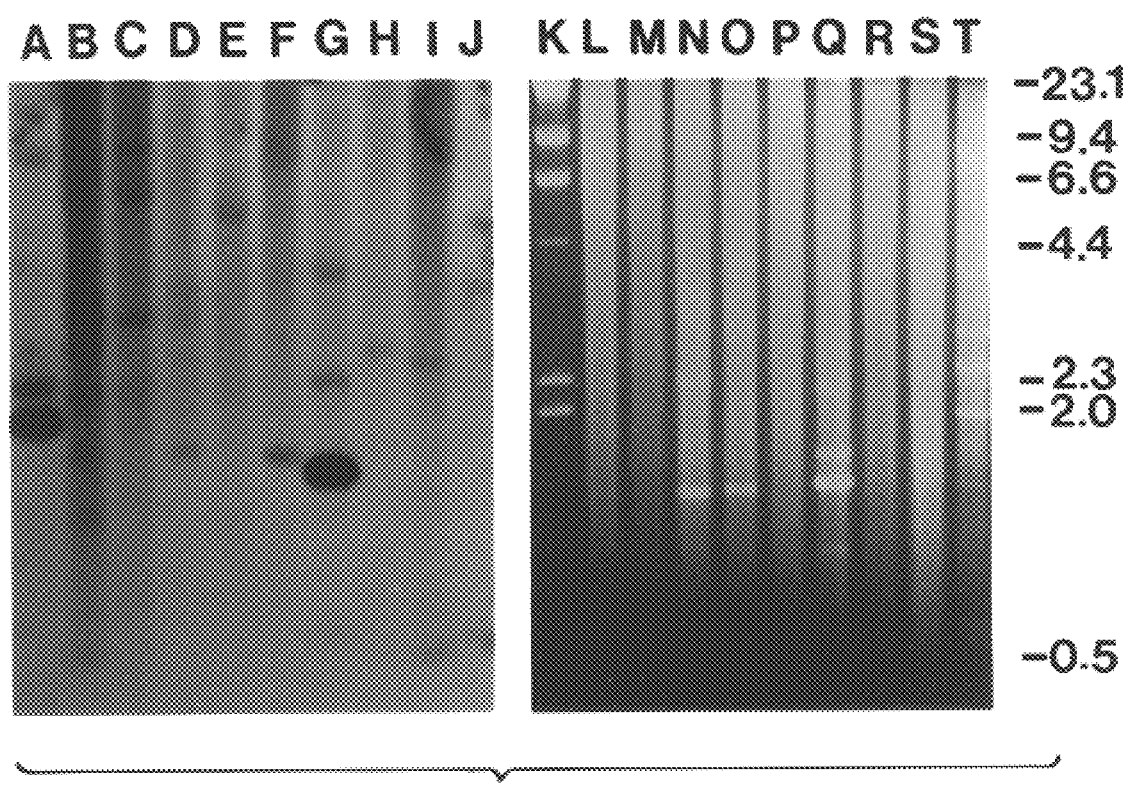

FIG. 9. Southern blot analysis of genomic DNA from nine eucaryotic species. Genomic DNA (4 μg) was digested with EcoRI, resolved in 0.7% agarose gel, transferred to a charge-modified nylon membrane by blotting and fixed by UV irradiation. The DNA corresponding to the entire coding region of the HYAP cDNA was used as a probe. Left Panel (A–J) represents results of hybridization with the HYAP cDNA probe, Right Panel (K–T) shows results of staining the agarose gel with ethidium bromide to check for even DNA loading and clear satellite bands. Lanes A,K contain lambda HindIII DNA markers with sizes indicated in kilobases. Lanes B, L contain human; C,M monkey; D,N rat; E,O mouse; F,P dog; G,Q cow; H,R rabbit; I,S chicken and J,T yeast DNA. The exposure time was four days.

Figure 10:
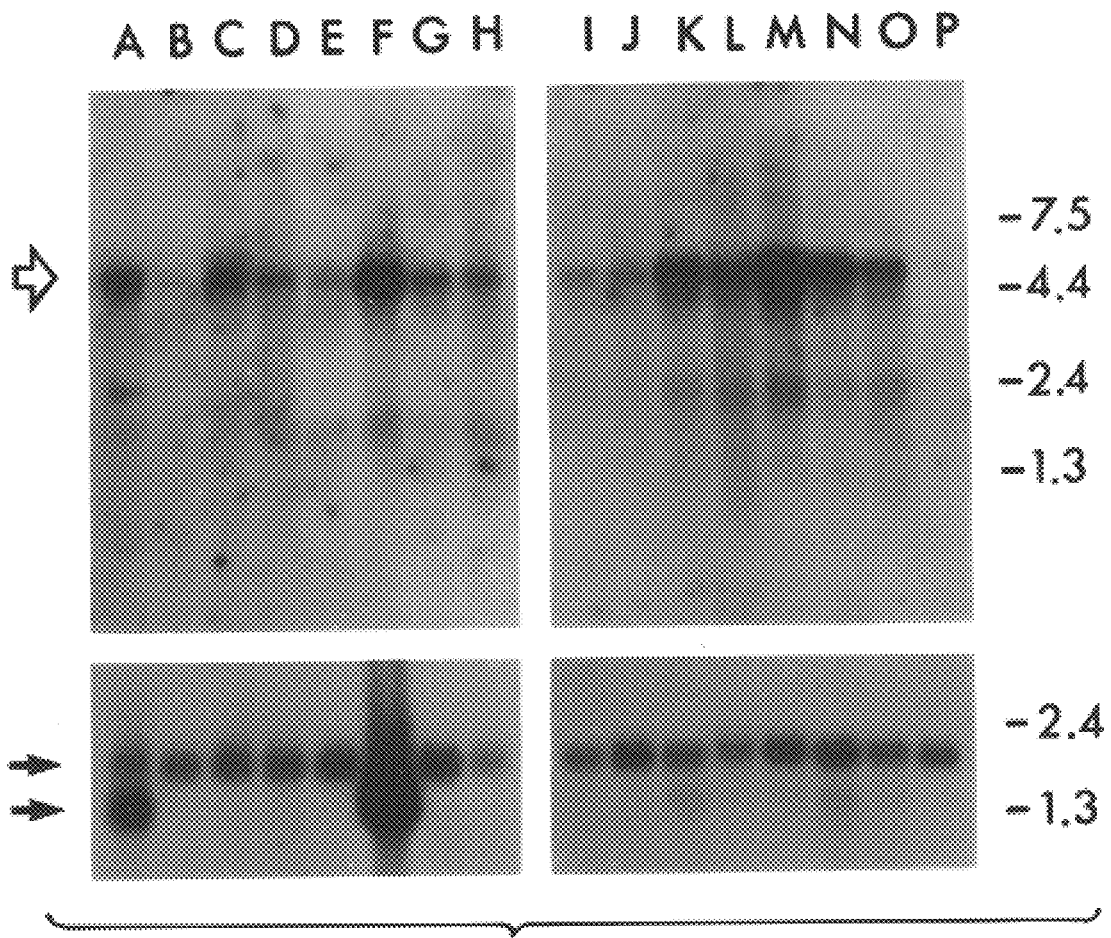

FIG. 10. Northern blot analysis of poly A$^+$ RNA from sixteen different human tissues. Poly A$^+$RNAs (2 μg each) from adult human tissues were run on a denaturing formaldehyde 1.2% agarose gel, transferred to a charge-modified nylon membrane by blotting and fixed by UV irradiation. The radiolabeled cDNA corresponding to the entire coding region of the HYAP was used as a probe (Upper Panel). For normalization and to ensure the intactness of the RNA the blot was hybridized with a radiolabeled cDNA encoding human beta-actin (Lower Panel). Lane A, heart; B, brain; C, placenta; D, lung; E, liver; F, skeletal muscle; G, kidney; H, pancreas; I, spleen; J, thymus; K, prostate; L, testis; M, ovary; N, small intestine; O, colon; P, peripheral blood leukocytes. An open arrow indicates HYAP mRNA. Two arrows indicate beta actin mRNAs. Note that heart and skeletal muscle and to lesser degree prostate and small intestine contain an extra form of beta-actin mRNA that is of 1.6–1.8 kb. The exposure times were three days for HYAP, and 2 hours for beta-actin.

YAP65 cDNA detects loci on human chromosomes 11 and 6. DNA (~10 μg/lane) from human (lane 1), hamster-human hybrid 7300 with human chromosomes 6, 8, 11 and X (lane 2), mouse-human hybrid N9 with chromosomes 6, 7, partial 17, and 21 (lane 3), hamster-human hybrid 10095 with a der 9 chromosome (9pter->9q34::Xq13->Xqter) (lane 4), mouse-human hybrid G5 with 6,10,12, 20, and X (lane 5), hamster-human hybrid 7298 with 4, 14, 20, 21 and t(X;11) (Xqter->cen->11qter) (lane 6) and mouse (lane 7) was cleaved with restriction enzyme SstI, electrophoresed, transferred to filter and hybridized to radiolabeled YAP65 cDNA probe. Hybrids with a four or five number designation are from the Coriell Institute.

Figure 11A:
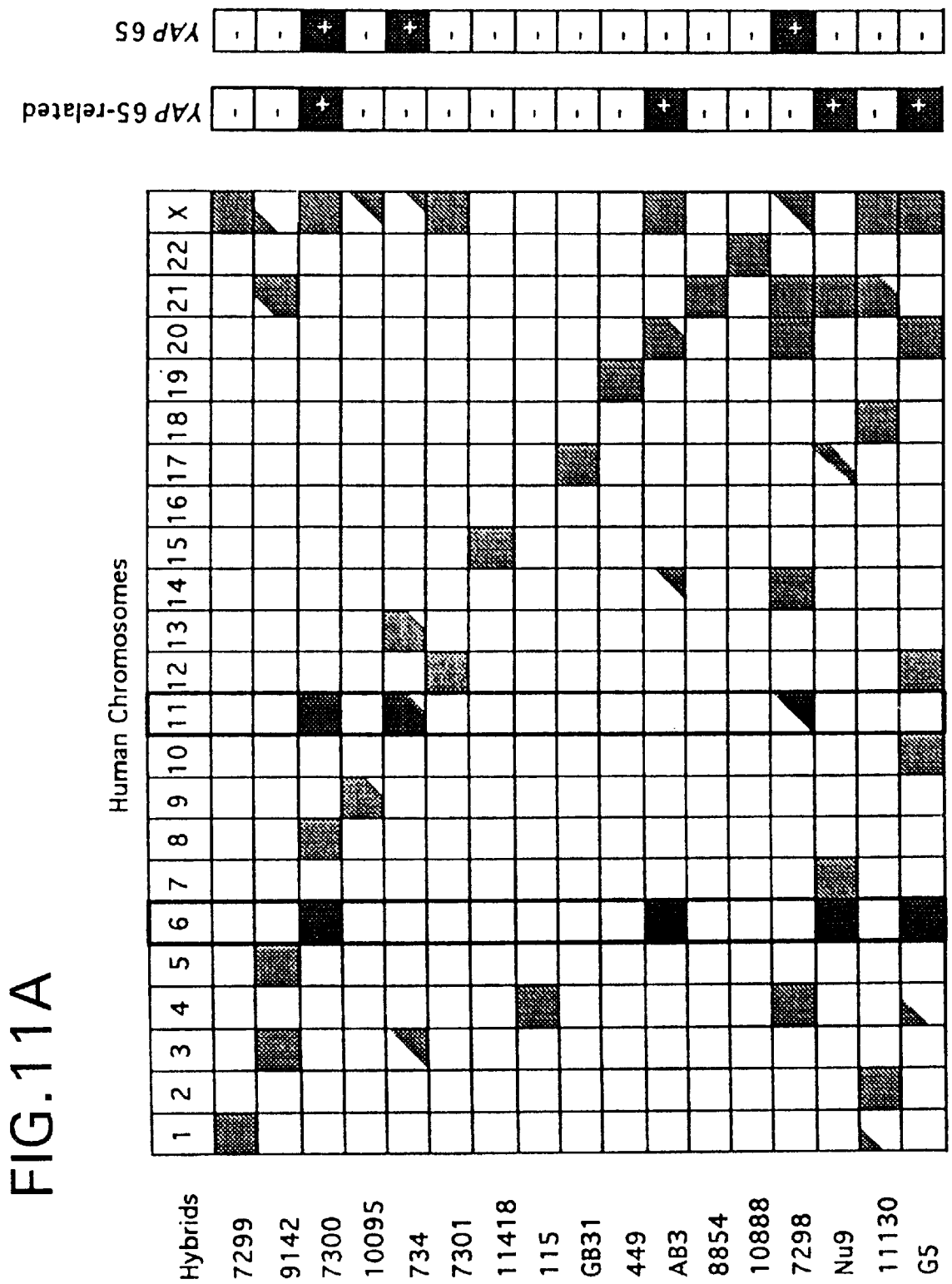
Figure 11B:
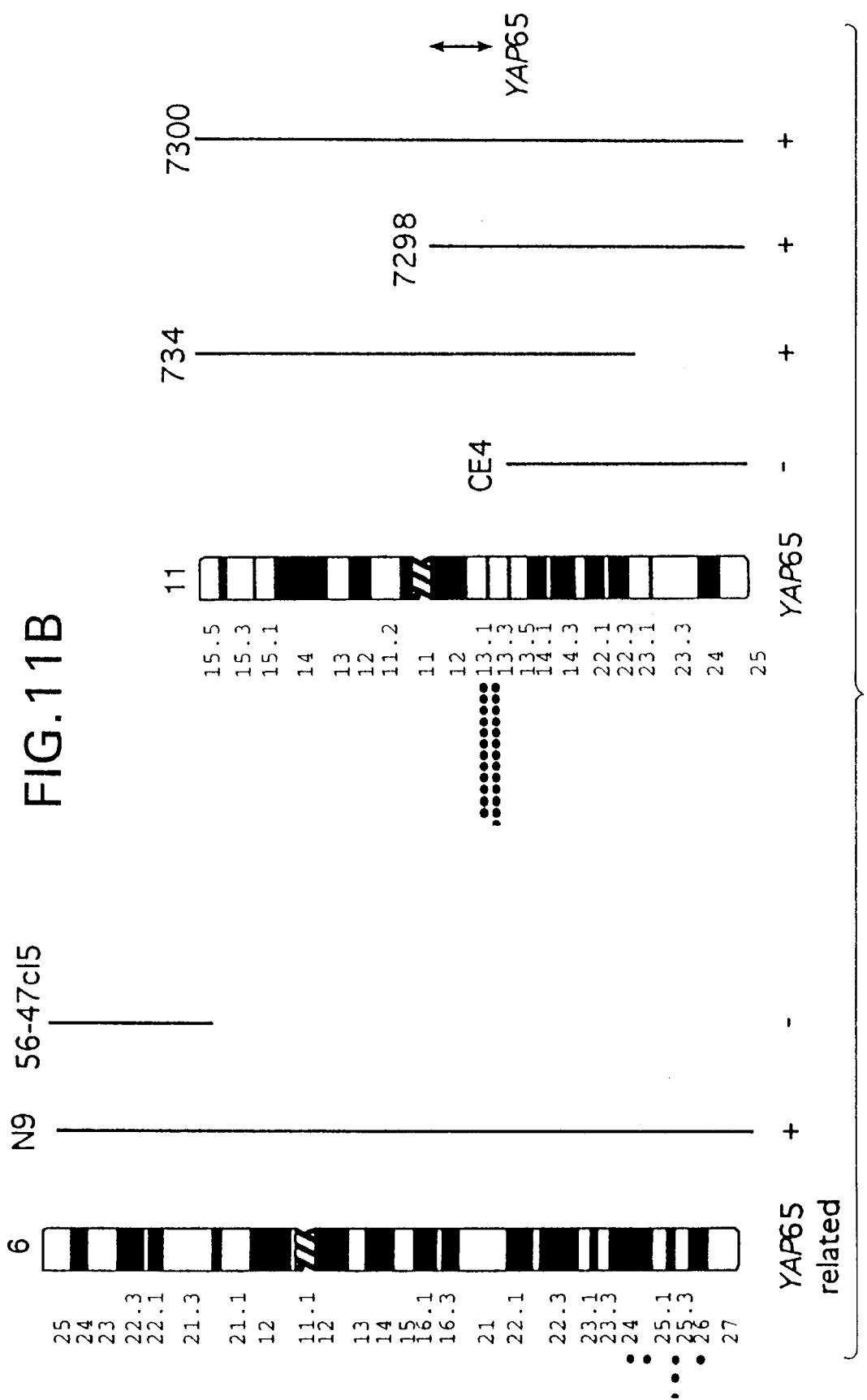

FIG. 11. Chromosomal localization of the HYAP gene. (A) Presence of the YAP65 loci in a panel of 17 rodent-human hybrids. DNA (10 μg) from various rodent-human hybrids was cleaved with restriction enzyme SstI, electrophoresed, transferred to nitrocellulose filter and hybridized to radiolabeled HYAP cDNA probe. ■ indicates that the hybrid named in the left column contains the chromosome indicated in the upper row; ◢ indicates presence of the long arm of the chromosome 9 or part of the long arm represented by a smaller fraction of stippling); ◸ indicates presence of the short arm (or partial short arm) of the chromosome; □ indicates the absence of the chromosome listed above the column. The column of chromosomes 6 and 11 are boldly outlined and stippled to highlight correlation of the presence of these chromosomes (or region of the chromosomes) with the presence of the YAP65 loci. The patterns of retention of the loci in the panel are shown to the right of the figure where presence of a locus in a hybrid is indicated by a stippled box with a plus sign and absence of a locus indicated by an open box enclosing a minus sign. (B). Regional chromosomal localization of YAP65 loci. Chromosome 6: the portion of chromosome 6 present in specific hybrids is represented by the solid line to the right of the chromosome 6 idiogram. Hybrids were tested by filter hybridization as described in the Methods section. Presence or absence of the YAP65-related locus is indicated below the lines representing individual hybrids. The YAP65-related locus was present only in hybrids which retained chromosome region 6p21-6qter in common. Results of fluorescent in situ hybridization (FISH) to normal human metaphases is illustrated to the left of the chromosome 6 idiogram where each filled circle represents five 10 fluorescent signals. Chromosome 11: hybrids carrying partial fragments of chromosome 11 are illustrated to the right of the chromosome 11 idiogram with results of filter hybridization to the YAP65 cDNA shown below the lines representing hybrids; the YAP65 cognate locus is present only in hybrids which retain 11cen->11q13 in common. Hybrid CE4 retains a der 14 (14pter->14q32::11ql3->11qter) from a B cell leukemia with a break in the BCL1 major breakpoint region and is negative for the YAP65 locus. Thus, the YAP65 gene is centromeric to the BCL1/CCND1 locus. Results of FISH on normal human metaphases is illustrated to the left of the chromosome 11 idiogram where each filled circle represents two fluorescent signals. Idiograms are from "Idiogram Albums" and are used with permission of Dr. David Adler, Dept. of Pathology, University of Washington.

FIG. 12. Modular architecture of the proteins containing the WW domain. Dashed lines denote partial sequence. Note that the 24 spectrin repeats of dystrophone are not drawn to scale.

Figure 13:
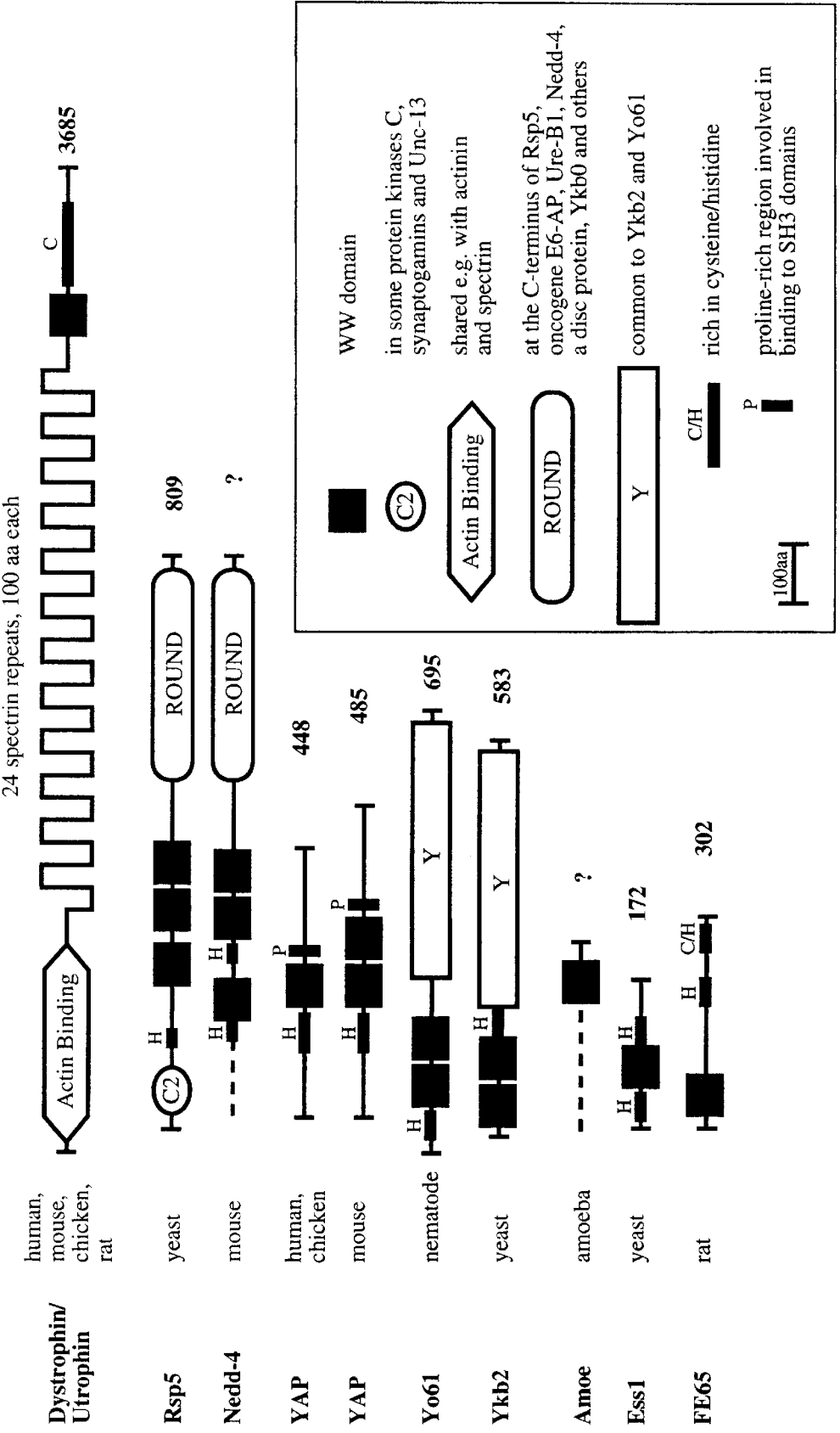

FIG. 13. Alignment of selected WW domains. Protein codes are taken from the SWISSPROT data base if available (Yo61—hypothetical protein from *C. elegans* chromosome III; YKB2 - hypothetical protein from yeast chromosome III; Dmd—dystrophin; Utro—utrophin; Amoe—hypothetical protein from Acanthamoeba). The consensus line displays conserved features (capitals—conserved amino acids, h—hydrophobic; t—turn-like or polar). Amino acids conserved in at least 60% of the sequences are shown in bold. The secondary structures were predicted using the program PHD (e—beta strand; l—loop; not assigned—nearly equal preference for both beta-strand and loop) (Rost and Sander, 1994). All segments have a probability less than $10^{-7}$ of matching the alignment by chance (computed using the MoST program (Tatusov et al., 1994)) except FE65. The WW domain in FE 65 is, however, 38% identical to that in YAP and is therefore included. Sequence Identification Information is as follows: Dmd/human (SEQ ID NO:6); Dmd/Ray (SEQ ID NO:7); Utro/Human (SEQ ID NO:8); Yap/Human (SEQ ID NO:9); Yap/Chick (SEQ ID NO:10); Yap/Mouse-1 (SEQ ID NO:11); Yap/Mouse-2 (SEQ ID NO:12); Nedd4/Mouse-1 (SEQ ID NO: 13); Nedd4/Mouse-2 (SEQ ID NO: 14); Nedd4/Mouse-3 (SEQ ID NO:15); Rsp5/Yeast-1 (SEQ ID NO:16); Rsp5/Yeast-2 (SEQ ID NO:17); Rsp5/Yeast-3 (SEQ ID NO:18); Ykb2-Yeast-1 (SEQ ID NO:19); Ykb2-Yeast-2 (SEQ ID NO:20); Yo6l/Caeel-1 (SEQ ID NO:21); Yo61/Caeel-2 (SEQ ID NO:22); Amoe/Amoeba (SEQ ID NO:23); FE65/Rat (SEQ ID NO:24); and Ess1/Yeast (SEQ ID NO:25).

Figure 14A:
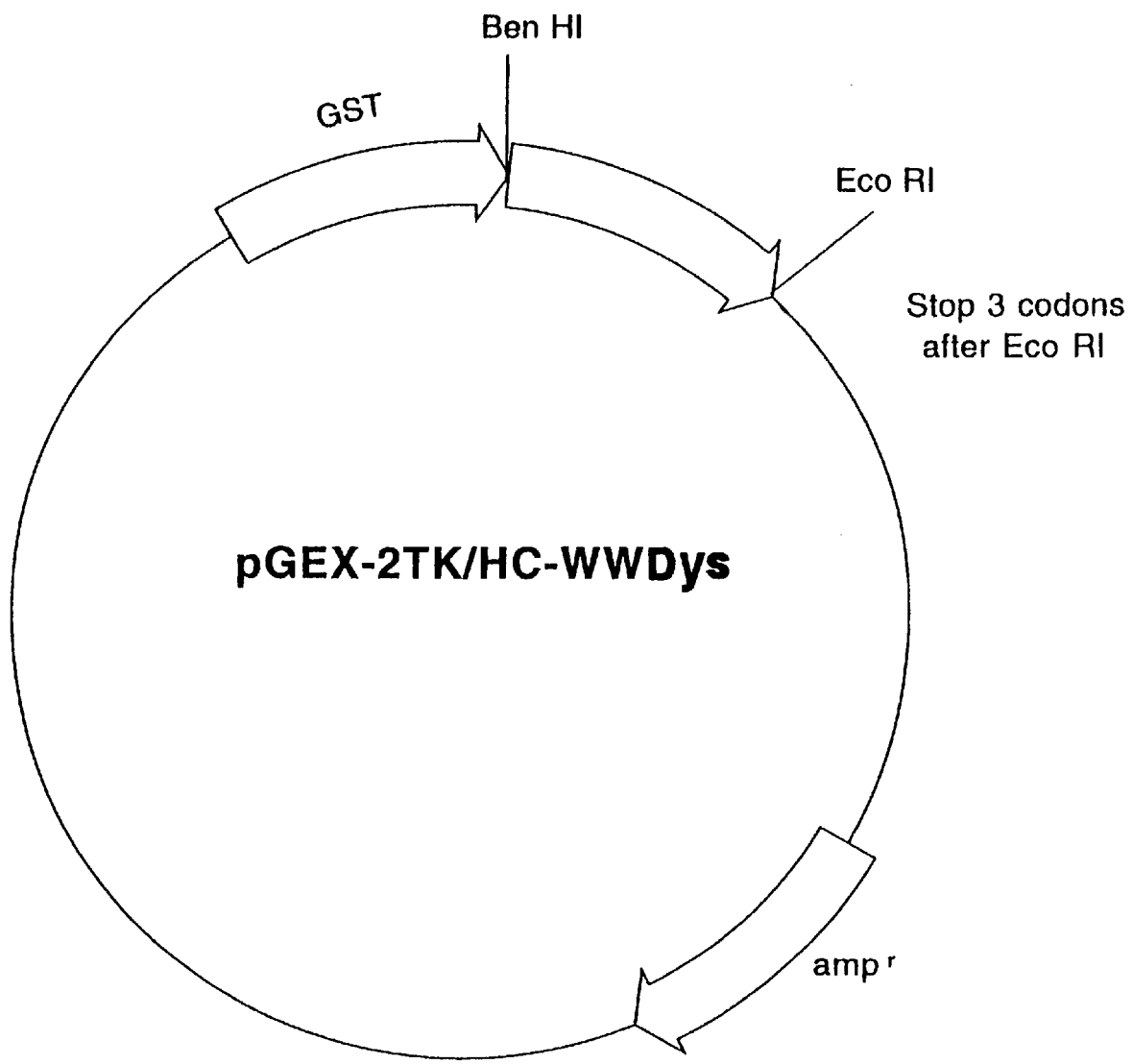
Figure 14B:
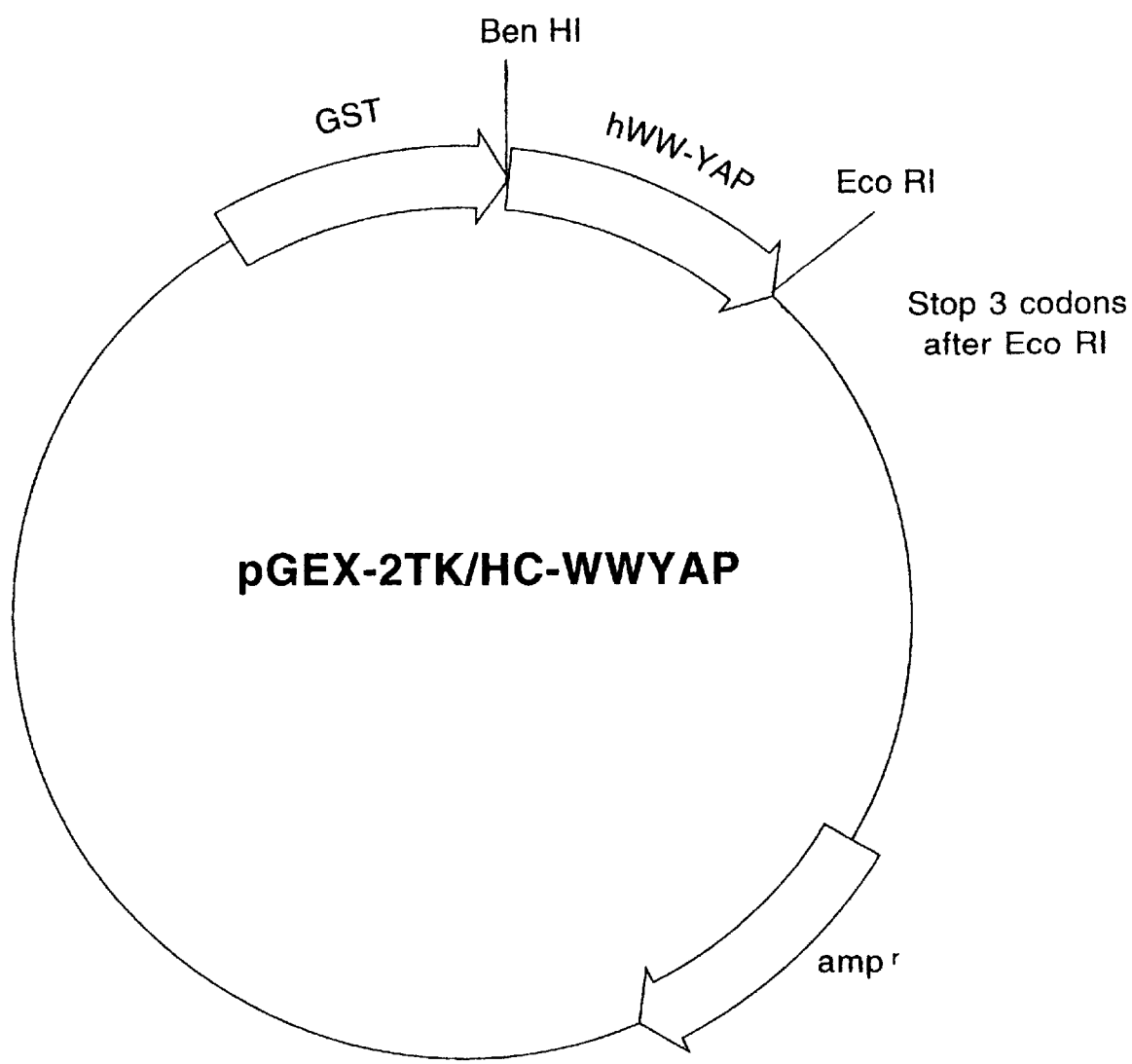

FIGS. 14A and 14B. Recombinant plasmid maps for expression the WW domains of human dystrophin and human YAP.

DETAILED DESCRIPTION OF THE INVENTION

As noted above, the present invention relates to proteins and polypeptides that are involved in intracellular signal transduction. In particular, the invention provides a novel polypeptide domain that appears to be involved in signaling. Accordingly, the invention provides nucleic acids, particularly DNA molecules, encoding such proteins and polypeptides. In one aspect, the invention relates to diagnosis of diseases or disorders, employing the polypeptides and nucleic acids of the invention. The invention further relates to modulation of intracellular signal transduction by inducing or inhibiting the activity of the proteins and polypeptides of the invention, by administration of a factor (protein or polypeptide, or nucleic acid) of the invention to a subject believed to be in need of modulation. Thus, the invention relates to methods for preparing the polypeptides and nucleic acids.

Thus, in accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual,* Second Edition (1989) Cold Spring Harbor Laboratory Press, Cold Spring Harbor, N.Y. (herein "Sambrook et al., 1989"); *DNA Cloning: A Practical Approach,* Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984).

To facilitate understanding of the invention, the following terms shall have the definitions set out below.

The term "protein" is used herein to refer to the naturally occurring form of a gene product, both in a pre-processed form (if applicable), and in a post-processed form (also if applicable). The term "polypeptide" is inclusive of the term protein, but also encompasses minor modifications, such as deletions or N- or C-terminal additional amino acid residues to facilitate expression, purification, labeling, stability of the recombinant product, and the like. A "fusion protein" is a chimeric protein comprising YAP or a fragment thereof, or particularly a WW domain, and at least a portion of a non-YAP or non-WW domain protein. Preferably, the portion of the fusion partner protein refers to a portion of a non-YAP or non-WW domain protein that is capable of (i) serving as a substrate for proteolytic cleavage (e.g., a Factor Xa sequence); (ii) binding to an antibody specific for the fusion partner protein; (iii) binding to a cognate receptor or a ligand; (iv) interacting ionically or hydrophobically with a chromatographic support; (v) catalyzing a reaction, i.e., enzymatic activity; or (vi) otherwise biologically active as assayed in vitro or in vivo.

A protein or polypeptide is said to have a "proline-rich motif" when a region of the protein or polypeptide has a disproportionate number of proline residues, including tow or more proline residues in tandem. In a specific embodiment, the proline-rich motif of the invention (from chicken YAP) has the sequence PVKQPPPLAP (SEQ ID NO:26).

The term "consensus sequence" is used herein to refer to a region or domain in a series of proteins or polypeptides that has features in common among all of the proteins or polypeptides. In a specific embodiment, the consensus sequence can be defined by determination that putative consensus segments have a probability of less than 1 in $10^6$, and preferably less than 1 in $10^7$, of matching the alignment by chance as computed on the MoST program. Alternatively, a consensus sequence can be identified by a high degree of homology or sequence similarity between a candidate segment and a consensus segment as defined by the above criteria. In the present invention, the consensus sequence is characterized by the presence of two tryptophan residues in all of the sequences (hence the designation of the pertinent domain as the WW domain), additional conserved residues, positions in which amino acid residues with either hydrophobic or hydrophilic (or turn-like) amino acid residues, and positions having a significant probability of adopting a particular secondary structure. The consensus sequence of the WW domain of the invention has the sequence:

LPtGWEXXXttt-Gt-YYhNH-TtTTtWNtPtNNt, wherein capitals indicate conserved amino acids, and boldface indicates the highly conserved tryptophan residues characteristic of the domain; h indicates a hydrophobic amino acid residue; t indicates a turn-like or polar amino acid residue; N indicates any amino acid; and a hyphen (-) indicates either no amino acid residue or any amino acid residue.

The term "secondary structure" refers to the first level of three-dimensional structure adopted by a protein or polypeptide. Secondary structural elements include the α-helix, β-sheet, β-turn, β-strand, and loop structures; the WW domain of the present invention is primarily concerned with the latter two structures, as these structures form the consensus sequence of the domain (see FIG. 12).

As used herein, the term "functionally active" refers to a polypeptide or protein having sufficient structure to mediate some activity. Such activity may be characteristic of the native protein, i.e., agonist activity. Alternatively, the functional activity may oppose that of the native protein, i.e., antagonist activity. Specific examples of functional activities of the invention include, but are not limited to, binding to an SH3 domain (or inhibition thereof), binding to an approximately 40 kDa intracellular ligand (or inhibition thereof), binding to a dystrophin-associated protein (or inhibition thereof), regulation of binding of β-dystroglycan to dystrophin, and modulation of intracellular signalling.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control. The vector may be a cloning vector, e.g., to propagate the cloned gene, or it may be an expression vector, in which a foreign gene is inserted under control of expression control sequences contained in the vector for heterologous gene expression in a recombinant host cell.

A "cassette" refers to a segment of DNA that can be inserted into a vector at specific restriction sites. The segment of DNA encodes a polypeptide of interest, and the cassette and restriction sites are designed to ensure insertion of the cassette in the proper reading frame for transcription and translation.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell. However, stable transformation with plasmid (or cosmid) DNA is also possible.

"Heterologous" DNA refers to DNA not naturally located in the cell, or in a chromosomal site of the cell. Preferably, the heterologous DNA includes a gene foreign to the cell.

A "clone" is a population of cells derived from a single cell or common ancestor by mitosis.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules") in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation. A "complementary" nucleic acid is the opposite strand, e.g., mRNA is complementary to the DNA template, antisense RNA is complementary to sense RNA, and each strand of double-stranded DNA is the complement of the other.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5x SSC, 0.1% SDS, 0.25% milk, and no formamide; or 30% formamide, 5x SSC, 0.5 % SDS). Moderate stringency hybridization conditions correspond to a higher $T_m$, e.g., 40% formamide, with 5x or 6x SCC. High stringency hybridization conditions correspond to the highest $T_m$, e.g., 50% formamide, 5x or 6x SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 10 nucleotides; more preferably at least about 15 nucleotides; most preferably the length is at least about 20 nucleotides.

The term "oligonucleotides" refers to short nucleic acids (including nucleic acids containing phosphate bond mimics, such as thiophosphates) that can be used as primers for PCR, labeled and used as probes, used for site directed mutagenesis, and for other techniques known in the art.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (*bacille Calmette-Guerin*) and *Corynebacterium parvum*. Preferably, the adjuvant is pharmaceutically acceptable.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E .W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

As used herein, the term "spectrin repeat" refers to a spectrin-like sequence, e.g., an identifiable consensus sequence found in proteins such as α-spectrin, 62-spectrin, dystrophin, and α-actinin. Spectrin repeats of the sort identified herein have heretofore never been identified on phosphatases.

In its primary aspect, the present invention is directed to YAP proteins, polypeptides comprising or consisting primarily of the WW domain, to nucleic acids encoding such proteins, to antibodies reactive with the proteins, and to methods of use of the proteins, polypeptides, and acids.

The present invention is based, in part, on the isolation and characterization of a unique Yes-associated protein from chicken, based on screening with anti-idiotypic antibodies generated against Yes SH3-specific polyclonal antibodies. With the chicken gene in hand, the human and murine orthologs (homologous genes in different species) were quickly recovered. Expression of YAP in various tissues and cells has been examined, and this protein has been found to be ubiquitous, with relatively high levels of expression in placenta, prostate, testis, ovaries, and small intestine, and relatively lower levels in brain, liver, and spleen. No YAP mRNA expression was detectable in human peritoneal leukocytes, even with overexposure of the blot.

The invention is further based on the discovery of a motif in YAP that shares significant sequence and putative structure similarities with sequences found in various regulatory and signalling proteins.

The present invention is divided into the following sections, which relate to YAP proteins, and nucleic acids encoding them; the WW domain polypeptide, and nucleic acids encoding them; ligands of the WW domain, and genes inducing them; isolating genes and expressing recombinant proteins; antibodies to the proteins; antisense nucleic acids; diagnostic applications; and therapeutic applications.

YAP Proteins and Nucleic Acids

The YAP proteins of the invention are characterized by binding to the Src homology 3 domain (SH3) of Yes and other SH3-containing proteins, including Hck, Crk, and Src. The protein is a 65 kDa MW protein in chicken, and of comparable size in human. The murine protein includes an inserted sequence that represented an imperfect repeat of the upstream sequence, and which turned out to be a repeated WW domain. YAP contains a proline rich sequence (see FIG. 8, the portion of the sequence marked with # symbols).

Human yap gene is located on the short arm on chromosome 11q13, that also harbors a gene for Multiple Endocrine Neoplasia type 1. The yap gene is highly conserved among higher eukaryotes, and expression of the gene is rather ubiquitous.

Probes for identifying orthologs can be prepared from the coding sequence of any yap gene or cDNA, and used to probe genomic or cDNA from other species. Preferably, such probing is done under non-stringent conditions. In a specific embodiment, infra, chicken yap cDNA was used to select for human and mouse yap cDNA.

In addition to the full length, mature YAP protein, the present invention further contemplates functionally active fragments of the protein, as defined above. Such fragments can be prepared by expression of a truncated nucleic acid, by chemical synthesis, or by proteolysis of the full length protein.

WW Domain Polypeptides

The present invention is also directed to polypeptides that include the consensus sequence characteristic of the WW domain, as defined hereinabove. The WW domain has from 30 to 50 amino acid residues. WW domain polypeptides of the invention may further comprise additional amino acid residues, such as N-terminal or C-terminal extensions that facilitate expression or purification. For example, a His-tag can be introduced, e.g., using pET vectors from Invitrogen. Alternatively, a GST domain-WW domain fusion protein can be expressed, as exemplified infra. Alternatively, the WW domain polypeptide, can be prepared synthetically, or by proteolytic cleavage of a protein that comprises such a domain.

In a specific embodiment, the WW domain polypeptide is expressed in an expression vector that inserts a recognition sequence for the catalytic subunit of cAMP-dependent heart muscle protein kinase, i.e., a phosphorylation site, in reading frame with the heterologous protein (pGEX-2TK, Pharmacia), between the GST domain and the protein. The recombinant WW domain polypeptide (fusion protein) can be labeled with $^{32}$P by reaction with the kinase.

Nucleic acids encoding such WW domains polypeptides can be prepared by appropriate endonuclease cleavage of cDNAs encoding such proteins, e.g., the YAP proteins. More preferably, a portion of the cDNA encoding a protein that contains a WW domain can be cloned by PCR amplification of the WW domain region using standard techniques. Specific endonuclease sites can be introduced by engineering the primers. In another embodiment, the nucleic acid encoding a WW domain can be synthesized.

The WW Domain Ligand and Nucleic Acids Encoding It

The present invention is further directed to isolation and cloning of a gene that encodes a protein that appears to be a ligand for the WW domain.

In this regard, the $^{32}$P-labeled GST-WW domain fusion (using the human dystrophyn WW domain and human YAP WW domain) described above and specifically exemplified infra, can be used to detect the presence of a ligand to the WW domain. In this way, a 35–36 kDa protein has been identified as binding to the labeled WW domain protein was identified.

The labeled WW domain polypeptide can also be used to screen an expression library for reactive clones, which are indicative of expression of the ligand. Two clones were isolated, one 1.6 kB and one 0.5 kB long.

Once partial cDNA clones are obtained from the expression library, the full length cDNA can be obtained, and the sequence determined and analyzed. From this information, a putative amino acid sequence can be deduced, and characteristics about the gene and the polypeptide can be explored.

Isolation of Genes Encoding YAP, WW Domain, and the WW Ligand

As noted above, the present invention contemplates isolation of a gene encoding a functional YAP, or portion thereof, a gene encoding a functional WW domain of the invention, or a gene encoding a ligand for the WW domain from any animal, particularly mammalian or avian, and more particularly human source. As used herein, the term "gene" refers to an assembly of nucleotides that encode a polypeptide, and includes cDNA and genomic DNA nucleic acids.

A gene encoding YAP, or a fragment thereof, or a WW domain, or a WW domain ligand, whether genomic DNA or cDNA, can be isolated from any source, particularly from a human cDNA or genomic library. Methods for obtaining the such genes are well known in the art, as described above (see, e.g., Sambrook et al., 1989, supra).

Accordingly, any animal cell potentially can serve as the nucleic acid source for the molecular cloning of a gene. The DNA may be obtained by standard procedures known in the art from cloned DNA (e.g., a DNA "library"), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II. Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the desired gene may be accomplished in a number of ways. For example, if an amount of a portion of a gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a probe having a nucleotide sequence corresponding to at least a 10, and preferably a 15, nucleotide fragment of the sequence depicted in FIG. 1 or 7 (SEQ ID NO:1 or 3, respectively), including flanking sequences. Preferably, a fragment is selected that is highly unique to the gene of interest. Those DNA fragments with substantial homology to the probe will hybridize. As noted above, the greater the degree of homology, the more stringent hybridization conditions can be used. In a specific embodiment, low stringency hybridization conditions are used to identify a homologous gene form another species (an ortholog). However, in a preferred aspect, a nucleic acid encoding a gene of the invention will hybridize to a nucleic acid having a nucleotide sequence depicted in FIG. 1 or 7 (SEQ ID NO:1 or 3, respectively), or a hybridizable fragment thereof, under moderately stringent conditions; more preferably, it will hybridize under high stringency conditions.

Further selection can be carried out on the basis of the properties of the gene, e.g., if the gene includes sequences encoding a proline-rich region or a WW domain (for yap gene), or binding to a WW domain ligand.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the gene produce, e.g., YAP, the WW domain, or the WW domain ligand. For example, the antibodies of the instant invention can conveniently be used to screen for homologs of YAP from other sources, preferably human.

A radiolabeled cDNA can be synthesized by PCR using the selected mRNA (from the adsorbed polysomes) as a template. The radiolabeled mRNA or cDNA may then be used as a probe to identify homologous DNA fragments from among other genomic DNA fragments.

The present invention also relates to cloning vectors containing genes encoding analogs and derivatives of the of the invention, that have the same or homologous functional activity as the native protein or polypeptide, and homologs thereof from other species. The production and use of derivatives and analogs related to are within the scope of the present invention. In a specific embodiment, the derivative or analog is functionally active, i.e., capable of exhibiting one or more functional activities associated with a full-length, wild-type protein of the invention.

Derivatives of the protein or polypeptide can be made by altering encoding nucleic acid sequences by substitutions, additions or deletions that provide for functionally equivalent molecules. Preferably, derivatives are made that have enhanced or increased functional activity relative to the native protein or polypeptide.

Due to the degeneracy of nucleotide coding sequences, other DNA sequences which encode substantially the same amino acid sequence as a yap, WW domain, or WW domain ligand gene may be used in the practice of the present invention. These include but are not limited to nucleotide sequences comprising all or portions of genes which are altered by the substitution of different codons that encode the same amino acid residue within the sequence, thus producing a silent change. Likewise, the derivatives of the invention include, but are not limited to, those containing, as a primary amino acid sequence, all or part of the amino acid sequence of a protein or polypeptide of the invention including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such substitutions are particularly contemplated for the consensus sequence of the WW domain, which clearly identifies those positions that are immutable, those positions that are highly conserved, those positions that have a strong polar or non-polar character, and those positions for which it simply does not matter what amino acid is there.

The genes encoding derivatives and analogs of the invention can be produced by various methods known in the art. The manipulations which result in their production can occur at the gene or protein level. For example, the cloned gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog, such as with a fusion protein, care should be taken to ensure that the modified gene remains within the same translational reading frame as the gene, uninterrupted by translational stop signals, in the gene region where the desired activity is encoded.

Additionally, the encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification,* H. Erlich, ed., Stockton Press, Chapter 6, pp. 61–70).

Expression of Proteins and Polypeptides

The nucleotide sequence coding for a YAP, WW domain polypeptide, or WW domain ligand, or functional fragment, derivative or analog thereof, can be inserted into an appropriate expression vector, i.e., a vector which contains the necessary elements for the transcription and translation of the inserted protein-coding sequence. Such elements are termed herein a "promoter." Thus, the nucleic acid encoding a polypeptide or protein of the invention is operationally (operably) associated with a promoter in an expression vector of the invention. Both cDNA and genomic sequences can be cloned and expressed under control of such regulatory sequences.

An expression vector also preferably includes a replication origin.

The necessary transcriptional and translational signals can be provided on a recombinant expression vector, or they may be supplied by the native gene encoding a and/or its flanking regions.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant of the invention, or functional fragment, derivative or analog thereof, may be expressed chromosomally, after integration of the coding sequence by recombination. In this regard, any of a number of amplification systems may be used to achieve high levels of stable gene expression (See Sambrook et al., 1989, supra) can be used.

The cell into which the recombinant vector comprising the nucleic acid encoding the protein or polypeptide is cultured in an appropriate cell culture medium under conditions that provide for expression of the protein or polypeptide by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of a protein or polypeptide may be controlled by any promoter/enhancer element known in the art, but these regulatory elements must be functional in the host selected for expression. Promoters which may be used to control gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals.

Expression vectors containing a nucleic acid encoding a of the invention can be identified by four general approaches: (a) PCR amplification of the desired plasmid DNA or specific mRNA, (b) nucleic acid hybridization, (c) presence or absence of "marker" gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted gene. In the third approach, the recombinant vector/host system can be identified and selected based upon the presence or absence of certain "marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid encoding a is inserted within the marker gene sequence of the vector, recombinants containing the insert can be identified by the absence of the marker gene function. In the fourth approach, recombinant expression vectors can be identified by assaying for the activity of the gene product expressed by the recombinant, provided that the expressed protein assumes a functionally active conformation. Such assays can be based, for example, on the physical or functional properties of the gene product in in vitro assay systems, e.g., tyrosine phosphorylation, or alternatively binding with antibody.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce a nonglycosylated core protein product. However, the transmembrane protein expressed in bacteria may not be properly folded. Expression in yeast can produce a glycosylated product. Expression in eukaryotic cells can increase the likelihood of "native" glycosylation and folding of a heterologous protein.

Furthermore, different vector/host expression systems may affect processing reactions, such as proteolytic cleavages, to a different extent.

Vectors are introduced into the desired host cells by methods known in the art, e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

Recombinant protein can be isolated and purified by standard methods. Generally, the protein or polypeptide, which is expected to be expressed into the cytoplasm, can be obtained by lysing the membrane with detergents, such as but not limited to, sodium dodecyl sulfate (SDS), Triton X-100, nonidet P40 (NP40), digoxin, sodium deoxycholate, and the like, including mixtures thereof. Solubilization can be enhanced by sonication of the suspension. Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), including chromatography (e.g., ion exchange, affinity, immunoaffinity, and sizing column chromatography), centrifugation, differential solubility, immunoprecipitation, or by any other standard technique for the purification of proteins.

In yet another specific embodiment, a protein or polypeptide, or fragment, derivative, or analog thereof, can be expressed as a GST-fusion protein in a bacterial expression system. Preferably, a fragment, such as the WW domain, is expressed in such a system. A cDNA or gene fragment can be isolated, as described above, gel purified, blunt-ended with T4 DNA polymerase, and ligated with EcoRI-linearized, blunt ended PGEX-3X DNA (Smith and Johnson, 1988, Gene 67:31–40). The ligation mixture can then be transformed into E. coli and the clones obtained analyzed by restriction digestion and DNA sequencing. Products of resulting plasmids can be purified over glutathione-SEPHAROSE resin and eluted with free glutathione. The glutathione can be removed by passage through a PD10 desalting column.

For expression in insect cell, the invention specifically provides for infection of Sf9 (*Spodoptera frugiperda*) cells at a multiplicity of infection of 10, with a recombinant baculovirus (*Autographa californica*), made by subcloning cDNA into the pAcYM1 vector (Matsura et al., 1987, J. Gen. Virol. 68:1233–50). After 72 hours, cells can be lysed by Dounce homogenization in TNE buffer, and protein products purified by gel filtration, antibody affinity chromatography, or a combination of chromatography steps.

In another embodiment, the gene of the invention is expressed in an indicator cell line, which is discussed in detail, infra. In this embodiment, isolation of the expressed protein is not desired, since the functional activity of the expressed protein in the indicator cell line is the property most of interest.

Identification and Characterization of Polypeptides

Once a recombinant which expresses the gene sequence is identified, the recombinant product can be analyzed. This is achieved by assays based on the physical or functional properties of the product, including radioactive labelling of the product followed by analysis by gel electrophoresis, immunoassay, etc.

For example, the ability of the expressed protein, or a fragment thereof, to function in an assay, can be determined.

The structure of a YAP protein, a WW domain polypeptide, or a WW domain ligand of the invention can be analyzed by various methods known in the art. Preferably, the structure of the various domains, particularly the domain, is analyzed. Structural analysis can be performed by identifying sequence similarity with other known proteins, as was performed in identifying the WW domain. The degree of similarity (or homology) can provide a basis for predicting structure and function of a similar domain. In a specific embodiment, sequence comparisons can be performed with sequences found in GenBank, using, for example, the FASTA and FASTP programs (Pearson and Lipman, 1988, Proc. Natl. Acad. Sci. USA 85:2444–48).

The protein sequence can be further characterized by a hydrophilicity analysis (e.g., Hopp and Woods, 1981, Proc. Natl. Acad. Sci. U.S.A. 78:3824). A hydrophilicity profile can be used to identify the hydrophobic and hydrophilic regions of the a protein.

Secondary structural analysis (e.g., Chou and Fasman, 1974, Biochemistry 13:222) can also be done, to identify regions of a protein or polypeptide that assume specific secondary structures.

Manipulation, translation, and secondary structure prediction, as well as open reading frame prediction and plotting, can also be accomplished using computer software programs available in the art.

By providing an abundant source of recombinant proteins and polypeptides, the present invention enables quantitative structural determination of the protein, or domains thereof. In particular, enough material is provided for nuclear magnetic resonance (NMR), infrared (IR), Raman, and ultraviolet (UV), especially circular dichroism (CD), spectroscopic analysis. In particular NMR provides very powerful structural analysis of molecules in solution, which more closely approximates their native environment (Marion et al., 1983, Biochem. Biophys. Res. Comm. 113:967–974; Bar et al., 1985, J. Magn. Reson. 65:355–360; Kimura et al., 1980, Proc. Natl. Acad. Sci. U.S.A. 77:1681–1685). Other methods of structural analysis can also be employed. These include but are not limited to X-ray crystallography (Engstom, A., 1974, Biochem. Exp. Biol. 11:7–13).

In a specific embodiment, the crystal structure of human YAP and human dystrophin are being obtained and compared, to determine the molecular consequences of the observed similarity between these proteins, particularly at the level of the WW domain.

More preferably, co-crystals of Yes and YAP can be prepared, so that the exact nature of the binding reaction can be studied. Similarly, co-crystals of the WW domain and the WW domain ligand can be prepared. Analysis of co-crystals provides detailed information about binding, which in turn allows for rational design of ligand agonists and antagonists. Computer modeling can also be used, especially in connection with NMR or X-ray methods (Fletterick, R. and Zoller, M. (eds.), 1986, Computer Graphics and Molecular Modeling, in *Current Communications in Molecular Biology*, Cold Spring Harbor Laboratory, Cold Spring Harbor, N.Y.)

Antibodies

According to the invention, recombinant proteins or polypeptides, and fragments or other derivatives or analogs thereof, or cells expressing the foregoing may be used as an immunogen to generate antibodies which recognize the cognate protein or polypeptide. Such antibodies include but are not limited to polyclonal, monoclonal, chimeric, single chain, Fab fragments, and an Fab expression library. In another embodiment, infra, anti-idiotype antibodies can be generated to a binding partner of the protein or polypeptide, for example to anti-Yes antibodies, in order to obtain antibodies reactive, in this instance, with YAP. Moreover, it was a surprising result that such antibodies could in fact be obtained.

Various procedures known in the art may be used for the production of polyclonal antibodies to a recombinant or derivative or analog thereof. For the production of antibody, various host animals can be immunized by injection with the recombinant, or a derivative (e.g., fragment) thereof, including but not limited to rabbits, mice, rats, etc. In one embodiment, the recombinant or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (*bacille Calmette-Guerin*) and *Corynebacterium parvum*.

For preparation of monoclonal antibodies directed toward an or analog thereof, any technique which provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule specific for a λ together with genes from a human antibody molecule of appropriate biological activity can be used; such antibodies are within the scope of this invention. Such human or humanized chimeric antibodies are preferred for use in therapy (described infra), since the human or humanized antibodies are much less likely than xenogenic antibodies to induce an immune response, in particular an allergic response, themselves.

According to the invention, techniques described for the production of single chain antibodies (U.S. Pat. No. 4,946, 778) can be adapted to produce specific single chain antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment; and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope, one may assay generated hybridomas for a product which binds to a fragment containing such epitope. For selection of an antibody specific to an YAP, WW domain, or WW domain ligand from a particular species of animal, one can select on the basis of positive binding with the protein or polypeptide expressed by or isolated from cells of that species of animal.

The foregoing antibodies can be used in methods known in the art relating to the localization and activity of their binding partners, e.g., for Western blotting, imaging, measuring levels thereof in appropriate physiological samples, etc.

In a specific embodiment, antibodies that agonize or antagonize the activity of can be generated. Such antibodies can be tested using the assays described infra for identifying ligands.

Ligand Agonists and Antagonists of

Identification and isolation of a gene encoding YAP, a WW domain, or the WW domain ligand of the invention provides for expression of the protein in quantities greater than can be isolated from natural sources, or in indicator cells that are specially engineered to indicate the activity of a protein expressed after transfection or transformation of the cells. According, the present invention contemplates identifying specific ligands of using various screening assays known in the art.

Any screening technique known in the art can be used to screen for agonists or antagonists. The present invention contemplates screens for small molecule ligands or ligand analogs and mimics, as well as screens for the native ligand that binds to and activates of the invention in vivo.

Knowledge of the primary sequence of the protein, and the similarity of that sequence with proteins of known function, can provide an initial clue as the inhibitors or antagonists of the protein. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of inhibitors and antagonists.

Another approach uses recombinant bacteriophage to produce large libraries. Using the "phage method" (Scott and Smith, 1990, Science 249:386–390; Cwirla, et al., 1990, Proc. Natl. Acad. Sci., 87:6378–6382; Devlin et al., 1990, Science, 249:404–406), very large libraries can be constructed ($10^6$–$10^8$ chemical entities). A second approach uses primarily chemical methods, of which the Geysen method (Geysen et al., 1986, Molecular Immunology 23:709–715; Geysen et al. 1987, J. Immunologic Method 102:259–274) and the recent method of Fodor et al. (1991, Science 251, 767–773) are examples. Furka et al. (1988, 14th International Congress of Biochemistry, Volume 5, Abstract FR:013; Furka, 1991, Int. J. Peptide Protein Res. 37:487–493), Houghton (U.S. Pat. No. 4,631,211, issued December 1986) and Rutter et al. (U.S. Pat. No. 5,010,175, issued Apr. 23, 1991) describe methods to produce a mixture of peptides.

In another aspect, synthetic libraries (Needels et al., 1993, "Generation and screening of an oligonucleotide encoded synthetic peptide library," Proc. Natl. Acad. Sci. USA 90:10700-4; Lam et al., International Patent Publication No. WO 92/00252, each of which is incorporated herein by reference in its entirety), and the like can be used to screen for ligands according to the present invention.

In a specific embodiment, infra, the peptide PVKQPP-PLAP (SEQ ID NO:26) is shown to inhibit binding of YAP to Yes.

Diagnostic and Therapeutic Compositions and Methods

Protein binding is one means by which cells accomplish signal transduction, and thus control activation, proliferation, and differentiation. Therefore, the level of expression of YAP, proteins containing the WW domain, and the ability to modulate activity of such proteins and polypeptides of the invention, can be very important for the diagnosis and treatment of diseases of disorders, particularly cellular transformations that lead to cancer, and to disorders such as muscular dystrophy.

Thus, the nucleic acid probes (enzyme or radio-labeled nucleotides) or antibodies of the invention can be used to detect expression, and measure the level of expression, of a YAP protein, or a protein carrying a WW consensus sequence of the invention in selected tissues. For example, the presence or absence of expression of YAP in cancer cells obtained in a tissue biopsy can be important in evaluating whether the normal cellular control machinery are operating. Similarly, the presence or absence, and level of expression, of the invention in immune cells can provide information about the level of immune activation and regulation.

In another embodiment, the WW domain can be used as a probe for the presence or level of the ligand to which it binds. Information about the level of the ligand is informative with respect to the state of cellular activation, oncogenesis, and other indicia of metabolic state.

In another embodiment, the level of Yes and other SH3-containing proteins can be evaluated by detecting the level of binding of YAP protein to the sample being assayed. In a further aspect, signal transduction can be evaluated by detecting the level of phosphorylation of the YAP protein in cells in vivo.

In a further embodiment, antibodies generated to YAP, the WW domain or domains, or to the WW domain ligand can be used to evaluate the presence or level of activity of the proteins or polypeptides. Immunoassays can be performed by any of the standard techniques described above. The presence of low levels of YAP or particular proteins containing specific WW domains may be indicative of a disease or disorder characterized by a decrease in cellular metabolic activity, possibly resulting from the low level of YAP or WW domains. Conversely, increased levels of these proteins may be characteristic of cellular activation, e.g., such as accompanies oncogenesis.

In another aspect of the invention, antisense oligonucleotides capable of hybridizing to yap or WW domain mRNA can be used to inhibit expression of either protein in a cell, and thus modulate signal transduction activity in a cell. Inhibition of signalling activity can be useful, e.g., to modulate the activity of various cells. For example, if testicular or ovarian cells become transformed, it may be desirable to inhibit signalling mediated by YAP interaction with Yes, or by inhibiting the signalling mediated by the WW domain, in order to inhibit or reverse the transformation.

In a further aspect of the invention, YAP or the WW domain can be introduced into cells, either directly or by gene therapy, to increase the level of signal transduction. In a specific embodiment, the WW domain can be introduced into muscle cells of a subject suffering from a form of muscular dystrophy characterized by a mutation in the dystrophin WW domain. Supplementation of the activity of the dystrophin WW domain, by introduction of a functionally active WW domain may be used to reverse the degeneration of muscle cells that accompanies muscular dystrophy.

In a further embodiment, ligand agonists or antagonist can be used to modulate cellular activity by increasing or decreasing the signalling activity of the either YAP or the WW domain-containing proteins, or both in cells. In a particular aspect, the ligand for the WW domain can be introduced into cells, either directly or by gene therapy, to increase the level of WW domain ligand activity in the cells.

The present invention may be better understood by reference to the following non-limiting example, which is provided by way of exemplification.

EXAMPLE 1: Identification of Chicken YAP65

The present example relates to the identification of a novel gene and its deduced protein product. This protein was isolated by binding to anti-idiotype antibodies against the amino terminal domain of Yes, a member of the Src family of protein-tyrosine kinases involved in signaling. The results reported herein were previously published by Sudol (a co-inventor of this application) (1994, Oncogene 9:2145–51, which is hereby specifically incorporated herein by reference in its entirety).

Materials and Methods

Cells and Antibodies

All passages of CEFs were prepared and maintained as previously described (Sudol & Hanafusa, 1986). Anti-Yes serum was generated in rabbits against a portion of bacterially expressed Yes protein that contains its entire unique and SH3 domains (Sudol & Hanafusa, 1986). Anti-idiotypic antibodies (Jerne, 1974) were raised in rabbits following a published protocol (Strosberg, 1989). Two rabbits were injected with 500 μg of affinity purified anti-Yes IgG. Five boosts, 200 pg each, were started one and a half months after the initial injection and continued in 2 week intervals. After the second boost the serum showed immunoreactivity. Antibodies against YAP65 were generated in rabbits against a portion of the YAP65 sequence (nucleotides 381–1298) expressed in bacteria using the TrpE-expression vector as previously described for Yrk (Sudol et al., 1993). Polymerase Chain Reaction was used to generate the YAP65 cDNA insert with appropriate cloning sites. The open reading frame of the beta-galactosidase protein in the original lambda gt11 clone (1 kb long clone) indicated the reading frame of YAP65. Antibodies against the human GAP protein that recognize also the chicken GAP protein on Western blots were purchased from UBI (Lake Placid, N.Y.).

Fusion Proteins and Peptides

GST-SH3-Yes fusion protein was obtained by subcloning a PCR amplified SH3 fragment of cDNA (Sudol et al., 1988) into pGEX-3X vector in frame using BamHI and EcoRI restriction sites engineered at the end of the amplified cDNA. Purification was on a glutathione-Sepharose column. Purified fusion proteins encoding Gst-Nck (Chou et al., 1992), Gst-Crk (Birge et al., 1992), Gst-SH3-Src (Cicchetti et al., 1992), Gst-SH3-Abl (Cicchetti et al., 1992), and Gst-SH3-GAP were a gift from Stephan Feller and Beatrice Knudsen, The Rockefeller University. Two peptides used in the competition studies: "PLAP" (ISQSAPVKQPPPLAPQSPQGGV corresponding to the YAP65 sequence, amino acids 233–254) and 'SPLAP' (VQPAQLSIPGPVSPQPKGQSPA, a scrambled version of 'PLAP' without any consecutive prolines) were synthesized by the Rockefeller Protein Sequencing Facility following standard protocols of the solid phase synthesis (Merrifield, 1963).

Immunoassays

Figures 1A, 1B:
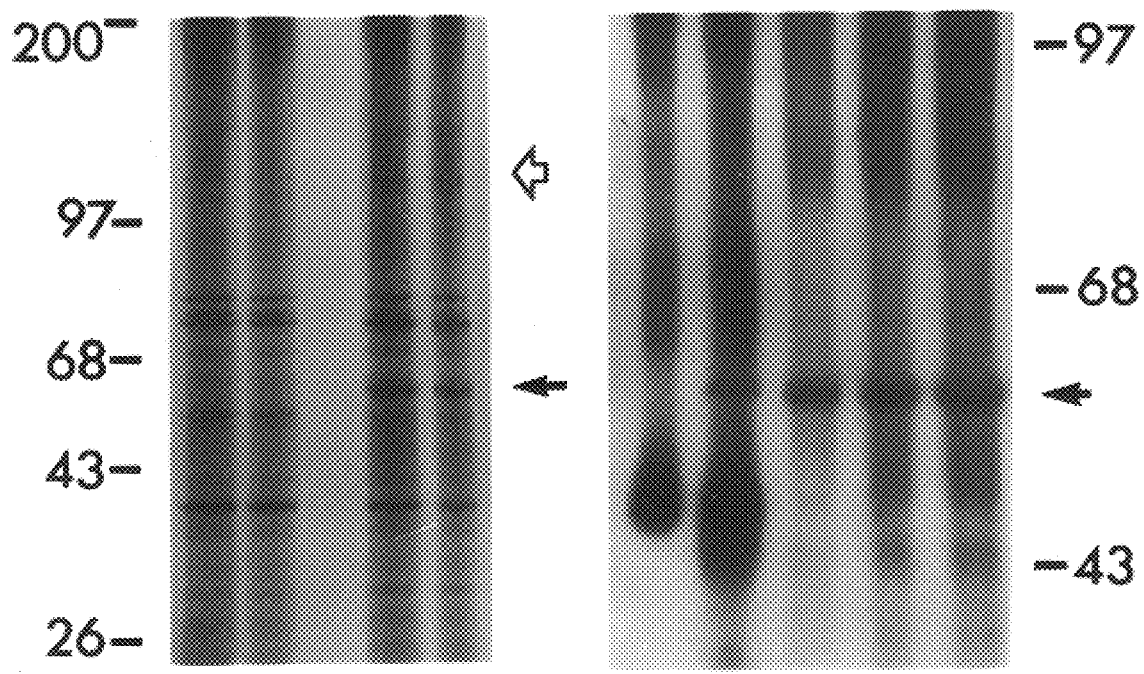
FIG. 1. Identification of the 65 kDa (YAP65) and a 120 kDa protein by anti-sera against anti-Yes IgG. (A) Lanes 1–4: Immunoprecipitation from lysates of $^{35}$S-methionine labeled CEFs with sera from two rabbits. Lanes 1 and 2 were precipitated with preimmune sera; lanes 3 and 4 were precipitated with immune sera. (B) Lanes 5–9: Immune blot analysis. Immunoprecipitates with preimmune (lane 5) or anti-idiotypic immune (lane 6) serum, or total lysates of primary (lane 7), secondary (lane 8), and tertiary (lane 9) CEFs were resolved on polyacrylamide gel, transferred to a nitrocellulose membrane, and probed with anti-idiotypic serum and $^{125}$-labeled-protein A. Solid arrows indicate YAP65, and an open arrow shows 120 kDa protein. The 120 kDa protein was not detected on the immune blot. Molecular size markers are shown in kDa.

Cell lysates were prepared in 150 mM NaCl RIPA buffer with protease inhibitors (Sudol & Hanafusa, 1986). The autophosphorylation kinase assay and Western blot analyses were as previously described (Sudol & Hanafusa, Results Immunoreactivity of Anti-anti-Yes Sera Antisera generated in two rabbits against the affinity purified anti-Yes IgG fraction (Sudol & Hanafusa, 1986) precipitated a 65 kDa protein, as well as a 120 kDa protein, from CEFs metabolically labeled with [$^{35}$S]methionine (FIG. 1, lanes 3 and 4). The 65 kDa protein was also detected by immune blot analysis in total lysates of CEFs from various passages (FIG. 1, lanes 6–9). The even intensity of the 65 kDa band in primary and tertiary CEFs eliminated the possibility that the 65 kDa protein is derived from non-fibroblastic cells frequently contaminating primary cultures.

Isolation of cDNA for YAP65

Figure 2C:
FIG. 2. The sequence of the chicken YAP6S cDNA and the predicted protein product. The cDNA sequence of the original clone isolated with the anti-idiotypic antibodies is indicated with arrows. The sequence of a proline-rich motif implicated in the binding of YAP65 to the SH3 domain of Yes is underlined. The termination codon is shown as END. Four independent and overlapping cDNA clones were used to reconstruct the entire sequence.

High levels of Yes expression in cerebellum (Sudol et al., 1989) and the detection of YAP65 in cerebellum by immune blot (data not shown) pointed to a source of RNA for the isolation of YAP65 cDNA. mRNA from the cerebella of 2-week-old chicks was used for production of the cDNA and the construction of a cerebellar cDNA library in lambda gt11 phage (Young & Davis, 1983). Using anti-idiotypic sera, we screened the cerebellar cDNA library. The screen resulted in one clone containing a 1 kb long insert (FIG. 2, arrows). The combined sequence of the original (1 kb long) clone and of four independently isolated overlapping clones is shown in FIG. 2.

The cDNA predicted sequence of YAP65 did not show any significant similarity at the DNA or protein levels when compared with GenBank sequences. The YAP65 sequence's most prominent feature is the high content of proline and glutamine residues. In addition, we have identified a motif—PVKQPPLAP—(FIG. 2) that is similar to the sequence identified by Ren and colleagues in proteins that bind in vitro to the SH3 domain of Abl (Ren et al., 1993). This motif agrees well with the SH3-binding site consensus proposed by Schreiber and his colleagues (Chen et al., 1993; Yu et al., 1994).

Validation of the cDNA Sequence; YAP65 is a Phosphoprotein

Figure 3:
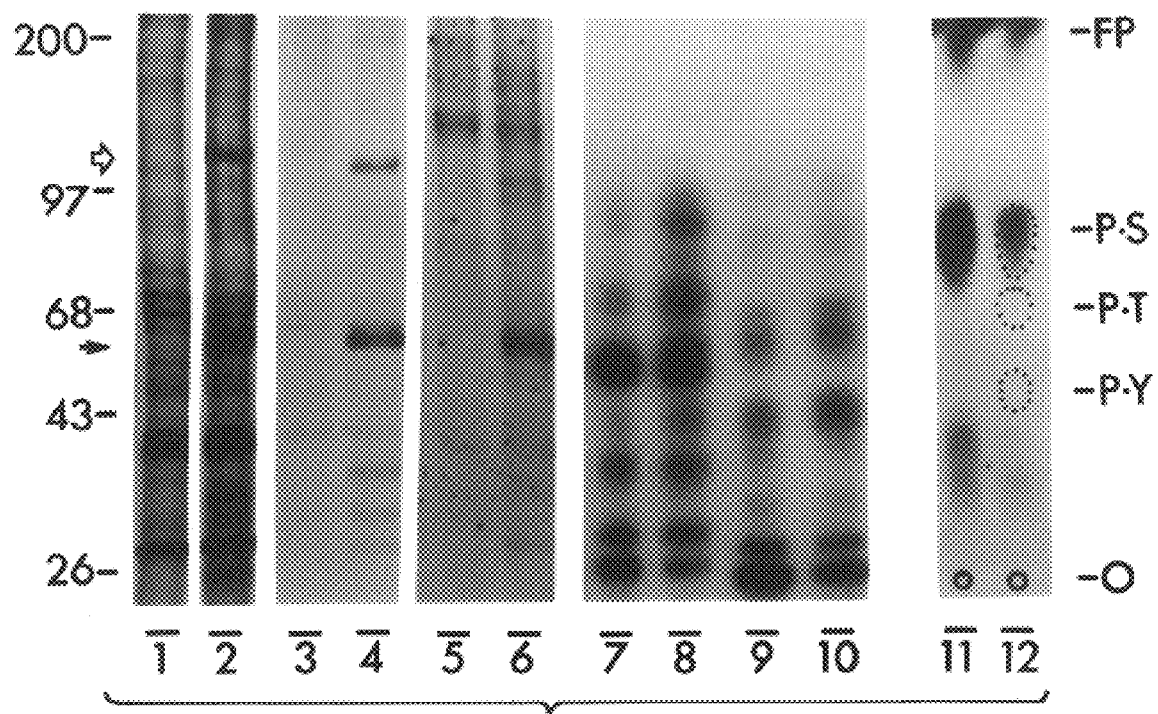
FIG. 3. Validation of the YAP65 cDNA (1–10) and phosphorylation of YAP 65 protein on serine residues (11–12). Immunoprecipitation of $^{35}$-labeled CEFs with preimmune (1) and anti-idiotypic IgG (2), or with preimmune IgG (3) and with IgG against TrpE-YAP65 fusion protein (4). Lanes 5 and 6 are as 3 and 4, respectively, but the immunoprecipitation was from CEFs labeled with [$^{32}$P$_i$]. One dimensional tryptic peptide mapping of YAP65 precipitated with IgG against TrpE-YAP65 fusion protein (7) or with anti-idiotypic antibody (8); lane 9, tryptic peptide map of the 120 kDa protein precipitated with anti TrpE-YAP65 or with anti-idiotypic antibody (lane 10). One dimensional phosphoamino acid analysis of YAP65 (lane 11) and 120 kDa protein (lane 12). O—origin of the sample application; P-Y, phosphotyrosine; P-T, phosphothreonine; P-S, phosphoserine; FP, free phosphate. Arrows are as in FIG. 1. Black triangle on right side of lane 6 indicates the position of 120 kDa protein.

To show that the cloned cDNA corresponds to the YAP65 identified by anti-idiotypic sera, we have expressed a part of the cDNA in bacteria using a TrpE operon based vector. Polyclonal antibodies generated in rabbits against the TrpE-YAP65 fusion protein precipitated from CEFs a 65 kD protein that comigrated with YAP65 identified by anti-idiotypic sera (FIG. 3, lanes 2 and 4). One dimensional peptide mapping confirmed the identity of the two proteins (FIG. 3, lanes 7 and 8). By the same method, we have also determined that the 120 kDa protein precipitated with anti-idiotypic antibodies and with antibodies generated against the bacterially expressed YAP65 protein are identical (FIG. 3, lanes 9 and 10). By the criterion of the tryptic peptide mapping, the 120 kDa protein differs from YAP65 (FIG. 3, lanes 8 and 9). However, our data do not exclude the possibility that the 120 kDa protein shares some epitopes with YAP65. Interestingly, in CEFs, YAP65 and the I20 kDa protein are phosphorylated constitutively and exclusively on serine residues (FIG. 3, lanes 5,6 and 11, 12).

Figure 4A:
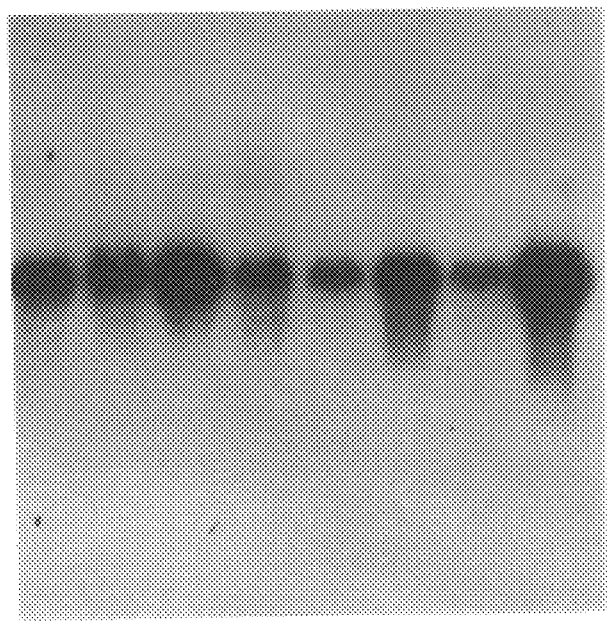
FIG. 4. Northern blot analysis of YAP65 and Yes mRNAs. Five micrograms of polyA$^+$ mRNA from telencephalon (1), or cerebellum (2), spleen (3), intestine (4), muscle (5), heart (6), liver (7), and kidney (8) of 2-week-old chicks were probed with radioactive YAP65 cDNA (A) or with Yes cDNA (B). Numbers to the right of the gel are sizes of mRNAs in kilobases.
Figure 4B:
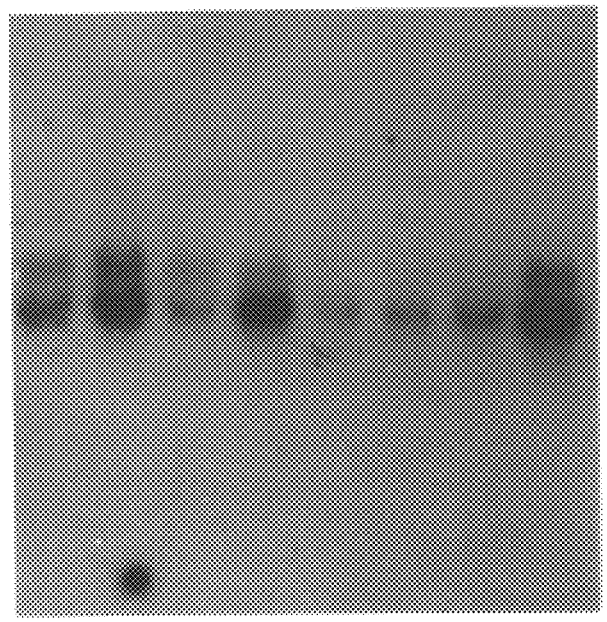

On Northern blots, the YAP65 cDNA detected a single 4.2 kb transcript expressed ubiquitously in various chicken tissues including brain (telencephalon, cerebellum), heart, spleen, intestine, liver, kidney and muscle (FIG. 4). There was no quantitative correlation between the patterns of YAP65 and Yes mRNA expression except that both were expressed ubiquitously.

YAP65 Binds to Yes in vitro and In Cell Lysates

Figure 5A:
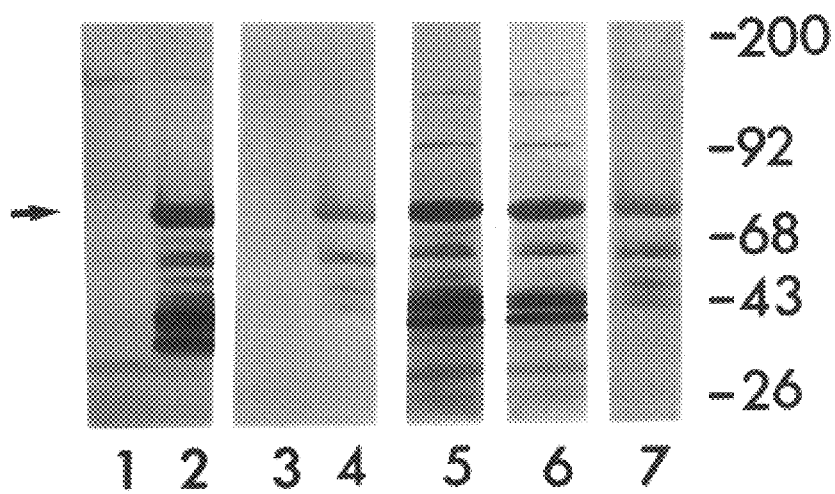
FIG. 5. Binding between YAP65 and Yes in vitro. (A) TrpE-YAP65 fusion protein (2,4,5,6,7) or TrpE alone (1,3) were probed on Western blots with 35S-methionine labeled GST-Yes-SH3 alone (2) or with radioactive GST-Yes-SH3 supplemented with 10 μM of cold GST-Yes-SH3 (4); Lane 5 is as in lane 2 but the incubation was in the presence of SPLAP peptide (200 μM); lanes 6 and 7, the binding was competed with 50 μM and 200 μM of the PLAP peptide, respectively. The arrow indicates partially purified TrpE-YAP65 fusion protein. Lower migrating protein bands represent products of proteolytic degradation. Even if an increased concentration of protease inhibitors and careful purification protocols were used, we always observed limited degradation of the TrpE-YAP65 protein. Equal amounts (8 μg) of TrpE-fusion protein or TrpE protein were loaded into each lane of the SDS-polyacrylamide gel and transferred to nitrocellulose. (B) Differential binding of $^{35}$S-labeled TrpE-YAP65 fusion protein to various fusion proteins containing SH3 domains. Before the Western transfer, we had loaded equal amounts (1 μg) of purified proteins into each lane of the SDS gel. An SDS-polyacrylamide gel was run in parallel and stained with Coomassie Blue to confirm equal concentrations of the purified proteins. Lane 1, GST protein itself; lane 2, GST-Nck; lane 3, GST-SH3-Yes; lane 4, GST-c-Crk; lane 5, GST-SH3-Src; lane 6, GST-SH3-Abl; and lane 7, GST-SH3-GAP.

We assayed for binding between the bacterially expressed fusion proteins of YAP65 and Yes. As shown in FIG. 5a, lanes 1 and 2, $^{35}$S-methionine labeled GST-YES-SH3 protein bound to TrpE-YAP65 immobilized on nitrocellulose (lane 2) but not to TrpE alone (lane 1). GST alone or GST-YES-SH2 did not show any binding to TrpE-YAP65 (data not shown). To show binding specificity, we used cold GST-YES-SH3 protein in a competition assay (FIG. 5a, lane 4) In order to evaluate the involvement of the proposed proline-rich motif of YAP65 in binding to the SH3 domain of YES, we incubated $^{35}$S-methionine labeleled GST-YES-SH3 protein with TrpE-YAP65 immobilized on nitrocellulose in the presence of SPLAP peptide (a scrambled peptide) or PLAP peptide (amino acids 233–254 corresponding to the proline rich motif. Only the PLAP peptide competed in binding between Trp-E-YAP65 and GST-YES-SH3 fusion proteins (FIG. 5a, lanes 5–7).

To perform reciprocal binding and to estimate the relative specificity of YAP65 binding to other proteins that contain SH3 domains, we probed the purified GST fusion protein s of Nck, Crk, Src, Abl and GAP with radioactively labeled TrpE-YAP65 protein. The same amount of protein was analysed in a membrane binding assay; TrpE-YAP65 bound the strongest to Nck and Yes followed by Crk, and Src.

Figure 5B:
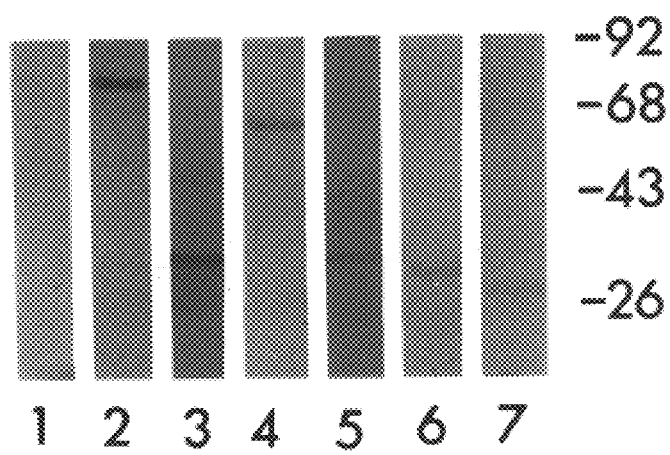

Binding of TrpE-YAP65 to the GST-SH3 domains of Abl and GAP was relatively weak (FIG. 5b).

To document direct interaction between YAP65 and Yes we attempted to coprecipitate Yes with YAP65 antibodies and YAP65 with Yes antibodies. The results were negative. However, when we partially purified YAP65 protein from CEFs and coupled it covalently to Sepharose beads, we were able to precipitate the Yes protein from CEF lysates (FIG. 6).

Discussion

Using polyclonal antibodies raised in rabbits against affinity purified polyclonal antibodies recognizing the unique and SH3 domain of the Yes protein, we detected a 65 kDa protein (YAP65) that formed a complex with the Yes proto-oncogene product in in vitro assays. With thus generated antibodies, we cloned the YAP65 cDNA from an expression library. By a number of criteria, we showed that YAP65 interacts specifically with the SH3 domain of the Yes protein and at differing affinities, it also binds to other signaling molecules that contain SH3 domains including Nck and Crk. Based on previous findings (Ren et al., 1993), we identified a short proline-rich sequence within YAP65—VKQPPPLAP—and showed its involvement in binding to the SH3 domain of Yes in vitro. We also documented coprecipitation of the Yes kinase with the YAP65 protein in cell lysates prepared in buffers containing non-ionic detergents.

The following aspects of the work deserve brief comment: (i) the use of polyclonal antibodies in the generation of anti-idiotypic antibodies; (ii) the identity of the 120 kDa protein that is found in YAP65 immunoprecipitates; (iii) the hallmarks and subtle features of the YAP65 cDNA and the predicted protein product, and (iv) the potential biological significance of the YAP65-Yes interaction.

The decision to generate polyclonal anti-idiotypic antibodies against polyclonal antibodies, rather than to use monoclonal antibodies as antigens, stemmed from two observations. (i) The primary anti-Yes serum was generated against a portion of the Yes protein (Sudol & Hanafusa, 1986) and recognized strongly the Yes SH3 domain and only weakly the unique domain, although both regions were represented in the antigen in equivalent molar amounts (Sudol, unpublished). (ii) Mapping of binding domains for the monoclonal antibodies generated against another closely related kinase, Src, provided suggestive evidence on the 'immunodominance' of epitopes within the SH3 domain (Parsons et al., 1986). Based on these two observations, we argued that by using polyclonal antibodies (first antibody, anti-Yes) directed to the apparently dominant epitope(s) (Yes SH3), we may obtain anti-idiotypic antibodies (Jerne, 1974) that would mimic the Yes SH3 domain and bind to its putative cellular targets.

In addition to YAP65, both the anti-idiotypic antibodies and antibodies generated against bacterially expressed YAP65 cDNA recognized another protein of 120 kDa. The peptide mapping analysis showed that the 120 kDa protein is not a precursor of YAP65. Although the 120 kDa protein was not detected on Western blots, we cannot presently determine whether it shares epitopes with YAP65 or whether it is a YAP65 binding protein. The former possibility seems likely since we have recently isolated a cDNA clone sharing a 3' end coding sequence with YAP65 and at the 5' end it contains a novel sequence. However, more work is required to ascertain whether it is a chimeric clone or whether it corresponds to a novel cDNA. The 120 kDa protein is not recognized by antibodies that recognize the human GAP protein (data not shown).

The YAP65 cDNA contains one long open reading frame that ends with a stop codon followed by at least two other stop codons in alternate reading frames. The sequence preceding the proposed initiation codon (first methionine) conforms to Kozak's rules for translation initiation (Kozak, 1989). However, the predicted molecular mass of the YAP65 is at least 15 kDa shorter than the YAP65 molecular mass estimated from SDS-polyacrylamide gels. There are several possible explanations of this discrepancy. One is that the present open reading frame of the cDNA is not complete and an alternative 5' upstream initiation codon is used. We have tried to prime the mRNA with YAP65 specific oligonucleotides to isolate the putative 5' sequences for the YAP65 cDNA without success. The molecular mass discrepancy may be also due to serine phosphorylation and to the unusually high content of prolines that could affect the relative migration of the YAP65 protein.

The constitutive phosphorylation of YAP65 on serine residues is a noteworthy aspect of this protein. Although a number of consensus sites for various serine kinases exist within the YAP65 protein sequence, frequently repeated X-S-P-X sequences could be phosphorylated by a proline-directed serine protein kinase (Vulliet et at., 1989; Kemp & Pearson, 1990). Mapping of the serine phosphorylation site(s) on YAP65 is in progress.

By a number of criteria, we showed that YAP65 expressed in bacteria binds in vitro to the bacterially expressed SH3 domain of Yes. We were also able to document the precipitation of the Yes kinase with purified YAP65 coupled to Sepharose beads (FIG. 6). However, we were not able to coprecipitate Yes and YAP65 using available antibodies. It is likely that these antibodies prevent complex formation by binding at or near the domains involved in the interaction.

Using synthetic peptides and bacterially expressed fusion proteins we have shown the involvement of a short proline-rich sequence of YAP65 in binding to the Yes-SH3 domain. A synthetic peptide corresponding to the proline-rich domain of YAP65 (PLAP peptide) was also able to block the recognition of YAP65 by the original anti-idiotypic antibody (not shown). In view of the fact that a large concentration (200 $\mu$M) of the PLAP peptide was required to partially compete for binding, we cannot eliminate the role of other sequences of YAP65 in binding to Yes. Especially, with the recent data on the consensus sequence for SH3 binders (Yu et al., 1994) one could identify more proline-rich sites within the YAP65 sequence, which could be involved in binding. A more obvious explanation of the inefficient competition with peptides vs efficient competition with bacterially expressed proteins is that peptides may lack the required conformation for optimal binding.

With respect to-the biological significance of the molecular interaction between YAP65 and Yes proteins, it seems that the most important aspect of this finding may relate to the possible signaling link between the Yes tyrosine kinase and YAP65 as a substrate of a serine kinase. Therefore it would be important to map the phosphorylation site(s) on YAP65, to identify a kinase responsible for the modification, and to assess the potential role of phosphorylation in the regulation of binding. Among more basic questions that remain to be answered is whether the formation of the YAP65-Yes complex affects Yes kinase activity and whether YAP65 binds to the oncogenic forms of Yes.

The four examples of SH3 domain-ligand interactions are: (i) the Abl kinase and the 3BP1 protein that shows homology to GAP-rho, (ii) Grb2 protein that links epidermal growth factor receptor to guanine nucleotide exchange factor, SOS, (iii) GTPase dynamin that is activated by binding to various proteins containing SH-3 domain(s), and (iv) Ab1 proto-oncogene kinase that binds to the first SH3 domain of Crk proto-oncogene protein (Lowenstein et al., 1992; Olivier et al., 1993; Egan et al., 1993; Gout et al., 1993; Li et al., 1993; Ren et al., 1993; Rozakis-Adcock et al., 1993; Ren et al., 1994; Feller et al., 1994). These and other recent data (Barfod et al., 1993) support the suggestion that the SH3 domain is frequently involved in the control of small, Ras-like G proteins (Pawson & Gish, 1992). Since non-receptor type protein-tyrosine kinases are known to signal through Ras (Smith et al., 1986; Gibbs et al., 1990), it would be important to reevaluate the Yes-YAP65 interaction in terms of the Ras pathway.

References

Barfod, E. T. Zheng, Y., Kuang, W. -J., Hart, M. J. Evans, T., Cerione, R. A. & Ashkenazi, A. (1993). *J. Biol. Chem.,* 268, 26059–26062.

Birge, R. B. & Hanafusa, H. (1993). *Science,* 262, 1522–1524.

Birge, R. B., Fajardo, J. E., Mayer, B. J. & Hanafusa, H. (1992). *J. Biol. Chem.,* 267, 10588–10595.

Cantley, L. C., Auger, K. R., Carpenter, C. Duckworth, B., Graziari, A., Kapeller, R. & Soltoff, S. (lggl), $^1$*Cell,* 64, 281–302.

Chen, J. K., Lane, W. S., Brauer, A. W., Tanaka, A. & Schreiber, S. L. (1993). *J. Am. Chem. Sco.,* 115, 12591–12592.

Chou, M. M., Fajardo, E. J. & Hanafusa, H. (1992). *Mol. Cell. Biol.,* 12, 5834–5842.

Chicchetti, P., Mayer, B. J., Thiel, G. & Baltimore, D. (1992). *Science,* 267, 803–806.

Clark, S. G., Stern, M. J. & Horvitz, H. R. (1992). *Nature,* 356, 340–344.

Cooper, J. A. (1990). *Peptides & Protein Phosphorylation.* Kemp, B. (ed.) CRC: Boca Raton, Fla., pp. 85–113.

Cooper, J. A. & Howell, B. (1993). *Cell,* 73, 1051–1054.

Egan, S. E., Giddings, B. W., Brooks, M. W., Buday, L., Sizeland, A. M. & Weinberg, R. A. (1993). *Nature,* 363, 45–51.

Eiseman, E. & Bolen, J. B. (1992). *Nature,* 355, 78–80.

Feller, S. M., Knudsen, B. & Hanafusa, H. (1994). *EMBO J.,* in press.

Gibbs, J. B., Marshall, M. S., Scolnick, E. M., Dixon, R. A. F. & Vogel, U.S. (1990). *J. Biol. Chem.,* 265, 20437–20442.

Gout, I., Dhand, R., Hiles, I. D., Fry, M. J., Panayotou, G., Das, P., Truong, O., Totty, F. N., Hsuan, J., Booker, G. W., Campbell, I. D. & Waterfield, M. D. (1993). *Cell,* 75, 25–36.

Hagen, F. S. & Young. E. T. (1975). *Biochemistry,* 13, 3394–3400.

Hirai, H. & Varmus, H. E. (1990). *Mol. Cell. Biol.,* 10, 1307–1318.

Huang, M. M., Bolen, J. B., Barnwell, J. W., Shatill, S. J. & Brugge, J. S. (1991). *Proc. Natl. Acad. Sci. USA,* 88, 7844–7848.

Jerne, N. K. (1974). *Ann. Immunol. (Inst. Pasteur),* 125C, 373–389.

Kanner, S. B., Reynolds, A. B., Wang, H. C. R., Vines, R. R. & Parsons, J. T. (1991). *EMBO J.,* 10, 1689–1698.

Kato, J. Y., Takeva, T., Grandori, C., Iba, H., Levy, J. B. & Hanafusa, H. (1986). *Mol. Cell. Biol.* 6, 4155–4160.

Kemp, B. E. & Pearson, R. B. (1990). *TIBS,* 15, 342–346.

Kohda, D., Hatanaka, H., Okada, M., Mandiyan, V., Ullrich, A., Schlessinger, J. & Inagaki, F. (1993). *Cell,* 72, 953–960.

Koyama, S., Yu, H., Dalgarno, D. C., Shin, T. B., Zydowsky, L. D. & Schreiber, S. L. (1993). *Cell,* 72, 945–952.

Kozak, M.. (1989). *J. Cell. Biol.,* 108, 229–241.

Kypta, R. M., Goldberg, Y., Ulug, E. T. & Courtneidge, S. A. (1990). *Cell,* 62, 481–492.

Li, N., Batzer, A., Daly, R., Yajnik, V., Skolnik, E., Chardin, P., Bar-Sagi, D., Margolis, B. & Schlessinger, J. (1993). *Nature,* 363, 85–88.

Liu, Y., Marehgere, E. M., Koch, C. A. & Pawson, T. (1993). *Mol. Cell. Biol.,* 13, 5225–5232.

Lowenstein, E. J., Daly, R. J., Batzer, A. G., Li, W., Margolis, B., Lammers, R., Ullrich, A., Skolnik, E. Y., Bar, S. D. & Schlessinger, J. (1992). *Cell,* 70, 431–442.

Margolis, B. (1992). *Cell Growth Diff.,* 3, 73–80.

Mayer, B. & Baltimore, D. (1993). *Trends Cell Biol.,* 3, 8–13.

Merrifield, R. B. (1963). *Science,* 85, 2149–2154.

Musacchio, A., Gibson, T., Lehto, V. P. & Saraste, M. (1992a). *FEBS Lett.,* 307, 55–61.

Musacchio, A., Noble, M., Pauptit, R., Wierenga, R. & Saraste, M. (1992b). *Nature,* 359, 851–855.

Nemeth, S. P., Fox, L. C., DeMarco, M. & Brugge, J. S. (1989). *Mol. Cell. Biol.* 9, 1109–1119.

Noble, M. E., Musacchio, A., Saraste, M., Courtneidge, S. A. & Wierenga, R. K. (1993). *EMBO J.,* 12, 2617–2624.

Olivier, J. P., Raabe, T., Henkemeyer, M., Dickson, B., Mbamalu, G., Margolis, B. & Schlessinger, J., Hafen, E. & Pawson, T. (1993). *Cell,* 73, 179–191.

Parsons, S. J., McCarley, D. J., Raymond, V. W. & Parsons, T. J. (1986). *J. Virol.,* 59, 755–758.

Pawson, T. & Gish, G. D. (1992). *Cell,* 71, 359–362.

Pawson, T. & Schlessinger, J. (1993). *Curr. Biol.,* 3, 434–442.

Potts, W. M., Reynolds, A. B., Lansing, T. J. & Parsons, J. T. (1988). *Oncogene Res.,* 3, 343–355.

Ren, R., Ye, Z. S. & Baltimore, D. (1994). *Genes & Develop,* in press.

Ren, R., Mayer, B. J., Cicchetti, P. & Baltimore, D. (1993). *Science,* 259, 1157–1161.

Roussel, R. R., Brodeur, S. R., Shalloway, D. & Laudano, A. P. (1991). *Proc. Natl. Acad. Sci. USA,* 88, 10696–10700.

Rozakis-Adcock, M., Fernley, R., Wade, J., Pawson, T. & Bowtell, D. (1993). *Nature,* 363, 83–85.

Sanger, F., Niklen, S. & Coulson, A. R. (1977). *Proc. Natl. Acad. Sci. USA,* 74, 5463–5467.

Seidel-Dugan, C., Meyer, B. E., Thomas, S. M. & Brugge, J. S. (1992). *Mol. Cell. Biol.,* 12, 1835–1845.

Smith, M. R., DeGudicibus, J. S. & Stacy, D. W. (1986). *Nature,* 320, 540–543.

Strosberg, A. D. (1989). *Methods In Enzymol.,* 178, 265–275.

Sudol, M. (1993). *The Molecular Basis of Cancer,* Neel, B., & Kumar, R. (eds). Futura: NY, pp. 203–224.

Sudol, M., Greulich, H., Newman, L., Sarkar, A., Sukegawa, J. & Yamamoto, T. (1993). *Oncogene,* 823–831.

Sudol, M. (1989). *J. Neurosci. Res.* 24, 1–8.

Sudol, M., Kuo, F. C., Shigemitsu, L. & Alvarez-Buylla, A. (1989). *Mol. Cell. Biol.,* 9, 4545–4549.

Sudol, M., Kieswetter, C., Zhao, Y. -H., Dorai, T., Wang, L. -H. & Hanafusa, H. (1988). *Nucl. Acid. Res.,* 16, 9876.

Sudol, M. & Hanafusa, H. (1986). *Mol. Cell. Biol.,* 6, 2839–2846.

Sudol, M. & Reich, E. (1984). *Biochem. J.,* 219, 971–978.

Vulliet, P. R., Hall, F. L., Mitchell, J. P. & Hardie, D. G. (1989). *J. Biol. Chem.,* 264, 16292–16298.

Wages, D. S., Keefer, J., Rall, T. B. & Weber, M. J. (1992). *J. Virol.,* 66, 1866–1874.

Weng, Z., Taylor, J. A., Turner, C. E., Brugge, J. S. & Seidel-Dugan, C. (1993). *J. Biol. Chem.,* 268, 14956–14963.

Willott, E., Balda, M. S., Fanning, A. S., Jameson, B., Itallie, C. V. & Anderson, J. M. (1993). *Proc. Natl. Acad. Sci. USA,* 90, 7834–7838.

Williamson, M. P. (1994). *Biochem. J.,* 297, 249–260.

Young, R. A. & Davis, R. W. (1983). *Proc. Natl. Acad. Sci. USA,* 80, 1194–1198.

Yu, H., Rosen, M. K., Shin, T. B., Seidel-Dugan, C., Brugge, J. S. & Schreiber, S. L. (1992). *Science,* 258, 1665–1668.

Yu, H., Chen, J. K., Feng, S., Dalgarno, D. C., Brauer, A. W. & Schreiber, S. L. (1994). *Cell,* 76, 933–945.

EXAMPLE 2: Isolation of Human and Murine YAPs

Experimental Procedures cDNA Cloning and Sequencing—A cDNA of chicken YAP corresponding to the coding region was used as a probe to screen a lambda pCEV 15 cDNA library derived from M426 human lung embryonic fibroblast cells and a 16 day mouse embryo cDNA library in lambda Ex1oxTM (purchased from Novagen, Madison, Wis.). The low stringency conditions of hybridization were as follows: 5×SSPE, 10×Denhart, 2% SDS, 0.2 mg/ml of salmon sperm DNA and 106 cpm/ml of $^{32}$P-labeled cDNA at 65° C. overnight. The filters were washed 2× for 20 min. at room temperature with 2×SSC, 0.05% SDS, and 2×at 60° C. for 20 min. with 0.1 SSC, 0.1 % SDS. Both libraries contained phages with a plasmid part that carried the insert. The plasmids with inserts were easily rescued from the lambda genome following published protocols. The apparently complete sequence of the human YAP cDNA was contained in one recombinant plasmid pCEV 15-HYAP6 with a SalI—SalI insert of 5 kb pairs. The sequence of mouse YAP cDNA was reconstituted with two overlapping clones contained in pEX1ox-MYAP6 (2.3 kb EcoRI-HindIII insert) and pEX1ox-MYAP20 (EcoRI-HindIII insert). Both strands of the cDNA clones were analyzed by direct sequence analysis using the Sanger method.

Southern and Northern Blot Analysis—southern blot on genomic DNA from nine eukaryotic species was performed using the same conditions as for cDNA library screening. DNA sources were as follows: human, Rhesus monkey, Sprague-Dawley rat, BALB/c mouse, dog, cow, rabbit, chicken and *Saccharonyces cerevisiae*. Except for yeast DNA and human DNA, all genomic DNAs were isolated from kidney tissue. Human DNA was isolated from placental tissue. DNA was digested with EcoRI, run on a 0.7% agarose gel, transferred to a charge-modified nylon membrane by blotting and fixed by UW irradiation. The cDNA inserts of the HYAP5 plasmid or human beta-actin cDNA control probe were radioactively labelled to a specific activity of approximately 2×108 cpm/ug and were used as a probe for Southern (HYAP probe) and for Northern analysis (HYAP probe first, and after striping the probe for beta actin). Poly A$^+$ RNAs were isolated from 16 different human tissues. The age and sex of tissue donors varied but all tissues, as far as could be determined, were free of disease (Clontech Lab, Inc. Palo Alto, Calif.). The RNA (2 μg per lane) were run on a denaturing formaldehyde 1.2% agarose gel, transferred to a charge-modified nylon membrane by blotting and fixed by UV irradiation. The hybridization conditions were: 5×0 SSPE, 10 Denhardt's solution, 100 μg/ml of freshly denatured, sheared salmon sperm DNA, 50% formaldehyde and 2% SDS at 42° C. overnight. The blots were washed for 30 min. at room temperature in 2×SSC, 0.05% SDS and for 1 hour at 50° C. in 0.1×SSC, 0.1 % SDS. Removal of the HYAP probe from the blot for subsequent hybridization with the human beta-actin probe was by incubating the blot for 10 min. in sterile $H_2O$, 0.5% SDS that was heated to 90° C.

Chromosomal Localization—For Southern blot hybridization, the cDNA insert was isolated and radiolabeled by random priming to a specific activity of $10^8$ cpm/0.1 vg and $10^8$ cpm were used for each filter hybridization; for FISH, the entire cDNA containing plasmid was labeled with biotin by nick translation.

Hybrid DNAs were from previously described rodent-human hybrid cell lines (Huebner et al., 1991; Lou et al., 1993, Nagarajan et al., 1986) or from the NIGMS Human Genetic Mutant Cell Repository (Coriell Institute, Camden, N.J.). Hybrids retaining partial chromosomes 11 and 6 have also been described (Lou et al., 1993; Nagarajan et al., 1986). Hybrid DNAs were tested for presence of YAP65 specific human Sst1 and Pst1 restriction fragments detected by radiolabeled YAP65 probe using standard Southern hybridization methods.

Chromosomal Fluorescence In Situ Hybridization (FISH). The procedure used in this study has been described in detail (Lou et al., 1993). Probes were prepared by nick translation using biotin-labeled 11-dUTP (Bionick kit, BRL). Hybridization of biotin-labeled probes was detected with fluorescein isothiocyanate-conjugated avidin. Metaphase chromosomes were identified by Hoechst-33528 staining and UV irradiation (365nm), followed by 4,' g-diamidino-2-phenylindole (DAPI) staining to produce the banding pattern. The fluorescent signal was observed with filter block 13 BP450–490/LP515; Leitz Orthoplan) on the background of red chromosomes stained with propidium iodide. Q-banding was observed with filter block A (BP340–380/LP430).

Computer-Aided Analysis of Protein Sequences—Searches of sequence homology were performed through the FASTA and FASTP programs in GenBank. The secondary structures of the polypeptides were predicted using the program PHD. The probability of matching the alignment by chance was computed using the MoST program.

Results

Cloning of Human and Chicken YAPs—Using a cDNA fragment encoding the chicken YAP as a probe, we screened lambda phage plaques of a human lung embryonic fibroblast cDNA library. Of 13 positive clones, two (HYAP5 and HYAP6) with the longest inserts (approximately 3 and 5 kb long, respectively) were analyzed further. Initial analysis of the DNA sequence showed that HYAP5 cDNA is included with the HYAP6 clone. The result of direct sequence analysis of both strands of the HYAP6 cDNA is shown in FIG. 7.

The longest open reading frame predicted a protein product of 493 amino acids with significant sequence similarity to the chicken YAP (FIG. 8). In parallel experiments, we isolated a mouse ortholog of YAP using the same chicken YAP cDNA as a probe. We screened a mouse embryo (16 day) cDNA library in lambda Exlox vector. Of 7 positive clones, two (MYAP6 and MYAP20) were shown to contain long inserts (approximately 2.3 and 3.6 kb long, respectively) and the clones overlapped giving rise to a 4kb long cDNA sequence terminating with a polyA stretch. Similar to the human YAP, the longest open reading frame predicted a protein product with significant sequence similarity to the chicken YAP. However, an extra insert sequence of approximately 40 amino acids was present in the middle of the sequence (FIG. 8). Visual inspection of the insert sequence suggested that it is an imperfect duplication of a sequence found upstream (see underlined sequences in FIGS. 7 and 8).

We have subjected this sequence to a more extensive analysis and found that the motif shares significant sequence and putative structure similarities with sequences found in various regulatory and signalling proteins (see below). The alignment of the chicken YAP, MYAP and HYAP also revealed long stretches of amino acid sequences that were perfectly conserved. Interestingly, the proline-rich sequence (FIG. 8, indicated with #), implicated in binding between chicken YAP and SH3 domain of Yes, is conserved among the three sequences.

Southern Blot with Various Eucaryotic DNAs—A high degree of sequence similarity between HYAP, MYAP and chicken YAP was confirmed by Southern blot analysis of the genomic DNAs digested with EcoRI enzyme (FIG. 9). Genomic DNA from other higher eucaryotes also showed hybridization with the HYAP radioactive probe. However, no specific signal was detected in yeast *Saccharoniyces cerevisiae*.

Northern Blot Analysis—A major band of approximately 5 kb was detected in various human tissues. In addition a band migrating below the 2.4 kb mark was also detected in some of the tissues (see FIG. 10, lanes K, M and O for example). The expression of HYAP mRNA is rather ubiquitous, being relatively high in placenta, prostate, testis, ovary and small intestine (FIG. 10, lanes C, K, L, M, N). Relatively lower levels of the message were found in the brain, liver and spleen (FIG. 10, lanes B, E, I). We could not detect HYAP mRNA in the preparation of human peritoneal blood leukocytes even if the blot was overexposed (FIG. 10, lane P).

Chromosomal localization—The HYAP cDNA detected two loci, one on chromosome 11 (11q13) and another on chromosome 6 (6q23-qter). When human DNA was digested with SstI restriction enzyme and probed with radioactive HYAP cDNA, two strongly hybridizing bands one of 16 kbp and another migrating above 23 the kbp mark were detected (not shown). In addition, we also observed less strongly hybridizing bands. In the same analysis, rodent DNA digested with SstI and probed with HYAP cDNA showed fainter bands distinguishable from the HYAP specific fragments (not shown). When DNAs from a panel of rodent-human hybrids, each carrying a few human chromosomes, were tested for the presence of HYAP locus, it was observed that the two strongly hybridizing bands segregated independently and thus were on different chromosomes (not shown). The results of the more extensive analysis of the rodent-human hybrid panel are summarized in FIG. 11A. These data illustrate that one HYAP specific locus maps to chromosome 11 and another to chromosome 6. The less strongly hybridizing bands did not seem to segregate with either of the two major bands. The locus on chromosome 11 q was the most intensely hybridizing band and was thus presumed to represent the cognate YAP65 gene. To define the chromosome positions of these loci more narrowly, small panels of DNAs from hybrids carrying partial chromosomes 11 or 6 were also tested for the presence of the YAP65 loci with the results summarized in FIG. 11B. Because the HYAP cognate locus is present in hybrid 7298 but absent in hybrid Cer, the gene maps between the centromere and the BCL1 locus whereas the HYAP related locus maps to 6p21 to 6qter.

To confirm the above data, fluorescent in situ hybridization (FISH) with the HYAP65 cDNA probe to normal human metaphases was performed. Using FISH we detected 51 signals at 11q13 on 27 metaphases and only 12 signals on the q terminal ⅓ of chromosome 6. The FISH results are summarized to the left of the chromosome idiogram shown in FIG. 11B.

Since the HYAP65 gene mapped to 11q13, centromeric to the BCL1 major breakpoint region, possibly within the chromosomal region which is amplified in a significant fraction of human mammary carcinomas, a panel of 17 mammary carcinoma cell line DNAs was tested for evidence of amplification of the HYAP65 gene. Four of these DNAs had shown amplification of the CCND1 gene (from 3 to 10-fold) but none showed evidence of amplified HYA65 gene (data not shown). Thus, the HYAP65 gene is most likely centromeric to the chromosome region commonly amplified at 11q13 in mammary carcinomas.

The YAP65 gene maps to 11q13 centromeric to the BCL1 locus and could thus be near the locus for the multiple endocrine neoplasia type 1 familial gene (MEN1, cited in Schinzel et al., 1993); also, genes in the 11q13 band map to mouse chromosome 19 or 7 with the centromere proximal loci on mouse 19 (summarized in O'Brien, et al., 1993). Thus, the murine YAP65 gene is likely to map to mouse chromosome 19 but could be on mouse chromosome 7.

References for Example 2

Benovic, J. L., Stone, W. C., Huebner, K., Croce, C., Caron, M. G. and Lefkowitz, R. J.

cDNA cloning and chromosomal localization of the human β-adrenergic receptor kinase. FEBs, Letters 283:(1) 122–126, 1991.

Huebner, K., Druck, T., Croce, C. M. and Thiesen, H. -J. Twenty-seven nonoverlapping zinc finger cDNAs from human T-cells map to nine different human chromosomes with apparent clustering. Am. J. Hum. Genet. 48:726–740, 1991.

Lou, Z., Kastury, K., Crilley, P., Lasota, J., Druck, T., Croce, C. M. and Huebner, K. Characterization of bone marow derived closed circular DNA clones. Genes, Chrom. Cancer 7:15–27, 1993.

Nagarajan, L., Louie, E., Tsujimoto, Y., Balduzzi, P. C., Huebner, K. and Croce, C. M. The human c-ros gene (ROS) is located at chromosome region 6q16–6q22. Proc. Natl. Acad. Sci. USA, 83:6568–6572, 1986.

O'Brien, S. J., Peters, J., Searle, A., Womack, J. and Marshall-Gram, J. Report of the committee on comparative gene mapping, 758–809, Chromosome Coordinating Meeting (1992); Cuticehia, A. J., Pearson, P. L., Klinger, A. P., (eds); Genome Priority Reports, Vol. 1 Basel, Karger, 1993.

Schinzel, A., Frezal, J. and McKusick, V. A. Report of the committee for clinical disorders, chromosome aberrations and uniparental dismay, 658–699, Chromosome Coordinating Meeting (1992); Cuticehia, A. J., Pearson, P. L., Klinger, A.P>(eds); Genome Priority Reports, Vol. 1 Basel, Karger, 1993.

Miki, T., Matsui, T., Heidaran, M. A. and Aaronson, S. A. (1989) Gene, 83, 137–146.

Palazzolo, M. J., Hamilton, B. A., Ding, D., Martin, C. A., Raghavan, K. V., Mierendorf, R. C., Mead, D. A., Meyerowitz, E. M., and Lipschitz, H. D. (1990) Gene 88, 25–36.

EXAMPLE 3: Identification of a Signalling Site

Duchenne and Becker muscular dystrophies are degenerative diseases caused by mutations of a single locus, the dystrophin gene (for review, see Ahn and Kunkel, 1993, Nature Genetics 3:283–291). The gene encodes a large molecule that belongs to a family of cytoskeletal proteins including α-actinin and β-spectrin. Different splicing forms exist; the longest form consists of four domains: i) an N-terminal, globular actin-binding domain common to other cytoskeletal proteins; ii) twenty-four spectrin-like repeats forming a long rod in the middle of the molecule; iii) a cysteine-rich calcium-binding domain; and iv) a C-terminal globular domain (Ahn and Kunkel, 1993, supra) (FIG. 12). Molecular analysis of the central rod-like portion of human dystrophin revealed two interruptions of the spectrin repeats and two flanking segments which appear to be hinge regions (Koenig and Kunkel, 1990, J. Biol. Chem. 265:4560–66).

Since the flanking hinge regions are sufficiently long to form functionally independent domains, they have been subjected to sequence database searches. The segment following the spectrin repeats indeed showed significant sequence similarity to repeats in a nematode and in a mouse protein (Yo61 and Nedd-4 in FIG. 13): the probability of a chance match was less than $10^{-6}$, as computed using the program Blastp (Altschul et al., 1990, J. Mol. biol. 215:403–410). Subsequent database searches with profiles (Gribskov et al, 1987, Proc. Natl. Acad. Sci. USA 84:4355–58) and patterns (Rhode and Bork, 1993, CABIOS 9:183–189) derived from these regions identified several other proteins which contain this novel domain. Some of the proteins have as many as three copies (FIG. 13). Since the two strictly conserved tryptophans (W in the single letter amino acid code) give the strongest signal at the sequence level, this domain was termed the WW domain. Instrumental to delineation of the WW domain was the cloning of the YAP gene.

As noted above, the mouse YAP protein contains two WW domains compared to only one found in the human and chicken orthologs. The second WW domain in the mouse sequence appears to be the result of a recent duplication and thus allows the length of the domain to be estimated at about 40 amino acids.

The WW domain is often flanked by histidine- or cysteine-rich regions that might bind metal ions, as in dystrophin (Ahn and Kunkel, 1993, supra). The domain itself appears to contain β-strands (FIG. 13) grouped around four conserved aromatic positions. The presence of both a hydrophobic core and numerous charged residues (FIG. 13) is reminiscent of well-characterized protein modules involved in protein-protein interactions. Like the SH2, SH3, and PH domains, the WW domain occurs in a variety of molecules whose functions do not have a specific common denominator. Despite their functional diversity, all of the proteins listed in FIG. 13 seem to be involved in signalling (or regulatory) functions.

Dystrophin and utrophin are more that 70% identical in sequence (Ahn and Kunkel, 1993, supra); they form tetramers via their spectrin-like repeats and are thought to have multiple functions including involvement in membrane stability, transduction of contractile forces to extracellular environment, and organization of membrane specialization (Ahn and Kunkel, 1993, supra). YAP is a substrate of an unknown serine kinase, and it binds to the SH3 domain of the Yes proto-oncogene product via a proline-rich region located downstream of the WW domain (see Example 1, supra) (FIG. 12). Mouse Nedd4 plays a role in the embryonic development and differentiation of the central nervous system (Kumar et al., 1992, Bioch. Biophys. Res. Comm. 185:1155–61). Yeast Rsp5 is similar to Nedd-4 in molecular organization and contains an N-terminal regulatory domain common to protein kinases C and synaptogamins (C2-domain in the PROSITE motif database). The yeast Ess1 protein appears to be essential for growth and may be involved in cytokinesis and or cell separation (Hanes et al., 1989, Yeast 5:55–72). Rat FE65 is a transcription factor activator expressed preferentially in liver. The activator factor domain is located within the first 232 residues of FE65 (Duilio et al., 1991, Nucl. Acid. Res. 19:5269–74). This region also contains the WW domain.

The identification of the WW domain in dystrophin suggests a binding site for one of the many dystrophin-associated proteins (Tinsley et al., 1994, Proc. Natinoal Acad. Sci USA 91:8307–13). It is closely located to the β-dystroglycan binding site and may regulate the formation of this complex.

EXAMPLE 4: Expression of WW Domains cDNA clones for human dystrophin WW domain and human YAP WW domain were inserted in the pGEX-2TK vector (Pharmacia) and expressed as fusion proteins with a GST domain and a phosphorylation site introduced. These vector constructs are depicted in FIG. 14A and B, respectively. The recombinant WW domains were expressed, labeled with $^{32}$P-ATP, and used to screen a 16 day old embryo mouse cDNA expression library.

To date, two clones have been isolated. One is 1.6 kB, the other is 0.5 kB. Preliminary and partial sequence data suggest that these clones encode two novel proteins. Sequence analysis indicates that they are not related to each other, and there is no significant degree of sequence similarity with any of the sequences available in Genbank.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

It is also to be understood that all base pair sizes given for nucleotides are approximate and are used for the purpose of description.

Various references are cited herein, the disclosures of which are incorporated by reference herein in their entirety.

What is claimed is:

1. An isolated nucleic acid that encodes a Yes proto-oncogene associated protein or polypeptide (YAP); wherein said YAP has the amino acid sequence of SEQ ID NO:2.

2. The nucleic acid of claim 1 containing the coding sequence of the nucleotide sequence of SEQ ID NO:1.

3. An isolated nucleic acid that encodes a Yes proto-oncogene associated protein or polypeptide (YAP); wherein said YAP has the amino acid sequence of SEQ ID NO:4.

4. The nucleic acid of claim 3 containing the coding sequence of the nucleotide sequence of SEQ ID NO:3.

5. An isolated nucleic acid that encodes a Yes proto-oncogene associated protein or polypeptide (YAP); wherein said YAP has the amino acid sequence of SEQ ID NO:5.

6. An isolated nucleic acid that encodes a peptide consisting of the amino acid sequence selected from the group consisting of SEQ ID NO: 6, SEQ ID NO:7, SEQ ID NO:8, SEQ NO:9, SEQ ID NO:10, SEQ ID NO:11, SEQ ID NO:12, SEQ ID NO:13, SEQ ID NO: 14, SEQ ID NO:15, SEQ ID NO:16, SEQ ID NO:17, SEQ ID NO:18, SEQ NO:19, SEQ ID NO: 20, SEQ ID NO:21, SEQ ID NO:21, SEQ ID NO:22, SEQ ID NO:23, SEQ ID NO:24, and SEQ ID NO:25.

7. The nucleic acid on claim 6, encoding a peptide consisting of the amino acid sequence selected from the group consisting of SEQ ID NO:6, SEQ ID NO:9, SEQ ID NO:10, SEQ ID NO:11 and SEQ ID NO:12.

8. An isolated nucleic acid encoding a chimeric polypeptide consisting of a fusion protein and a fusion peptide; wherein the fusion protein contains a non-YAP or non-WW domain protein, or a portion thereof; wherein the fusion peptide consists of 30 to 50 amino acid residues comprising a WW domain; and wherein said fusion peptide consists of the amino acid sequence selected from the group consisting of SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, and using SEQ ID NO:25.

9. The nucleic acid of claim 8 wherein the fusion protein is glutathione-S-transferase.

10. The nucleic acid of claim 8 selected from the group consisting of DNA and RNA.

11. A cloning vector comprising the nucleic acid molecule of claim 10.

12. A host cell transfected or transformed with the cloning vector of claim 11.

13. The host cell of claim 12 which is a bacterium.

14. An expression vector comprising the isolated nucleic acid of claim 8 operatively associated with an expression control sequence.

15. A host cell transfected or transformed with the expression vector of claim 14.

16. The host cell of claim 15 which is selected from the group consisting of a bacterium, a yeast, an insect cell, and a mammalian cell.

17. A method for producing a chimeric polypeptide, comprising:
   (a) culturing the host cell of claim 15 under conditions that allow for expression of the YAP protein or polypeptide; and
   (b) recovering the expressed YAP protein or polypeptide.

18. The nucleic acid of claim 6 selected from the group consisting of DNA and RNA.

19. A cloning vector comprising the nucleic acid molecule of claim 18.

20. A host cell transfected or transformed with the cloning vector of claim 19.

21. The host cell of claim 20 which is a bacterium.

22. An expression vector comprising the isolated nucleic acid of claim 6 operative associated with an expression control sequence.

23. A host cell transfected or transformed with the expression vector of claim 22.

24. The host cell of claim 23 which is selected from the group consisting of a bacterium, a yeast, an insect cell, and a mammalian cell.

25. A method for producing a peptide consisting of 30 to 50 amino acid residues containing a WW domain, comprising:
   (a) culturing the host cell of claim 23, under conditions that allow for expression of the peptide; and
   (b) recovering the expressed peptide.

26. The nucleic acid of claim 3 selected from the group consisting of DNA and RNA.

27. A cloning vector comprising the nucleic acid molecule of claim 26.

28. A host cell transfected or transformed with the cloning vector of claim 27.

29. The host cell of claim 28 which is a bacterium.

30. An expression vector comprising the isolated nucleic acid of claim 3 operatively associated with an expression control sequence.

31. A host cell transfected or transformed with the expression vector of claim 30.

32. The host cell of claim 31 which is selected from the group consisting of a bacterium, a yeast, an insect cell, and a mammalian cell.

33. A method for producing a YAP protein or polypeptide, comprising:
   (a) culturing the host cell of claim 31 under conditions that allow for expression of the YAP protein or polypeptide; and
   (b) recovering the expressed YAP protein or polypeptide.

* * * * *

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 1512 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vii) IMMEDIATE SOURCE:
      (B) CLONE: YAP (ix) FEATURE:
      (A) NAME/KEY: CDS
      (B) LOCATION: 66..1410

(xi) SEQUENCE DESCRIPTION: SEQ ID NO:1:

```
GAATTCCCCG AGCACACAGA GCCATCGAGC CCCGCGAGGA AGCGCCAGGG GGTCCCGCCG        60

CAGCC ATG GAT CCC GGG CAG CCT CAG CCG CAG CAG CCG CCG CAG GCG          107
      Met Asp Pro Gly Gln Pro Gln Pro Gln Gln Pro Pro Gln Ala
       1               5                  10

GCG CAG CCC CCG GCC CCG CAG CAG GCG GCC CCG CAG CCC CCG GGC GCG        155
Ala Gln Pro Pro Ala Pro Gln Gln Ala Ala Pro Gln Pro Pro Gly Ala
 15                  20                  25                  30

GGG TCG GGA GCT CCG GGA GGC GCC GCG CAG CCG CCG GGC GCG GGG CCC        203
Gly Ser Gly Ala Pro Gly Gly Ala Ala Gln Pro Pro Gly Ala Gly Pro
                 35                  40                  45

CCT CCG GCG GGG CAC CAG ATC GTC CAT GTG CGG GGC GAC TCC GAG ACC        251
Pro Pro Ala Gly His Gln Ile Val His Val Arg Gly Asp Ser Glu Thr
             50                  55                  60

GAC CTG GAG GCT CTC TTC AAC GCC GTG ATG AAC CCC AAG GGC GCC AAC        299
Asp Leu Glu Ala Leu Phe Asn Ala Val Met Asn Pro Lys Gly Ala Asn
 65                  70                  75

GTG CCG CAC ACG CTG CCC ATG CGG CTC CGC AAG CTG CCG GAC TCC TTC        347
Val Pro His Thr Leu Pro Met Arg Leu Arg Lys Leu Pro Asp Ser Phe
         80                  85                  90

TTC AAG CCG CCC GAG CCC AAA GCT CAC TCC CGC CAG GCC AGC ACT GAC        395
Phe Lys Pro Pro Glu Pro Lys Ala His Ser Arg Gln Ala Ser Thr Asp
 95                  100                 105                 110

GCA GGG ACA GCA GGA GCC CTG ACC CCT CAG CAT GTT CGT GCT CAT TCC        443
Ala Gly Thr Ala Gly Ala Leu Thr Pro Gln His Val Arg Ala His Ser
                 115                 120                 125

TCT CCA GCA TCA CTG CAG CTG GGG GCC GTC TCC CCT GGG ACG CTC ACA        491
Ser Pro Ala Ser Leu Gln Leu Gly Ala Val Ser Pro Gly Thr Leu Thr
             130                 135                 140

CCC TCC GGA GTA GTG ACC GGA CCC GGA GCT CCG TCT TCT CAG CAT CTC        539
Pro Ser Gly Val Val Thr Gly Pro Gly Ala Pro Ser Ser Gln His Leu
         145                 150                 155

CGC CAG TCT TCA TTT GAG ATC CCT GAT GAT GTA CCT CTG CCA CCG GGC        587
Arg Gln Ser Ser Phe Glu Ile Pro Asp Asp Val Pro Leu Pro Pro Gly
 160                 165                 170

TGG GAG ATG GCC AAA ACA CCA TCT GGA CAG AGA TAC TTC CTT AAT CAT        635
Trp Glu Met Ala Lys Thr Pro Ser Gly Gln Arg Tyr Phe Leu Asn His
175                  180                 185                 190
```

```
ATT GAT CAA ACA ACA ACA TGG CAA GAT CCC AGG AAG GCC ATG CTT TCC      683
Ile Asp Gln Thr Thr Thr Trp Gln Asp Pro Arg Lys Ala Met Leu Ser
            195                 200                 205

CAG ATG AAC GTT ACA GCT CCC ACC AGT CCT CCC GTG CAA CAG AAC TTA      731
Gln Met Asn Val Thr Ala Pro Thr Ser Pro Pro Val Gln Gln Asn Leu
            210                 215                 220

ATG AAC TCA GCA TCA GCC ATG AAT CAG CGC ATC AGC CAA AGT GCT CCA      779
Met Asn Ser Ala Ser Ala Met Asn Gln Arg Ile Ser Gln Ser Ala Pro
            225                 230                 235

GTG AAA CAG CCA CCC CCT CTG GCT CCT CAG AGT CCC CAA GGT GGT GTC      827
Val Lys Gln Pro Pro Pro Leu Ala Pro Gln Ser Pro Gln Gly Gly Val
            240                 245                 250

ATG GGT GGG AGT AGC TCC AAT CAG CAA CAA CAG ATG AGA CTT CAG CAG      875
Met Gly Gly Ser Ser Ser Asn Gln Gln Gln Gln Met Arg Leu Gln Gln
255                 260                 265                 270

CTA CAG ATG GAG AAG GAA AGG CTG AGA CTG AAG CAT CAA GAA CTG CTT      923
Leu Gln Met Glu Lys Glu Arg Leu Arg Leu Lys His Gln Glu Leu Leu
            275                 280                 285

CGG CAG GAA TTG GCT CTC CGT AGC CAG CTT CCA ACG ATG GAA CAA GAT      971
Arg Gln Glu Leu Ala Leu Arg Ser Gln Leu Pro Thr Met Glu Gln Asp
            290                 295                 300

GGT GGA TCT CAA AAT CCC GTA TCA TCT CCT GGA ATG TCT CAG GAA CTG     1019
Gly Gly Ser Gln Asn Pro Val Ser Ser Pro Gly Met Ser Gln Glu Leu
            305                 310                 315

AGG ACT ATG ACT ACA AAT AGT TCT GAT CCC TTT CTT AAC AGT GGA ACA     1067
Arg Thr Met Thr Thr Asn Ser Ser Asp Pro Phe Leu Asn Ser Gly Thr
320                 325                 330

TAT CAC TCC AGA GAT GAA AGC ACA GAT AGC GGA CTT AGC ATG AGC AGT     1115
Tyr His Ser Arg Asp Glu Ser Thr Asp Ser Gly Leu Ser Met Ser Ser
335                 340                 345                 350

TAC AGC GTA CCC AGA ACC CCC GAT GAC TTC CTG AAC AGT GTT GAT GAG     1163
Tyr Ser Val Pro Arg Thr Pro Asp Asp Phe Leu Asn Ser Val Asp Glu
            355                 360                 365

ATG GAT ACA GGT GAC AGT ATC AGC CAA AGT AAC ATA CCG TCC CAT CAG     1211
Met Asp Thr Gly Asp Ser Ile Ser Gln Ser Asn Ile Pro Ser His Gln
            370                 375                 380

AAC CGA TTC CCA GAC TAC CTT GAA GCC ATT CCA GGG ACA AAT GTG GAC     1259
Asn Arg Phe Pro Asp Tyr Leu Glu Ala Ile Pro Gly Thr Asn Val Asp
            385                 390                 395

CTT GGG ACA CTG GAA GGA GAT GGG ATG AAT ATA GAA GGA GAA GAA CTG     1307
Leu Gly Thr Leu Glu Gly Asp Gly Met Asn Ile Glu Gly Glu Glu Leu
400                 405                 410

ATG CCA AGT CTG CAA GAG GCT TTG AGC TCT GAC ATC CTA AAT GAC ATG     1355
Met Pro Ser Leu Gln Glu Ala Leu Ser Ser Asp Ile Leu Asn Asp Met
415                 420                 425                 430

GAA TCT GTC TTG GCA GCC ACC AAG CCA GAT AAA GAG AGT TTT CTT ACT     1403
Glu Ser Val Leu Ala Ala Thr Lys Pro Asp Lys Glu Ser Phe Leu Thr
                435                 440                 445

TGG TTA TAG GGGCCTCA GGGAGACTGA ATTCAATCTG TCTTGGCAGC CACCAAGCCA    1460
Trp Leu *
GATAAAGAGA GTTTTCTTAC TTGGTTATAG GGGCCTCAGG GAGACTGAAT TC          1512

(2) INFORMATION FOR SEQ ID NO:2:

(i) SEQUENCE CHARACTERISTICS:
        (A) LENGTH: 448 amino acids
        (B) TYPE: amino acid
        (D) TOPOLOGY: linear (ii) MOLECULE TYPE: protein (xi) SEQUENCE DESCRIPTION: SEQ ID NO:2:
```

```
Met Asp Pro Gly Gln Pro Gln Pro Gln Pro Pro Gln Ala Ala Gln
 1               5                  10                  15

Pro Pro Ala Pro Gln Gln Ala Ala Pro Gln Pro Pro Gly Ala Gly Ser
            20                  25                  30

Gly Ala Pro Gly Gly Ala Ala Gln Pro Pro Gly Ala Gly Pro Pro Pro
            35                  40                  45

Ala Gly His Gln Ile Val His Val Arg Gly Asp Ser Glu Thr Asp Leu
         50                  55                  60

Glu Ala Leu Phe Asn Ala Val Met Asn Pro Lys Gly Ala Asn Val Pro
65                   70                  75                  80

His Thr Leu Pro Met Arg Leu Arg Lys Leu Pro Asp Ser Phe Phe Lys
                 85                  90                  95

Pro Pro Glu Pro Lys Ala His Ser Arg Gln Ala Ser Thr Asp Ala Gly
                100                 105                 110

Thr Ala Gly Ala Leu Thr Pro Gln His Val Arg Ala His Ser Ser Pro
            115                 120                 125

Ala Ser Leu Gln Leu Gly Ala Val Ser Pro Gly Thr Leu Thr Pro Ser
130                 135                 140

Gly Val Val Thr Gly Pro Gly Ala Pro Ser Ser Gln His Leu Arg Gln
145                 150                 155                 160

Ser Ser Phe Glu Ile Pro Asp Asp Val Pro Leu Pro Pro Gly Trp Glu
                165                 170                 175

Met Ala Lys Thr Pro Ser Gly Gln Arg Tyr Phe Leu Asn His Ile Asp
                180                 185                 190

Gln Thr Thr Thr Trp Gln Asp Pro Arg Lys Ala Met Leu Ser Gln Met
            195                 200                 205

Asn Val Thr Ala Pro Thr Ser Pro Pro Val Gln Gln Asn Leu Met Asn
210                 215                 220

Ser Ala Ser Ala Met Asn Gln Arg Ile Ser Gln Ser Ala Pro Val Lys
225                 230                 235                 240

Gln Pro Pro Pro Leu Ala Pro Gln Ser Pro Gln Gly Gly Val Met Gly
                245                 250                 255

Gly Ser Ser Ser Asn Gln Gln Gln Gln Met Arg Leu Gln Gln Leu Gln
                260                 265                 270

Met Glu Lys Glu Arg Leu Arg Leu Lys His Gln Glu Leu Leu Arg Gln
            275                 280                 285

Glu Leu Ala Leu Arg Ser Gln Leu Pro Thr Met Glu Gln Asp Gly Gly
290                 295                 300

Ser Gln Asn Pro Val Ser Ser Pro Gly Met Ser Gln Glu Leu Arg Thr
305                 310                 315                 320

Met Thr Thr Asn Ser Ser Asp Pro Phe Leu Asn Ser Gly Thr Tyr His
                325                 330                 335

Ser Arg Asp Glu Ser Thr Asp Ser Gly Leu Ser Met Ser Ser Tyr Ser
            340                 345                 350

Val Pro Arg Thr Pro Asp Asp Phe Leu Asn Ser Val Asp Glu Met Asp
            355                 360                 365

Thr Gly Asp Ser Ile Ser Gln Ser Asn Ile Pro Ser His Gln Asn Arg
370                 375                 380

Phe Pro Asp Tyr Leu Glu Ala Ile Pro Gly Thr Asn Val Asp Leu Gly
385                 390                 395                 400

Thr Leu Glu Gly Asp Gly Met Asn Ile Glu Gly Glu Glu Leu Met Pro
                405                 410                 415

Ser Leu Gln Glu Ala Leu Ser Ser Asp Ile Leu Asn Asp Met Glu Ser
```

```
                        420                 425                 430
            Val Leu Ala Ala Thr Lys Pro Asp Lys Glu Ser Phe Leu Thr Trp Leu
                    435                 440                 445

(2) INFORMATION FOR SEQ ID NO:3:

(i) SEQUENCE CHARACTERISTICS:
        (A) LENGTH: 5115 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Human (vii) IMMEDIATE SOURCE:
        (B) CLONE: YAP (ix) FEATURE:
        (A) NAME/KEY: CDS
        (B) LOCATION: 275..1637

(xi) SEQUENCE DESCRIPTION: SEQ ID NO:3:

GTCGACGGCC ATTATGGATG GATGGCCGAG TGCCTCGCAG CCCCTCCCGA GGCGCAGCCG         60

CCAGACCAGT GGAGCCGGGG CGCAGGGCGG GGGCGGAGGC GCCGGGGCGG GGGATGCGGG        120

GCCGCGGCGC AGCCCCCCGG CCCTGAGAGC GAGGACAGCG CCGCCCGGCC CGCAGCCGTC        180

GCCGCTTCTC CACCTCGGCC CGTGGAGCCG GGCGTCCGG GCGTAGCCCT CGCTCGCCTG         240

GGTCAGGGGG TGCGCGTCGG GGAGGCAGA AGCC ATG GAT CCC GGG CAG CAG            292
                                     Met Asp Pro Gly Gln Gln
                                       1               5

CCG CCG CCT CAA CCG GCC CCC CAG GGC CAA GGG CAG CCG CCT TCG CAG         340
Pro Pro Pro Gln Pro Ala Pro Gln Gly Gln Gly Gln Pro Pro Ser Gln
             10                  15                  20

CCC CCG CAG GGG CAG GGC CCG CCG TCC GGA CCC GGG CAA CCG GCA CCC         388
Pro Pro Gln Gly Gln Gly Pro Pro Ser Gly Pro Gly Gln Pro Ala Pro
         25                  30                  35

GCG GCG ACC CAG GCG GCG CCG CAG GCA CCC CCC GCC GGG CAT CAG ATC         436
Ala Ala Thr Gln Ala Ala Pro Gln Ala Pro Pro Ala Gly His Gln Ile
     40                  45                  50

GTG CAC GTC CGC GGG GAC TCG GAG ACC GAC CTG GAG GCG CTC TTC AAC         484
Val His Val Arg Gly Asp Ser Glu Thr Asp Leu Glu Ala Leu Phe Asn
 55                  60                  65                  70

GCC GTC ATG AAC CCC AAG ACG GCC AAC GTG CCC CAG ACC GTG CCC ATG         532
Ala Val Met Asn Pro Lys Thr Ala Asn Val Pro Gln Thr Val Pro Met
                 75                  80                  85

AGG CTC CGG AAG CTG CCC GAC TCC TTC TTC AAG CCG CCG GAG CCC AAA         580
Arg Leu Arg Lys Leu Pro Asp Ser Phe Phe Lys Pro Pro Glu Pro Lys
             90                  95                 100

TCC CAC TCC CGA CAG GCC AGT ACT GAT GCA GGC ACT GCA GGA GCC CTG         628
Ser His Ser Arg Gln Ala Ser Thr Asp Ala Gly Thr Ala Gly Ala Leu
        105                 110                 115

ACT CCA CAG CAT GTT CGA GCT CAT TCC TCT CCA GCT TCT CTG CAG TTG         676
Thr Pro Gln His Val Arg Ala His Ser Ser Pro Ala Ser Leu Gln Leu
    120                 125                 130

GGA GCT GTT TCT CCT GGG ACA CTG ACC CCC ACT GGA GTA GTC TCT GGC         724
Gly Ala Val Ser Pro Gly Thr Leu Thr Pro Thr Gly Val Val Ser Gly
135                 140                 145                 150
```

-continued

| | |
|---|---|
| CCA GCA GCT ACA CCC ACA GCT CAG CAT CTT CGA CAG TCT TCT TTT GAG<br>Pro Ala Ala Thr Pro Thr Ala Gln His Leu Arg Gln Ser Ser Phe Glu<br>    155                 160                 165 | 772 |
| ATA CCT GAT GAT GTA CCT CTG CCA GCA GGT TGG GAG ATG GCA AAG ACA<br>Ile Pro Asp Asp Val Pro Leu Pro Ala Gly Trp Glu Met Ala Lys Thr<br>        170                 175                 180 | 820 |
| TCT TCT GGT CAG AGA TAC TTC TTA AAT CAC ATC GAT CAG ACA ACA ACA<br>Ser Ser Gly Gln Arg Tyr Phe Leu Asn His Ile Asp Gln Thr Thr Thr<br>            185                 190                 195 | 868 |
| TGG CAG GAC CCC AGG AAG GCC ATG CTG TCC CAG ATG AAC GTC ACA GCC<br>Trp Gln Asp Pro Arg Lys Ala Met Leu Ser Gln Met Asn Val Thr Ala<br>200                 205                 210 | 916 |
| CCC ACC AGT CCA CCA GTG CAG CAG AAT ATG ATG AAC TCG GCT TCA GCC<br>Pro Thr Ser Pro Pro Val Gln Gln Asn Met Met Asn Ser Ala Ser Ala<br>215                 220                 225                 230 | 964 |
| ATG AAC CAG AGA ATC AGT CAG AGT GCT CCA GTG AAA CAG CCA CCA CCC<br>Met Asn Gln Arg Ile Ser Gln Ser Ala Pro Val Lys Gln Pro Pro Pro<br>                235                 240                 245 | 1012 |
| CTG GCT CCC CAG AGC CCA CAG GGA GGC GTC ATG GGT GGC AGC AAC TCC<br>Leu Ala Pro Gln Ser Pro Gln Gly Gly Val Met Gly Gly Ser Asn Ser<br>            250                 255                 260 | 1060 |
| AAC CAG CAG CAA CAG ATG CGA CTG CAG CAA CTG CAG ATG GAG AAG GAG<br>Asn Gln Gln Gln Gln Met Arg Leu Gln Gln Leu Gln Met Glu Lys Glu<br>        265                 270                 275 | 1108 |
| AGG CTG CGG CTG AAA CAG CAA GAA CTG CTT CGG CAG GTG AGG CCA CAG<br>Arg Leu Arg Leu Lys Gln Gln Glu Leu Leu Arg Gln Val Arg Pro Gln<br>    280                 285                 290 | 1156 |
| GAG TTA GCC CTG CGT AGC CAG TTA CCA ACA CTG GAG CAG GAT GGT GGG<br>Glu Leu Ala Leu Arg Ser Gln Leu Pro Thr Leu Glu Gln Asp Gly Gly<br>295                 300                 305                 310 | 1204 |
| ACT CAA AAT CCA GTG TCT TCT CCC GGG ATG TCT CAG GAA TTG AGA ACA<br>Thr Gln Asn Pro Val Ser Ser Pro Gly Met Ser Gln Glu Leu Arg Thr<br>                315                 320                 325 | 1252 |
| ATG ACG ACC AAT AGC TCA GAT CCT TTC CTT AAC AGT GGC ACC TAT CAC<br>Met Thr Thr Asn Ser Ser Asp Pro Phe Leu Asn Ser Gly Thr Tyr His<br>            330                 335                 340 | 1300 |
| TCT CGA GAT GAG AGT ACA GAC AGT GGA CTA AGC ATG AGC AGC TAC AGT<br>Ser Arg Asp Glu Ser Thr Asp Ser Gly Leu Ser Met Ser Ser Tyr Ser<br>        345                 350                 355 | 1348 |
| GTC CCT CGA ACC CCA GAT GAC TTC CTG AAC AGT GTG GAT GAG ATG GAT<br>Val Pro Arg Thr Pro Asp Asp Phe Leu Asn Ser Val Asp Glu Met Asp<br>    360                 365                 370 | 1396 |
| ACA GGT GAT ACT ATC AAC CAA AGC ACC CTG CCC TCA CAG CAG AAC CGT<br>Thr Gly Asp Thr Ile Asn Gln Ser Thr Leu Pro Ser Gln Gln Asn Arg<br>375                 380                 385                 390 | 1444 |
| TTC CCA GAC TAC CTT GAA GCC ATT CCT GGG ACA AAT GTG GAC CTT GGA<br>Phe Pro Asp Tyr Leu Glu Ala Ile Pro Gly Thr Asn Val Asp Leu Gly<br>                395                 400                 405 | 1492 |
| ACA CTG GAA GGA GAT GGA ATG AAC ATA GAA GGA GAG GAG CTG ATG CCA<br>Thr Leu Glu Gly Asp Gly Met Asn Ile Glu Gly Glu Glu Leu Met Pro<br>            410                 415                 420 | 1540 |
| AGT CTG CAG GAA GCT TTG AGT TCT GAC ATC CTT AAT GAC ATG GAG TCT<br>Ser Leu Gln Glu Ala Leu Ser Ser Asp Ile Leu Asn Asp Met Glu Ser<br>        425                 430                 435 | 1588 |
| GTT TTG GCT GCC ACC AAG CTA GAT AAA GAA AGC TTT CTT ACA TGG TTA T<br>Val Leu Ala Ala Thr Lys Leu Asp Lys Glu Ser Phe Leu Thr Trp Leu<br>    440                 445                 450 | 1637 |
| AGAGCCCTCA GGCAGACTGA ATTCTAAATC TGTGAAGGAT CTAAGGAGAC ACATGCACCG | 1697 |
| GAAATTTCCA TAAGCCAGTT GCAGTTTTCA GGCTAATACA GAAAAAGATG AACAAACGTC | 1757 |

-continued

| | |
|---|---|
| CAGCAAGATA CTTTAATCCT CTATTTTGCT CTTCCTTGTC CATTGCTGCT GTTAATGTAT | 1817 |
| TGCTGACCTC TTTCACAGTT GGCTCTAAAG AATCAAAAGA AAAAAACTTT TTATTTCTTT | 1877 |
| TGCTATTAAA ACTACTGTTC ATTTTGGGGG CTGGGGGAAG TGAGCCTGTT TGGATGATGG | 1937 |
| ATGCCATTCC TTTTGCCCAG TTAAATGTTC ACCAATCATT TTAACTAAAT ACTCAGACTT | 1997 |
| AGAAGTCAGA TGCTTCATGT CACAGCATTT AGTTTGTTCA ACAGTTGTTT CTTCAGCTTC | 2057 |
| CTTTGTCCAG TGGAAAAACA TGATTTACTG GTCTGACAAG CCAAAAATGT TATATCTGAT | 2117 |
| ATTAAATACT TAATGCTGAT TTGAAGAGAT AGCTGAAACC AAGGCTGAAG ACTGTTTTAC | 2177 |
| TTTCAGTATT TTCTTTTCCT CCTAGTGCTA TCATTAGTCA CATAATGACC TTGATTTTAT | 2237 |
| TTAGGAGCT TATAAGGCAT GAGACAATTT CCATATAAAT ATATTAATTA TTGCCACATA | 2297 |
| CTCTAATATA GATTTTGGTG GATAATTTTG TGGGTGTGCA TTTTGTTCTG TTTTGTTGGG | 2357 |
| TTTTTTGTTT TTTTTGTTTT TGGCAGGGTC GGTGGGGGGG TTGGTTGGTT GGTTGGTTTT | 2417 |
| GTCGGAACCT AGGCAAATGA CCATATTAGT GAATCTGTTA ATAGTTGTAG CTTGGGATGG | 2477 |
| TTATTGTAGT TGTTTTGGTA AAATCTTCAT TTCCTGGTTT TTTTTACCAC CTTATTTAAA | 2537 |
| TCTCGATTAT CTGCTCTCTC TTTTATATAC ATACACACAC CCAAACATAA CATTTATAAT | 2597 |
| AGTGTGGTAG TGGAATGTAT CCTTTTTTAG GTTTCCCTGC TTTCCAGTTA ATTTTTAAAA | 2657 |
| TGGTAGCGCT TTGTATGCAT TTAGAATACA TGACTAGTAG TTTATATTTC ACTGGTAGTT | 2717 |
| TAAATCTGGT TGGGGCAGTC TGCAGATGTT TGAAGTAGTT TAGTGTTCTA GAAAGAGCTA | 2777 |
| TTACTGTGGA TAGTGCCTAG GGGAGTGCTC CACGCCCTCT GGGCATACGG TAGATATTAT | 2837 |
| CTGATGAATT GGAAAGGAGC AAACCAGAAA TGGCTTTATT TTCTCCCTTG GACTAATTTT | 2897 |
| TAAGTCTCGA TTGAAAATCA GTGAGTAGGT TCATAATGTG CATGACAGAA ATAAGCTTTA | 2957 |
| TAGTGGTTTA CCTTCATTTA GCTTTGGAAG TTTTCTTTGC CTTAGTTTTG GAAGTAAATT | 3017 |
| CTAGTTTGTA GTTCTCATTT GTAATGAACA CATTAACGAC TAGATTAAAA TATTGCCTTC | 3077 |
| AAGATTGTTC TTACTTACAA GACTTGCTCC TACTTCTATG CTGAAAATTG ACCCTGGATA | 3137 |
| GAATACTATA AGGTTTTGAG TTAGCTGGAA AAGTGATCGA ATTAATAAAT GTATATTGGT | 3197 |
| AGTTGAATTT AGCAAAGAAA TAGAGATAAT CATGATTATA CCTTTATTTT TACAGGAAGA | 3257 |
| GATGATGTAA CTAGAGTATG TGTCTACAGG AGTAATAATG GTTTCCAAAG AGTATTTTTT | 3317 |
| AAAGGAACAA AACGAGCATG AATTAACTCT TCAATATAAG CTATGAAGTA ATAGTTGGTT | 3377 |
| GTGAATTAAA GTGGCACCAG CTAGCACCTC TGTGTTTTAA GGGTCTTTCA ATGTTTCTAG | 3437 |
| AATAAGCCCT TATTTTCAAG GGTTCATAAC AGGCATAAAA TCTCTTCTCC TGGCAAAAGC | 3497 |
| TGCTATGAAA AGCCTCAGCT TGGGAAGATA GATTTTTTTC CCCCCAATTA CAAAATCTAA | 3557 |
| GTATTTTGGC CCTTCAATTT GGAGGAGGGC AAAAGTTGGA AGTAAGAAGT TTTATTTTAA | 3617 |
| GTACTTTCAG TGCTCAAAAA AATGCAATCA CTGTGTTGTA TATAATAGTT CATAGGTTGA | 3677 |
| TCACTCATAA TAATTGACTC TAAGGCTTTT ATTAAGAAAA CAGCAGAAAG ATTAAATCTT | 3737 |
| GAATTAAGTC TGGGGGGAAA TGGCCACTGC AGATGGAGTT TTAGAGTAGT AATGAAATTC | 3797 |
| TACCTAGAAT GCAAAATTGG GTATATGAAT TACATAGCAT GTTGTTGGGA TTTTTTTTAA | 3857 |
| TGTGCAGAAG ATCAAAGCTA CTTGGAAGGA GTGCCTATAA TTTGCCAGTA GCCACAGATT | 3917 |
| AAGATTATAT CTTATATATC AGCAGATTAG CTTTAGCTTA GGGGGAGGGT GGGAAAGTTT | 3977 |
| GGGGGGGGGG TTGTGAAGAT TTAGGGGGAC CTTGATAGAG AACTTTATAA ACTTCTTTCT | 4037 |
| CTTTAATAAA GACTTGTCTT ACACCGTGCT GCCATTAAAG GCAGCTGTTC TAGAGTTTCA | 4097 |
| GTCACCTAAG TACACCCACA AAACAATATG AATATGGAGA TCTTCCTTTA CCCCTCAACT | 4157 |

```
TTAATTTGCC CAGTTATACC TCAGTGTTGT AGCAGTACTG TGATACCTGG CACAGTGCTT      4217

TGATCTTACG ATGCCCTCTG TACTGACCTG AAGGAGACCT AAGAGTCCTT TCCCTTTTTG      4277

AGTTTGAATC ATAGCCTTGA TGTGGTCTCT TGTTTTATGT CCTTGTTCCT AATGTAAAAG      4337

TGCTTAACTG CTTCTTGGTT GTATTGGGTA GCATTGGGAT AAGATTTAA CTGGGTATTC       4397

TTGAATTGCT TTTACAATAA ACCAATTTTA TAATCTTTAA ATTTATCAAC TTTTTACATT      4457

TGTGTTATTT TCAGTCAGGG CTTCTTAGAT CTACTTATGG TTGATGGAGC ACATTGATTT      4517

GGAGTTTCAG ATCTTCCAAA GCACTATTTG TTGTAATAAC TTTTCTAAAT ATAGTGCCTT      4577

TAAAGGAAAA ATGAACACAG GGAAGTGACT TTGCTACAAA TAATGTTGCT GTGTTAAGTA      4637

TTCATATTAA ATACATGCCT TCTATATGGA ACATGGCAGA AAGACTGAAA AATAACAGTA      4697

ATTAATTGTG TAATTCAGAA TTCATACCAA TCAGTGTTGA AACTCAAACA TTGCAAAAGT      4757

GGGTGGCAAT ATTCAGTGCT TAACACTTTT CTAGCGTTGG TACATCTGAG AAATGAGTGC      4817

TCAGGTGGAT TTTATCCTCG CAAGCATGTT GTTATAAGAA TTGTGGGTGT GCCTATCATA      4877

ACAATTGTTT TCTGTATCTT GAAAAAGTAT TCTCCACATT TTAAATGTTT TATATTAGAG      4937

AATTCTTTAA TGCACACTTG TCAAATATAT ATATATAGTA CCAATGTTAC CTTTTTATTT      4997

TTTGTTTTAG ATGTAAGAGC ATGCTCATAT GTTAGGTACT TACATAAATT GTTACATTAT      5057

TTTTTCTTAT GTAATACCTT TTTGTTTGTT TATGTGGTTC AAATATATTC TTTCCTTA       5115
```

(2) INFORMATION FOR SEQ ID NO:4:

(i) SEQUENCE CHARACTERISTICS:
        (A) LENGTH: 454 amino acids
        (B) TYPE: amino acid
        (D) TOPOLOGY: linear (ii) MOLECULE TYPE: protein (xi) SEQUENCE DESCRIPTION: SEQ ID NO:4:

```
Met Asp Pro Gly Gln Gln Pro Pro Gln Pro Ala Pro Gln Gly Gln
 1               5                  10                  15

Gly Gln Pro Pro Ser Gln Pro Gln Gly Gln Gly Pro Pro Ser Gly
                20                  25                  30

Pro Gly Gln Pro Ala Pro Ala Ala Thr Gln Ala Ala Pro Gln Ala Pro
                35                  40                  45

Pro Ala Gly His Gln Ile Val His Val Arg Gly Asp Ser Glu Thr Asp
 50                  55                  60

Leu Glu Ala Leu Phe Asn Ala Val Met Asn Pro Lys Thr Ala Asn Val
 65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
                100                 105                 110

Gly Thr Ala Gly Ala Leu Thr Pro Gln His Val Arg Ala His Ser Ser
            115                 120                 125

Pro Ala Ser Leu Gln Leu Gly Ala Val Ser Pro Gly Thr Leu Thr Pro
        130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
                180                 185                 190
```

```
Ile Asp Gln Thr Thr Thr Trp Gln Asp Pro Arg Lys Ala Met Leu Ser
            195                 200                 205

Gln Met Asn Val Thr Ala Pro Thr Ser Pro Pro Val Gln Gln Asn Met
    210                 215                 220

Met Asn Ser Ala Ser Ala Met Asn Gln Arg Ile Ser Gln Ser Ala Pro
225                 230                 235                 240

Val Lys Gln Pro Pro Pro Leu Ala Pro Gln Ser Pro Gln Gly Gly Val
                245                 250                 255

Met Gly Gly Ser Asn Ser Asn Gln Gln Gln Met Arg Leu Gln Gln
            260                 265                 270

Leu Gln Met Glu Lys Glu Arg Leu Arg Leu Lys Gln Gln Glu Leu Leu
        275                 280                 285

Arg Gln Val Arg Pro Gln Glu Leu Ala Leu Arg Ser Gln Leu Pro Thr
        290                 295                 300

Leu Glu Gln Asp Gly Gly Thr Gln Asn Pro Val Ser Ser Pro Gly Met
305                 310                 315                 320

Ser Gln Glu Leu Arg Thr Met Thr Thr Asn Ser Ser Asp Pro Phe Leu
                325                 330                 335

Asn Ser Gly Thr Tyr His Ser Arg Asp Glu Ser Thr Asp Ser Gly Leu
                340                 345                 350

Ser Met Ser Ser Tyr Ser Val Pro Arg Thr Pro Asp Asp Phe Leu Asn
            355                 360                 365

Ser Val Asp Glu Met Asp Thr Gly Asp Thr Ile Asn Gln Ser Thr Leu
370                 375                 380

Pro Ser Gln Gln Asn Arg Phe Pro Asp Tyr Leu Glu Ala Ile Pro Gly
385                 390                 395                 400

Thr Asn Val Asp Leu Gly Thr Leu Glu Gly Asp Gly Met Asn Ile Glu
                405                 410                 415

Gly Glu Glu Leu Met Pro Ser Leu Gln Glu Ala Leu Ser Ser Asp Ile
            420                 425                 430

Leu Asn Asp Met Glu Ser Val Leu Ala Ala Thr Lys Leu Asp Lys Glu
        435                 440                 445

Ser Phe Leu Thr Trp Leu
    450

(2) INFORMATION FOR SEQ ID NO:5:

(i) SEQUENCE CHARACTERISTICS:
        (A) LENGTH: 472 amino acids
        (B) TYPE: amino acid
        (D) TOPOLOGY: linear (ii) MOLECULE TYPE: protein (iii) HYPOTHETICAL: NO (vi) ORIGINAL SOURCE:
        (A) ORGANISM: Mouse (vii) IMMEDIATE SOURCE:
        (B) CLONE: YAP (xi) SEQUENCE DESCRIPTION: SEQ ID NO:5:

Met Glu Pro Ala Gln Gln Pro Pro Gln Pro Ala Pro Gln Gly Pro
1               5                   10                  15

Ala Pro Pro Ser Val Ser Pro Ala Gly Thr Pro Ala Ala Pro Pro Ala
                20                  25                  30

Pro Pro Ala Gly His Gln Val Val His Val Arg Gly Asp Ser Glu Thr
                35                  40                  45
```

```
Asp Leu Glu Ala Leu Phe Asn Ala Val Met Asn Pro Lys Thr Ala Asn
 50                  55                  60
Val Pro Gln Thr Val Pro Met Arg Leu Arg Lys Leu Pro Asp Ser Phe
 65                  70                  75                  80
Phe Lys Pro Pro Glu Pro Lys Ser His Ser Arg Gln Ala Ser Thr Asp
                 85                  90                  95
Ala Gly Thr Ala Gly Ala Leu Thr Pro Gln His Val Arg Ala His Ser
            100                 105                 110
Ser Pro Ala Ser Leu Gln Leu Gly Ala Val Ser Pro Gly Thr Leu Thr
        115                 120                 125
Ala Ser Gly Val Val Ser Gly Pro Ala Ala Pro Ala Ala Gln His
130                 135                 140
Leu Arg Gln Ser Ser Phe Glu Ile Pro Asp Asp Val Pro Leu Pro Ala
145                 150                 155                 160
Gly Trp Glu Met Ala Lys Thr Ser Ser Gly Gln Arg Tyr Phe Leu Asn
                165                 170                 175
His Asn Asp Gln Thr Thr Thr Trp Gln Asp Pro Arg Lys Ala Met Leu
            180                 185                 190
Ser Gln Leu Asn Val Pro Ala Pro Ala Ser Pro Ala Val Pro Gln Thr
        195                 200                 205
Leu Met Asn Ser Ala Ser Gly Pro Leu Pro Asp Gly Trp Glu Gln Ala
210                 215                 220
Met Thr Gln Asp Gly Glu Val Tyr Tyr Ile Asn His Lys Asn Lys Thr
225                 230                 235                 240
Thr Ser Trp Leu Asp Pro Arg Leu Asp Pro Arg Phe Ala Met Asn Gln
                245                 250                 255
Arg Ile Thr Gln Ser Ala Pro Val Lys Gln Pro Pro Pro Leu Ala Pro
            260                 265                 270
Gln Ser Pro Gln Gly Gly Val Leu Gly Gly Ser Ser Asn Gln Gln
        275                 280                 285
Gln Gln Ile Gln Leu Gln Gln Leu Gln Met Glu Lys Glu Arg Leu Arg
        290                 295                 300
Leu Lys Gln Gln Glu Leu Phe Arg Gln Glu Leu Ala Leu Arg Ser Gln
305                 310                 315                 320
Leu Pro Thr Leu Glu Gln Asp Gly Gly Thr Pro Asn Ala Val Ser Ser
                325                 330                 335
Pro Gly Met Ser Gln Glu Leu Arg Thr Met Thr Thr Asn Ser Ser Asp
            340                 345                 350
Pro Phe Leu Asn Ser Gly Thr Tyr His Ser Arg Asp Glu Ser Thr Asp
        355                 360                 365
Ser Gly Leu Ser Met Ser Ser Tyr Ser Ile Pro Arg Thr Pro Asp Asp
370                 375                 380
Phe Leu Asn Ser Val Asp Glu Met Asp Thr Gly Asp Thr Ile Ser Gln
385                 390                 395                 400
Ser Thr Leu Pro Ser Gln Gln Ser Arg Phe Pro Asp Tyr Leu Glu Ala
                405                 410                 415
Leu Pro Gly Thr Asn Val Asp Leu Gly Thr Leu Glu Gly Asp Ala Met
            420                 425                 430
Asn Ile Glu Gly Glu Glu Leu Met Pro Ser Leu Gln Glu Ala Leu Ser
        435                 440                 445
Ser Glu Ile Leu Asp Val Glu Ser Val Leu Ala Ala Thr Lys Leu Asp
450                 455                 460
Lys Glu Ser Phe Leu Thr Trp Leu
465                 470
```

(2) INFORMATION FOR SEQ ID NO:6:

(i) SEQUENCE CHARACTERISTICS:
        (A) LENGTH: 38 amino acids
        (B) TYPE: amino acid
        (D) TOPOLOGY: linear (ii) MOLECULE TYPE: protein (iii) HYPOTHETICAL: NO (v) FRAGMENT TYPE: internal (vi) ORIGINAL SOURCE:
        (A) ORGANISM: Human (vii) IMMEDIATE SOURCE:
        (B) CLONE: Dmd (xi) SEQUENCE DESCRIPTION: SEQ ID NO:6:

Thr Ser Val Gln Gly Pro Trp Glu Arg Ala Ile Ser Pro Asn Lys Val
1               5                   10                  15

Pro Tyr Tyr Ile Asn His Glu Thr Gln Thr Thr Cys Trp Asp His Pro
            20                  25                  30

Lys Met Thr Glu Leu Tyr
            35

(2) INFORMATION FOR SEQ ID NO:7:

(i) SEQUENCE CHARACTERISTICS:
        (A) LENGTH: 38 amino acids
        (B) TYPE: amino acid
        (D) TOPOLOGY: linear (ii) MOLECULE TYPE: protein (iii) HYPOTHETICAL: NO (v) FRAGMENT TYPE: internal (vi) ORIGINAL SOURCE:
        (A) ORGANISM: Ray (vii) IMMEDIATE SOURCE:
        (B) CLONE: Dmd (xi) SEQUENCE DESCRIPTION: SEQ ID NO:7:

Thr Ser Val Gln Gly Pro Trp Glu Arg Ala Ile Ser Pro Asn Lys Val
1               5                   10                  15

Pro Tyr Tyr Ile Asn His Gln Thr Gln Thr Thr Cys Trp Asp His Pro
            20                  25                  30

Lys Met Thr Glu Leu Tyr
            35

(2) INFORMATION FOR SEQ ID NO:8:

(i) SEQUENCE CHARACTERISTICS:
        (A) LENGTH: 38 amino acids
        (B) TYPE: amino acid
        (D) TOPOLOGY: linear (ii) MOLECULE TYPE: protein (iii) HYPOTHETICAL: NO (v) FRAGMENT TYPE: internal (vi) ORIGINAL SOURCE:
        (A) ORGANISM: Human (vii) IMMEDIATE SOURCE:
    (B) CLONE: Utro (xi) SEQUENCE DESCRIPTION: SEQ ID NO:8:

Thr Ser Val Gln Leu Pro Trp Gln Arg Ser Ile Ser His Asn Lys Val
1               5                   10                  15

Pro Tyr Tyr Ile Asn His Gln Thr Gln Thr Thr Cys Trp Asp His Pro
                20                  25                  30

Lys Met Thr Glu Leu Phe
            35

(2) INFORMATION FOR SEQ ID NO:9:

(i) SEQUENCE CHARACTERISTICS:
        (A) LENGTH: 38 amino acids
        (B) TYPE: amino acid
        (D) TOPOLOGY: linear (ii) MOLECULE TYPE: protein (iii) HYPOTHETICAL: NO (v) FRAGMENT TYPE: internal (vi) ORIGINAL SOURCE:
        (A) ORGANISM: Human (vii) IMMEDIATE SOURCE:
        (B) CLONE: Yap (xi) SEQUENCE DESCRIPTION: SEQ ID NO:9:

Val Pro Leu Pro Ala Gly Trp Glu Met Ala Lys Thr Ser Ser Gly Gln
1               5                   10                  15

Arg Tyr Phe Leu Asn His Ile Asp Gln Thr Thr Thr Trp Gln Asp Pro
                20                  25                  30

Arg Lys Ala Met Leu Ser
            35

(2) INFORMATION FOR SEQ ID NO:10:

(i) SEQUENCE CHARACTERISTICS:
        (A) LENGTH: 38 amino acids
        (B) TYPE: amino acid
        (D) TOPOLOGY: linear (ii) MOLECULE TYPE: protein (iii) HYPOTHETICAL: NO (v) FRAGMENT TYPE: internal (vi) ORIGINAL SOURCE:
        (A) ORGANISM: Chick (vii) IMMEDIATE SOURCE:
        (B) CLONE: Yap (xi) SEQUENCE DESCRIPTION: SEQ ID NO:10:

Val Pro Leu Pro Pro Gly Trp Glu Met Ala Lys Thr Pro Ser Gly Gln
1               5                   10                  15

Arg Tyr Phe Leu Asn His Ile Asp Gln Thr Thr Thr Trp Gln Asp Pro
                20                  25                  30

Arg Lys Ala Met Leu Ser
            35

(2) INFORMATION FOR SEQ ID NO:11:

(i) SEQUENCE CHARACTERISTICS:

(A) LENGTH: 38 amino acids
           (B) TYPE: amino acid
           (D) TOPOLOGY: linear (ii) MOLECULE TYPE: protein (iii) HYPOTHETICAL: NO (v) FRAGMENT TYPE: internal (vi) ORIGINAL SOURCE:
           (A) ORGANISM: Mouse-1

(vii) IMMEDIATE SOURCE:
           (B) CLONE: Yap (xi) SEQUENCE DESCRIPTION: SEQ ID NO:11:

Val Pro Leu Pro Ala Gly Trp Glu Met Ala Lys Thr Ser Ser Gly Gln
1               5                  10                  15

Arg Tyr Phe Leu Asn His Asn Asp Gln Thr Thr Thr Trp Gln Asp Pro
            20                  25                  30

Arg Lys Ala Met Leu Ser
        35

(2) INFORMATION FOR SEQ ID NO:12:

(i) SEQUENCE CHARACTERISTICS:
           (A) LENGTH: 38 amino acids
           (B) TYPE: amino acid
           (D) TOPOLOGY: linear (ii) MOLECULE TYPE: protein (iii) HYPOTHETICAL: NO (v) FRAGMENT TYPE: internal (vi) ORIGINAL SOURCE:
           (A) ORGANISM: Mouse-2

(vii) IMMEDIATE SOURCE:
           (B) CLONE: Yap (xi) SEQUENCE DESCRIPTION: SEQ ID NO:12:

Gly Pro Leu Pro Asp Gly Trp Glu Gln Ala Met Thr Gln Asp Gly Glu
1               5                  10                  15

Val Tyr Tyr Ile Asn His Lys Asn Lys Thr Thr Ser Trp Leu Asp Pro
            20                  25                  30

Arg Leu Asp Pro Arg Phe
        35

(2) INFORMATION FOR SEQ ID NO:13:

(i) SEQUENCE CHARACTERISTICS:
           (A) LENGTH: 38 amino acids
           (B) TYPE: amino acid
           (D) TOPOLOGY: linear (ii) MOLECULE TYPE: protein (iii) HYPOTHETICAL: NO (v) FRAGMENT TYPE: internal (vi) ORIGINAL SOURCE:
           (A) ORGANISM: Mouse-1

(vii) IMMEDIATE SOURCE:
           (B) CLONE: Nedd4

(xi) SEQUENCE DESCRIPTION: SEQ ID NO:13:

```
Ser Pro Leu Pro Pro Gly Trp Glu Glu Arg Gln Asp Val Leu Gly Arg
1               5                   10                  15

Thr Tyr Tyr Val Asn His Glu Ser Arg Arg Thr Gln Trp Lys Arg Pro
            20                  25                  30

Ser Pro Asp Asp Asp Leu
        35
```

(2) INFORMATION FOR SEQ ID NO:14:

(i) SEQUENCE CHARACTERISTICS:
        (A) LENGTH: 38 amino acids
        (B) TYPE: amino acid
        (D) TOPOLOGY: linear (ii) MOLECULE TYPE: protein (iii) HYPOTHETICAL: NO (v) FRAGMENT TYPE: internal (vi) ORIGINAL SOURCE:
       (A) ORGANISM: Mouse-2

(vii) IMMEDIATE SOURCE:
       (B) CLONE: Nedd4

(xi) SEQUENCE DESCRIPTION: SEQ ID NO:14:

```
Ser Gly Leu Pro Pro Gly Trp Glu Glu Lys Gln Asp Asp Arg Gly Arg
1               5                   10                  15

Ser Tyr Tyr Val Asp His Asn Ser Lys Thr Thr Thr Trp Ser Lys Pro
            20                  25                  30

Thr Met Gln Asp Asp Pro
        35
```

(2) INFORMATION FOR SEQ ID NO:15:

(i) SEQUENCE CHARACTERISTICS:
        (A) LENGTH: 38 amino acids
        (B) TYPE: amino acid
        (D) TOPOLOGY: linear (ii) MOLECULE TYPE: protein (iii) HYPOTHETICAL: NO (v) FRAGMENT TYPE: internal (vi) ORIGINAL SOURCE:
       (A) ORGANISM: Mouse-3

(vii) IMMEDIATE SOURCE:
       (B) CLONE: Nedd4

(xi) SEQUENCE DESCRIPTION: SEQ ID NO:15:

```
Gly Pro Leu Pro Pro Gly Trp Glu Glu Arg Thr His Thr Asp Gly Arg
1               5                   10                  15

Val Phe Phe Ile Asn His Asn Ile Lys Lys Thr Gln Trp Glu Asp Pro
            20                  25                  30

Arg Leu Gln Asn Val Ala
        35
```

(2) INFORMATION FOR SEQ ID NO:16:

(i) SEQUENCE CHARACTERISTICS:
        (A) LENGTH: 38 amino acids
        (B) TYPE: amino acid
        (D) TOPOLOGY: linear (ii) MOLECULE TYPE: protein (iii) HYPOTHETICAL: NO (v) FRAGMENT TYPE: internal (vi) ORIGINAL SOURCE:
                 (A) ORGANISM: Yeast-1

(vii) IMMEDIATE SOURCE:
                 (B) CLONE: Rsp5

(xi) SEQUENCE DESCRIPTION: SEQ ID NO:16:

Gly Arg Leu Pro Pro Gly Trp Glu Arg Arg Thr Asp Asn Phe Gly Arg
1               5                  10                  15

Thr Tyr Tyr Val Asp His Asn Thr Arg Thr Thr Thr Trp Lys Arg Pro
            20                  25                  30

Thr Leu Asp Gln Thr Glu
            35

(2) INFORMATION FOR SEQ ID NO:17:

(i) SEQUENCE CHARACTERISTICS:
                 (A) LENGTH: 38 amino acids
                 (B) TYPE: amino acid
                 (D) TOPOLOGY: linear (ii) MOLECULE TYPE: protein (iii) HYPOTHETICAL: NO (v) FRAGMENT TYPE: internal (vi) ORIGINAL SOURCE:
                 (A) ORGANISM: Yeast-2

(vii) IMMEDIATE SOURCE:
                 (B) CLONE: Rsp5

(xi) SEQUENCE DESCRIPTION: SEQ ID NO:17:

Gly Glu Leu Pro Ser Gly Trp Glu Gln Arg Phe Thr Pro Glu Gly Arg
1               5                  10                  15

Ala Tyr Phe Val Asp His Asn Thr Arg Thr Thr Thr Trp Val Asp Pro
            20                  25                  30

Arg Arg Gln Gln Tyr Ile
            35

(2) INFORMATION FOR SEQ ID NO:18:

(i) SEQUENCE CHARACTERISTICS:
                 (A) LENGTH: 38 amino acids
                 (B) TYPE: amino acid
                 (D) TOPOLOGY: linear (ii) MOLECULE TYPE: protein (iii) HYPOTHETICAL: NO (v) FRAGMENT TYPE: internal (vi) ORIGINAL SOURCE:
                 (A) ORGANISM: Yeast-3

(vii) IMMEDIATE SOURCE:
                 (B) CLONE: Rsp5

(xi) SEQUENCE DESCRIPTION: SEQ ID NO:18:

Gly Pro Leu Pro Ser Gly Trp Glu Met Arg Leu Thr Asn Thr Ala Arg
1               5                  10                  15

Val Tyr Phe Val Asp His Asn Thr Lys Thr Thr Thr Trp Asp Asp Pro
            20                  25                  30

```
Arg Leu Pro Ser Ser Leu
        35

(2) INFORMATION FOR SEQ ID NO:19:

(i) SEQUENCE CHARACTERISTICS:
        (A) LENGTH: 35 amino acids
        (B) TYPE: amino acid
        (D) TOPOLOGY: linear (ii) MOLECULE TYPE: protein (iii) HYPOTHETICAL: NO (v) FRAGMENT TYPE: internal (vi) ORIGINAL SOURCE:
        (A) ORGANISM: Yeast-1

(vii) IMMEDIATE SOURCE:
        (B) CLONE: Ykb2

(xi) SEQUENCE DESCRIPTION: SEQ ID NO:19:

Met Ser Ile Trp Lys Glu Ala Lys Asp Ala Ser Gly Arg Ile Tyr Tyr
1               5                  10                  15

Tyr Asn Thr Leu Thr Lys Lys Ser Thr Trp Glu Lys Pro Lys Glu Leu
             20                  25                  30

Ile Ser Gln
        35

(2) INFORMATION FOR SEQ ID NO:20:

(i) SEQUENCE CHARACTERISTICS:
        (A) LENGTH: 38 amino acids
        (B) TYPE: amino acid
        (D) TOPOLOGY: linear (ii) MOLECULE TYPE: protein (iii) HYPOTHETICAL: NO (v) FRAGMENT TYPE: internal (vi) ORIGINAL SOURCE:
        (A) ORGANISM: Yeast-2

(vii) IMMEDIATE SOURCE:
        (B) CLONE: Ykb2

(xi) SEQUENCE DESCRIPTION: SEQ ID NO:20:

Leu Leu Arg Glu Asn Gly Trp Lys Ala Ala Lys Thr Ala Asp Gly Lys
1               5                  10                  15

Val Tyr Tyr Tyr Asn Pro Thr Thr Arg Glu Thr Ser Trp Thr Ile Pro
             20                  25                  30

Phe Glu Lys Lys Val Glu
        35

(2) INFORMATION FOR SEQ ID NO:21:

(i) SEQUENCE CHARACTERISTICS:
        (A) LENGTH: 38 amino acids
        (B) TYPE: amino acid
        (D) TOPOLOGY: linear (ii) MOLECULE TYPE: protein (iii) HYPOTHETICAL: NO (v) FRAGMENT TYPE: internal
```

```
          (vi) ORIGINAL SOURCE:
                (A) ORGANISM: Caeel-1

(vii) IMMEDIATE SOURCE:
                (B) CLONE: Yo61

(xi) SEQUENCE DESCRIPTION: SEQ ID NO:21:

Pro Ser Val Glu Ser Asp Trp Ser Val His Thr Asn Glu Lys Gly Thr
1               5                  10                  15

Pro Tyr Tyr His Asn Arg Val Thr Lys Gln Thr Ser Trp Ile Lys Pro
             20                  25                  30

Asp Val Leu Lys Thr Pro
         35

(2) INFORMATION FOR SEQ ID NO:22:

(i) SEQUENCE CHARACTERISTICS:
                (A) LENGTH: 38 amino acids
                (B) TYPE: amino acid
                (D) TOPOLOGY: linear (ii) MOLECULE TYPE: protein (iii) HYPOTHETICAL: NO (v) FRAGMENT TYPE: internal (vi) ORIGINAL SOURCE:
                (A) ORGANISM: Caeel-2

(vii) IMMEDIATE SOURCE:
                (B) CLONE: Yo61

(xi) SEQUENCE DESCRIPTION: SEQ ID NO:22:

Gln Pro Gln Gln Gly Gln Trp Lys Glu Phe Met Ser Asp Asp Gly Lys
1               5                  10                  15

Pro Tyr Tyr Tyr Asn Thr Leu Thr Lys Lys Thr Gln Trp Val Lys Pro
             20                  25                  30

Asp Gly Glu Glu Ile Thr
         35

(2) INFORMATION FOR SEQ ID NO:23:

(i) SEQUENCE CHARACTERISTICS:
                (A) LENGTH: 38 amino acids
                (B) TYPE: amino acid
                (D) TOPOLOGY: linear (ii) MOLECULE TYPE: protein (iii) HYPOTHETICAL: NO (v) FRAGMENT TYPE: internal (vi) ORIGINAL SOURCE:
                (A) ORGANISM: Amoeba (vii) IMMEDIATE SOURCE:
                (B) CLONE: Amoe (xi) SEQUENCE DESCRIPTION: SEQ ID NO:23:

Lys Met Ser Val Asp Gly Trp Ser Gln Tyr Phe Thr Ala Glu Gly Asn
1               5                  10                  15

Ala Tyr Tyr Tyr Asn Glu Val Ser Gly Glu Thr Ser Trp Asp Pro Pro
             20                  25                  30

Ser Ser Leu Gln Ser His
         35
```

```
(2) INFORMATION FOR SEQ ID NO:24:

(i) SEQUENCE CHARACTERISTICS:
        (A) LENGTH: 37 amino acids
        (B) TYPE: amino acid
        (D) TOPOLOGY: linear (ii) MOLECULE TYPE: protein (iii) HYPOTHETICAL: NO (v) FRAGMENT TYPE: internal (vi) ORIGINAL SOURCE:
        (A) ORGANISM: Rat (vii) IMMEDIATE SOURCE:
        (B) CLONE: FE65

(xi) SEQUENCE DESCRIPTION: SEQ ID NO:24:

Ser Asp Leu Pro Ala Gly Trp Met Arg Val Gln Asp Thr Ser Gly Thr
1               5                   10                  15

Tyr Tyr Trp His Ile Pro Thr Gly Thr Thr Gln Trp Glu Pro Pro Gly
            20                  25                  30

Arg Ala Ser Pro Ser
        35

(2) INFORMATION FOR SEQ ID NO:25:

(i) SEQUENCE CHARACTERISTICS:
        (A) LENGTH: 39 amino acids
        (B) TYPE: amino acid
        (D) TOPOLOGY: linear (ii) MOLECULE TYPE: protein (iii) HYPOTHETICAL: NO (v) FRAGMENT TYPE: internal (vi) ORIGINAL SOURCE:
        (A) ORGANISM: Yeast (vii) IMMEDIATE SOURCE:
        (B) CLONE: Ess1

(xi) SEQUENCE DESCRIPTION: SEQ ID NO:25:

Thr Gly Leu Pro Thr Pro Trp Thr Ala Arg Tyr Ser Lys Ser Lys Lys
1               5                   10                  15

Arg Glu Tyr Phe Phe Asn Pro Glu Thr Lys His Ser Gln Trp Glu Glu
            20                  25                  30

Pro Glu Gly Thr Asn Lys Asp
        35

(2) INFORMATION FOR SEQ ID NO:26:

(i) SEQUENCE CHARACTERISTICS:
        (A) LENGTH: 10 amino acids
        (B) TYPE: amino acid
        (D) TOPOLOGY: linear (ii) MOLECULE TYPE: protein (iii) HYPOTHETICAL: NO (v) FRAGMENT TYPE: internal (xi) SEQUENCE DESCRIPTION: SEQ ID NO:26:

Pro Val Lys Gln Pro Pro Pro Leu Ala Pro
1               5                   10
```